(12) United States Patent
Lane et al.

(10) Patent No.: US 9,970,938 B2
(45) Date of Patent: *May 15, 2018

(54) USE OF BUBR1 AS A BIOMARKER OF DRUG RESPONSE TO FURAZANOBENZIMIDAZOLES

(71) Applicant: Basilea Pharmaceutica AG, Basel (CH)

(72) Inventors: Heidi Alexandra Lane, Therwil (CH); Felix Bachmann, Basel (CH); Madlaina Breuleux, Basel (CH); Michael Boutros, Heidelberg (DE); Daniel Gilbert, Heidelberg (DE); Xian Zhang, Heidelberg (DE)

(73) Assignee: BASILEA PHARMACEUTICA AG, Basel (CH)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/060,998

(22) Filed: Mar. 4, 2016

(65) Prior Publication Data

US 2016/0320397 A1 Nov. 3, 2016

Related U.S. Application Data

(62) Division of application No. 13/980,180, filed as application No. PCT/EP2012/050818 on Jan. 19, 2012.

(30) Foreign Application Priority Data

Jan. 21, 2011 (EP) .................................... 11151677

(51) Int. Cl.
*G01N 33/574* (2006.01)
*A61K 31/4245* (2006.01)
(Continued)

(52) U.S. Cl.
CPC ... *G01N 33/57484* (2013.01); *A61K 31/4245* (2013.01); *A61K 31/4439* (2013.01);
(Continued)

(58) Field of Classification Search
CPC .......... G01N 33/57484; A61K 31/4245; A61K 31/4439
(Continued)

(56) References Cited

U.S. PATENT DOCUMENTS 8,021,831 B2 9/2011 Ueno et al.
2009/0226894 A1 9/2009 Grueneberg et al.

FOREIGN PATENT DOCUMENTS

WO 9856910 A1 12/1998
WO 2004103994 A1 12/2004
(Continued)

OTHER PUBLICATIONS

Expert Opin. Ther. Targets (2011) 15(11):1249-1266.*
(Continued)

*Primary Examiner* — Shirley V Gembeh

(57) ABSTRACT

Use of BUBR1 as a biomarker for predicting the response to a compound, preferably resistance of a disease such as cancer in a subject, wherein the compound is a compound of general formula I

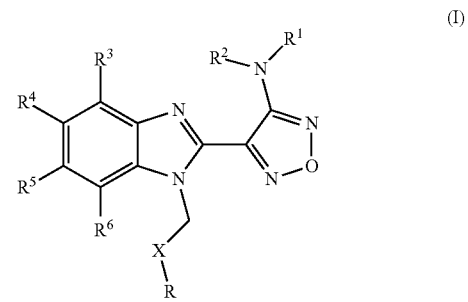

(I)

wherein
R represents phenyl, thienyl or pyridinyl
wherein phenyl is optionally substituted by one or two substituents independently selected from alkyl, halo-lower alkyl, hydroxy-lower alkyl, lower alkoxy-lower alkyl, acyloxy-lower alkyl, phenyl, hydroxy, lower alkoxy, hydroxy-lower alkoxy, lower alkoxy-lower alkoxy, phenyl-lower alkoxy, lower alkylcarbonyloxy, amino, monoalkylamino, dialkylamino, lower alkoxycarbonylamino, lower alkylcarbonylamino, substituted amino wherein the two substituents on nitrogen form together with the nitrogen heterocyclyl, lower alkylcarbonyl, carboxy, lower alkoxycarbonyl, cyano, halogen, and nitro; and wherein two adjacent substituents are methylenedioxy;
and wherein pyridinyl is optionally substituted by lower alkoxy, amino or halogen;
X represents a group C=Y, wherein Y stands for oxygen or nitrogen substituted by hydroxy or lower alkoxy;
$R^1$ represents hydrogen, lower alkylcarbonyl, hydroxy-lower alkyl or cyano-lower alkyl;
$R^2$, $R^3$ and $R^6$ represent hydrogen;
$R^4$ and $R^5$, independently of each other, represent hydrogen, lower alkyl or lower alkoxy;
or $R^4$ and $R^5$ together represent methylenedioxy;
and pharmaceutically acceptable derivatives thereof;
or wherein
R represents phenyl or pyridinyl
wherein phenyl is optionally substituted by one or two substituents independently selected from alkyl, halo-lower alkyl, hydroxy-lower alkyl, lower alkoxy-lower alkyl, acyloxy-lower alkyl, phenyl, hydroxy, lower alkoxy, hydroxy-lower alkoxy, lower alkoxy-lower alkoxy, phenyl-lower alkoxy, lower alkylcarbonyloxy, amino, monoalkylamino, dialkylamino, lower alkoxycarbonylamino, lower alkylcarbonylamino, substituted
(Continued)

amino wherein the two substituents on nitrogen form together with the nitrogen heterocyclyl, lower alkylcarbonyl, carboxy, lower alkoxycarbonyl, formyl, cyano, halogen, and nitro; and wherein two adjacent substituents are methylenedioxy;

and wherein pyridinyl is optionally substituted by lower alkoxy, amino or halogen;

X represents oxygen;

$R^1$ represents hydrogen, lower alkylcarbonyl, hydroxy-lower alkyl or cyano-lower alkyl;

$R^2$, $R^3$ and $R^6$ represent hydrogen;

$R^4$ and $R^5$, independently of each other, represent hydrogen, lower alkyl or lower alkoxy;

or $R^4$ and $R^5$ together represent methylenedioxy;

and pharmaceutically acceptable derivatives thereof. Methods of treatment of neoplastic and autoimmune diseases with these compounds are also disclosed.

60 Claims, 19 Drawing Sheets

(51) Int. Cl.
   G01N 33/50      (2006.01)
   A61K 31/4439    (2006.01)
   C12Q 1/68       (2018.01)

(52) U.S. Cl.
   CPC ....... *C12Q 1/6886* (2013.01); *G01N 33/5011* (2013.01); *G01N 33/5026* (2013.01); *G01N 33/57496* (2013.01); *C12Q 2600/158* (2013.01); *G01N 2333/91205* (2013.01); *G01N 2800/44* (2013.01); *G01N 2800/52* (2013.01)

(58) Field of Classification Search
   USPC ....... 514/338, 364; 435/7.1, 6.12, 7.92, 6.11
   See application file for complete search history.

(56) References Cited

FOREIGN PATENT DOCUMENTS

WO    2005020794 A2    3/2005
WO    2006062811 A2    6/2006
WO    2011012577 A1    2/2011

OTHER PUBLICATIONS

The European Search Report, dated May 10, 2011, in the related European Patent Application No. 11151677.9.

The European Communications, dated Jun. 24, 2014, Nov. 11, 2014 and Apr. 8, 2015, respectively, in the related European Patent Application No. 12701341.5.

Janssen et al., "Elevating the frequency of chromosome mis-segregation as a strategy to kill tumor cells," PNAS, vol. 106, No. 45, Nov. 10, 2009, pp. 19108-19113.

McGrogan et al., "Taxanes, microtubules and chemoresistant breast cancer," Biochim Biophys Acta, vol. 1785, Nov. 12, 2007, pp. 96-132.

Chabalier et al., "BRCA1 downregulation leads to premature inactivation of spindle checkpoint and confers paclitaxel resistance," Cell Cycle, vol. 5, No. 9, May 1, 2006, pp. 1001-1007.

Swanton et al., "Chromosomal Instability, Colorectal Cancer and Taxane Resistance," Cell Cycle, vol. 5, No. 8, pp. 818-823, Apr. 15, 2006, pp. 818-823.

Chia-Ping Huang Yang et al., "The interaction between mitotic checkpoint proteins, CENP-E and BubR1, is diminished in epothilone B-resistant A549 cells," Cell Cycle, vol. 9, No. 6, Mar. 15, 2010, pp. 1207-1213.

Lee et al., "Inactivation of the mitotic checkpoint as a determinant of the efficacy of microtubule-targeted drugs in killing human cancer cells," Molecular Cancer Therapeutics, vol. 3, No. 6, Jun. 2004, pp. 661-669.

Bachmann et al., "BAL27862: A Novel Anticancer Agent that Dissociates Microtubules and Creates a Distinct Cellular Phenotyp," EORTC-NCI-AACR Sympostium 2009, Abstract No. C229, Poster.

Zachos et al., "Chk1 Is Required for Spindle Checkpoint Function," Developmental Cell, vol. 12, Feb. 2007, pp. 247-260.

Greene et al., "BubR1 Is Required for a Sustained Mitotic Spindle Checkpoint Arrest in Human Cancer Cells Treated with Tubulin-Targeting Pyrrolo-1,5-Benzoxazepines," Molecular Pharmacology, vol. 73, No. 2, Feb. 2008, pp. 419-430.

Pohlmann et al., "BAL27862: A novel oral tubulin interacting agent that overcomes the Pgp-related multidrug resistance phenotype in vitro and in vivo," AACR Annual Meeting Apr. 14-18, 2007, Abstract 1428.

Sudo et al., "Dependence of Paclitaxel Sensitivity on a Functional Spindle Assembly Checkpoint", Cancer Research, vol. 64, Apr. 1, 2004, pp. 2502-2508.

Inoue et al., "SIRT2 downregulation confers resistance to microtubule inhibitors by prolonging chronic mitotic arrest," Cell Cycle, vol. 8, No. 8, Apr. 15, 2009, pp. 1279-1291.

Singh et al., "Synuclein-γ Targeting Peptide Inhibitor that Enhances Sensitivity of Breast Cancer Cells to Antimicrotubule Drugs," Cancer Research, vol. 67, No. 2, Jan. 15, 2007, pp. 626-633.

Fu et al., "Weakened spindle checkpoint with reduced BubR1 expression in paclitaxel-resistant ovarian carcinoma cell line SKOV3-TR30," Gynecologic Oncology, vol. 105, Jan. 17, 2007, pp. 66-73.

Duran et al., "In vitro activity of the novel tubulin active agent BAL27862 in MDR1(+) and MDR1(-) human breast and Ovarian cancer variants selected for resistance to taxanes," AACR 101st meeting, Apr. 17-21 2010, Poster.

Office Actions, dated Mar. 13, 2014, Feb. 11, 2015, Aug. 11, 2015, Dec. 4, 2015, Apr. 18, 2016, Oct. 18, 2016, Mar. 14, 2017, Aug. 10, 2017 and Sep. 18, 2017, respectively, in the related U.S. Appl. No. 13/980,180.

Ando et al., "High expression of BUBR1 is one of the factors for inducing DNA aneuploidy and progression in gastric cancer," Cancer Sci. Mar. 2010;101(3):639-45.

Ludwig et al., "Androgen, progesterone, and FSH receptor polymorphisms in ovarian cancer risk and outcome," Endocr Relat Cancer. Sep. 2009;16(3):1005-16.

Bolanos-Garcia et al., "BUB1 and BUBR1: multifaceted kinases of the cell cycle," Trends in Biochemical Sciences vol. 36, Issue 3, Mar. 2011, pp. 141-150.

The International Search Report and Written Opinion, dated May 22, 2012, in the related PCT Appl. No. PCT/EP12/50818.

Esteve et al., "BAL27862: A unique microtubule-targeted drug that suppresses microtubule dynamics, severs microtubules, and overcomes Bcl-2- and tubulin subtype-related drug resistance," Proceedings: AACR 101st Annual Meeting 2010—Apr. 17-21, 2010; Washington, DC.

Duran et al., "In vitro activity of the novel tubulin active agent BAL27862 in MDR1(+) and MDR1(-) human breast and ovarian cancer variants selected for resistance to taxanes," Proceedings: AACR 101st Annual Meeting 2010—Apr. 21, 2010; Washington, DC.

\* cited by examiner

BUBR1 protein sequence [Homo sapiens](SEQ. ID. NO. 1)

```
   1 maavkkegga lseamslegd ewelskenvq plrqgrimst lqgalaqesa cnntlqqqkr
  61 afeyeirfyt gndpldvwdr yiswteqnyp qggkesnmst lleravealq gekryysdpr
 121 flnlwlklgr lcnepldmys ylhnqgigvs laqfyiswae eyearenfrk adaifqegiq
 181 qkaeplerlq sqhrqfqarv srqtllalek eeeeevfess vpqrstlael kskgkktara
 241 piirvggalk apsqnrglqn pfpqqmqnns ritvfdenad eastaelskp tvqpwiappm
 301 prakenelqa gpwntgrsle hrprgntasl iavpavlpsf tpyveetaqq pvmtpckiep
 361 sinhilstrk pgkeegdplq rvqshqqase ekkekmmyck ekiyagvgef sfeeiraevf
 421 rkklkeqrea elltsaekra emqkqieeme kklkeiqttq qertgdqqee tmptkettkl
 481 qiasesqkip gmtlsssvcq vnccaretsl aeniwqeqph skgpsvpfsi fdefllsekk
 541 nksppadppr vlaqrrplav lktsesitsn edvspdvcde ftgieplsed aiitgfrnvt
 601 icpnpedtcd faraarfvst pfheimslkd lpsdperllp eedldvktse dqqtacgtiy
 661 sqtlsikkls piiedsreat hssgfsgssa svastssikc lqipekllelt netsenptqs
 721 pwcsqyrrql lkslpelsas aelciedrpm pkleiekeie lgnedycikr eylicedykl
 781 fwvaprnsae ltvikvssqp vpwdfyinlk lkerlnedfd hfcscyqyqd gcivwhqyin
 841 cftlqdllqh seyitheitv liiynlltiv emlhkaeivh gdlsprclil rnrihdpydc
 901 nknnqalkiv dfsysvdlrv qldvftlsgf rtvqilegqk ilancsspyq vdlfgiadla
 961 hlllfkehlq vfwdgsfwkl sqniselkdg elwnkffvri lnandeatvs vlgelaaemn
1021 gvfdttfqsh lnkalwkvgk ltspgallfq
```

Figure 19

BUBR1 Nucleic acid sequence [Homo sapiens](SEQ. ID. NO. 2)

```
   1 aggggcgtgg ccacgtcgac cgcgcgggac cgttaaattt gaaacttggc ggctagcggt
  61 gtgggcttga ggtggccggt ttgttaggga gtcgtgtacg tgccttggtc gcttctgtag
 121 ctccgagggc aggttgcgga agaaagccca ggcggtctgt ggcccagagg aaaggcctgc
 181 agcaggacga ggacctgagc caggaatgca ggatggcggc ggtgaagaag gaaggggtg
 241 ctctgagtga agccatgtcc ctggagggag atgaatggga actgagtaaa gaaaatgtac
 301 aacctttaag gcaagggcgg atcatgtcca cgcttcaggg agcactggca caagaatctg
 361 cctgtaacaa tactcttcag cagcagaaac gggcatttga atatgaaatt cgattttaca
 421 ctggaaatga ccctctggat gtttgggata ggtatatcag ctggacagag cagaactatc
 481 ctcaaggtgg gaaggagagt aatatgtcaa cgttattaga aagagctgta gaagcactac
 541 aaggagaaaa acgatattat agtgatcctc gatttctcaa tctctggctt aaattagggc
 601 gtttatgcaa tgagcctttg gatatgtaca gttacttgca caccaaggg attggtgttt
 661 cacttgctca gttctatatc tcatgggcag aagaatatga agctagagaa aactttagga
 721 aagcagatgc gatatttcag gaagggattc aacagaaggc tgaaccacta gaaagactac
 781 agtcccagca ccgacaattc caagctcgag tgtctcggca aactctgttg gcacttgaga
 841 aagaagaaga ggaggaagtt tttgagtctt ctgtaccaca acgaagcaca ctagctgaac
 901 taaagagcaa agggaaaaag acagcaagag ctccaatcat ccgtgtagga ggtgctctca
 961 aggctccaag ccagaacaga ggactccaaa atccatttcc tcaacagatg caaaataata
1021 gtagaattac tgttttgat gaaaatgctg atgaggcttc tacagcagag ttgtctaagc
1081 ctacagtcca gccatggata gcacccccca tgcccagggc caaagagaat gagctgcaag
1141 caggcccttg gaacacaggc aggtccttgg aacacaggcc tcgtggcaat acagcttcac
1201 tgatagctgt accgctgtg cttcccagtt tcactccata tgtggaagag actgcacaac
1261 agccagttat gacaccatgt aaaattgaac ctagtataaa ccacatccta agcaccagaa
1321 agcctggaaa ggaagaagga gatcctctac aaagggttca gagccatcag caagcgtctg
1381 aggagaagaa agagaagatg atgtattgta aggagaagat ttatgcagga gtaggggaat
1441 tctccttga agaaattcgg gctgaagttt tccggaagaa attaaagag caaagggaag
1501 ccgagctatt gaccagtgca gagaagagag cagaaatgca gaaacagatt gaagagatgg
1561 agaagaagct aaaagaaatc caaactactc agcaagaaag aacaggtgat cagcaagaag
1621 agacgatgcc tacaaaggag acaactaaac tgcaaattgc ttccgagtct cagaaaatac
1681 caggaatgac tctatccagt tctgtttgtc aagtaaactg ttgtgccaga gaaacttcac
1741 ttgcggagaa catttggcag gaacaacctc attctaaagg tccagtgta cctttctcca
1801 tttttgatga gtttcttctt tcagaaaaga gaataaaag tcctcctgca gatccccac
1861 gagttttagc tcaacgaaga cccttgcag ttctcaaaac ctcagaaagc atcacctcaa
1921 atgaagatgt gtctccagat gtttgtgatg aatttacagg aattgaaccc ttgagcgagg
1981 atgccattat cacaggcttc agaaatgtaa caatttgtcc taacccagaa gacacttgtg
2041 actttgccag agcagctcgt tttgtatcca ctcctttta tgagataatg tccttgaagg
2101 atctcccttc tgatcctgag agactgttac cggaagaaga tctagatgta aagacctctg
2161 aggaccagca gacagcttgt ggcactatct acagtcagac tctcagcatc aagaagctga
2221 gcccaattat tgaagacagt cgtgaagcca cacactcctc tggcttctct ggttcttctg
```

Figure 20

```
2281 cctcggttgc aagcacctcc tccatcaaat gtcttcaaat tcctgagaaa ctagaactta
2341 ctaatgagac ttcagaaaac cctactcagt caccatggtg ttcacagtat cgcagacagc
2401 tactgaagtc cctaccagag ttaagtgcct ctgcagagtt gtgtatagaa gacagaccaa
2461 tgcctaagtt ggaaattgag aaggaaattg aattaggtaa tgaggattac tgcattaaac
2521 gagaatacct aatatgtgaa gattacaagt tattctgggt ggcgccaaga aactctgcag
2581 aattaacagt aataaaggta tcttctcaac ctgtcccatg ggactttat atcaacctca
2641 agttaaagga acgtttaaat gaagattttg atcattttg cagctgttat caatatcaag
2701 atggctgtat tgtttggcac caatatataa actgcttcac ccttcaggat cttctccaac
2761 acagtgaata tattacccat gaaataacag tgttgattat ttataacctt ttgacaatag
2821 tggagatgct acacaaagca gaaatagtcc atggtgactt gagtccaagg tgtctgattc
2881 tcagaaacag aatccacgat ccctatgatt gtaacaagaa caatcaagct ttgaagatag
2941 tggactttc ctacagtgtt gaccttaggg tgcagctgga tgttttacc ctcagcggct
3001 ttcggactgt acagatcctg gaaggacaaa agatcctggc taactgttct tctccctacc
3061 aggtagacct gtttggtata gcagatttag cacatttact attgttcaag gaacacctac
3121 aggtcttctg ggatgggtcc ttctggaaac ttagccaaaa tatttctgag ctaaaagatg
3181 gtgaattgtg gaataaattc tttgtgcgga ttctgaatgc caatgatgag gccacagtgt
3241 ctgttcttgg ggagcttgca gcagaaatga atggggtttt tgacactaca ttccaaagtc
3301 acctgaacaa agccttatgg aaggtaggga agttaactag tcctggggct ttgctctttc
3361 agtgagctag gcaatcaagt ctcacagatt gctgcctcag agcaatggtt gtattgtgga
3421 acactgaaac tgtatgtgct gtaatttaat ttaggacaca tttagatgca ctaccattgc
3481 tgttctactt tttggtacag gtatattttg acgtcactga tattttttat acagtgatat
3541 acttactcat ggccttgtct aactttttgtg aagaactatt ttattctaaa cagactcatt
3601 acaaatggtt accttgttat ttaacccatt tgtctctact tttccctgta cttttcccat
3661 ttgtaatttg taaaatgttc tcttatgatc accatgtatt ttgtaaataa taaaatagta
3721 tctgttaaat ttgtgcttct aaaaaaaaa
```

USE OF BUBR1 AS A BIOMARKER OF DRUG RESPONSE TO FURAZANOBENZIMIDAZOLES

This application is a divisional of U.S. application Ser. No. 13/980,180, filed Oct. 14, 2013, now pending; which in turn is a National Stage of International Application No. PCT/EP2012/050818, filed Jan. 19, 2012. The entire contents of the above-identified applications are hereby incorporated by reference.

The present invention relates to use of BUBR1 as a biomarker for predicting the response of a disease, such as a neoplastic or autoimmune disease, preferably cancer, to a compound of general formula I, such as 3-(4-{1-[2-(4-amino-phenyl)-2-oxo-ethyl]-1H-benzoimidazol-2-yl}-furazan-3-ylamino)-propionitrile (BAL27862). In other aspects it relates to methods and kits, as well as methods of treatment involving the use of the biomarker.

Microtubules are one of the components of the cell cytoskeleton and are composed of heterodimers of alpha and beta tubulin. Agents that target microtubules are among the most effective cytotoxic chemotherapeutic agents having a broad spectrum of activity. Microtubule destabilising agents (e.g. the vinca-alkaloids such as vincristine, vinblastine and vinorelbine) are used for example in the treatment of several types of hematologic malignancies, such as lymphoblastic leukaemia and lymphoma, as well as solid tumours, such as lung cancer. Microtubule stabilising agents (e.g. the taxanes such as paclitaxel, docetaxel) are used for example in the treatment of solid tumours, including breast, lung and prostate cancer.

However resistance to these known microtubule targeting agents can occur. The resistance can either be inherent or can be acquired after exposure to these agents. Such resistance therefore impacts patient survival rates, as well as choices of treatment regimes. Several potential mechanisms of resistance have been identified, and include defects in the microtubule targets, such as elevated levels of beta-tubulin subtype III and acquired mutations in beta-tubulin subtype I that are known to reduce taxane binding. Furthermore, defects in other cell proteins have been suggested to be associated with resistance to certain microtubule targeting agents, such as overexpression of p-glycoprotein (P-gp pump, also known as multi-drug resistance protein 1 or MDR1). Such factors may then be used as biomarkers of resistance to these conventional microtubule targeting agents.

A relatively recently discovered class of microtubule destabilising agents are compounds encompassed by the formula given below:

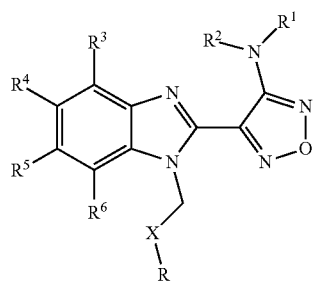

(I)

wherein
R represents phenyl, thienyl or pyridinyl
wherein phenyl is optionally substituted by one or two substituents independently selected from alkyl, halo-lower alkyl, hydroxy-lower alkyl, lower alkoxy-lower alkyl, acyloxy-lower alkyl, phenyl, hydroxy, lower alkoxy, hydroxy-lower alkoxy, lower alkoxy-lower alkoxy, phenyl-lower alkoxy, lower alkylcarbonyloxy, amino, monoalkylamino, dialkylamino, lower alkoxycarbonylamino, lower alkylcarbonylamino, substituted amino wherein the two substituents on nitrogen form together with the nitrogen heterocyclyl, lower alkylcarbonyl, carboxy, lower alkoxycarbonyl, cyano, halogen, and nitro; and wherein two adjacent substituents are methylenedioxy;
and wherein pyridinyl is optionally substituted by lower alkoxy, amino or halogen;
X represents a group C=Y, wherein Y stands for oxygen or nitrogen substituted by hydroxy or lower alkoxy;
$R^1$ represents hydrogen, lower alkylcarbonyl, hydroxy-lower alkyl or cyano-lower alkyl;
$R^2$, $R^3$ and $R^6$ represent hydrogen;
$R^4$ and $R^5$, independently of each other, represent hydrogen, lower alkyl or lower alkoxy;
or $R^4$ and $R^5$ together represent methylenedioxy;
and pharmaceutically acceptable salts thereof;
or wherein
R represents phenyl or pyridinyl
wherein phenyl is optionally substituted by one or two substituents independently selected from alkyl, halo-lower alkyl, hydroxy-lower alkyl, lower alkoxy-lower alkyl, acyloxy-lower alkyl, phenyl, hydroxy, lower alkoxy, hydroxy-lower alkoxy, lower alkoxy-lower alkoxy, phenyl-lower alkoxy, lower alkylcarbonyloxy, amino, monoalkylamino, dialkylamino, lower alkoxycarbonylamino, lower alkylcarbonylamino, substituted amino wherein the two substituents on nitrogen form together with the nitrogen heterocyclyl, lower alkylcarbonyl, carboxy, lower alkoxycarbonyl, formyl, cyano, halogen, and nitro; and wherein two adjacent substituents are methylenedioxy;
and wherein pyridinyl is optionally substituted by lower alkoxy, amino or halogen;
X represents oxygen;
$R^1$ represents hydrogen, lower alkylcarbonyl, hydroxy-lower alkyl or cyano-lower alkyl;
$R^2$, $R^3$ and $R^6$ represent hydrogen;
$R^4$ and $R^5$, independently of each other, represent hydrogen, lower alkyl or lower alkoxy;
or $R^4$ and $R^5$ together represent methylenedioxy;
and pharmaceutically acceptable salts thereof;
and wherein the prefix lower denotes a radical having up to and including a maximum of 7, especially up to and including a maximum of 4 carbon atoms.

These compounds are disclosed in WO2004/103994 A1, which is incorporated by cross-reference herein. These compounds have been shown to arrest tumour cell proliferation and induce apoptosis.

The synthesis of compounds of formula I is described in WO2004/103994 A1, in general on pages 29-35, and specifically on pages 39-55, which are incorporated herein by cross-reference. They may be prepared as disclosed or by an analogous method to the processes described therein.

One compound falling within this class, known as BAL27862, and shown in WO2004/103994 A1 as example 58, and specifically incorporated by reference herein, has the structure and chemical name given below:

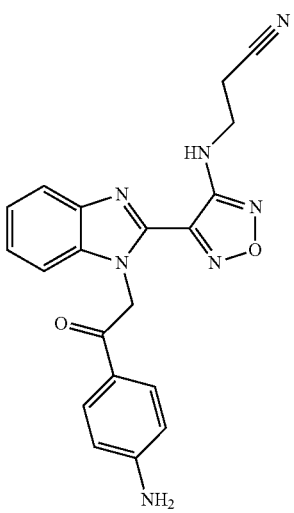 [SMILES: N#CCCNc1nonc1-c1nc2ccccc2n1CC(=O)c1ccc(N)cc1]

Chemical Name: 3-(4-{1-[2-(4-Amino-phenyl)-2-oxo-ethyl]-1H-benzoimidazol-2-yl}-furazan-3-ylamino)-propionitrile.

Or herein as Compound A

Further compounds exemplified in WO2004/103994 A1 as examples 50 and 79 respectively, and also specifically incorporated by cross-reference herein, have the structures and chemical names given below:

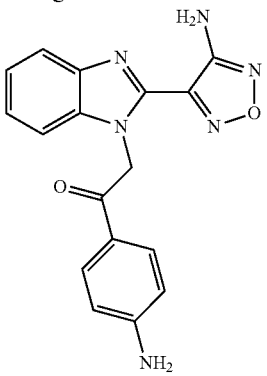

Chemical name: 2-[2-(4-Amino-furazan-3-yl)-benzoimidazol-1-yl]-1-(4-amino-phenyl)-ethanone or herein as Compound B
and

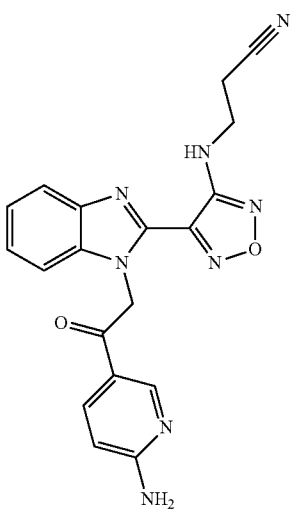 [SMILES: N#CCCNc1nonc1-c1nc2ccccc2n1CC(=O)c1ccc(N)nc1]

Chemical name: 3-(4-{1-[2-(6-Amino-pyridin-3-yl)-2-oxo-ethyl]-1H-benzoimidazol-2-yl}-furazan-3-ylamino)-propionitrile or herein as Compound C.

BAL27862 has demonstrated activity across a broad panel of experimental, solid tumour xenograft models. Moreover, activity was retained even against tumour models which were selected for resistance to conventional microtubule targeting agents (including the vinca-alkaloid microtubule destabilisers and the microtubule stabilisers paclitaxel and epothilone B). BAL27862 activity was not affected by over-expression of the P-gp pump in any models tested in vitro, nor in human mammary tumour xenografts. Additionally, BAL27862 retained its activity despite elevated levels of beta-tubulin subtype III and mutations in tubulin subtype I.

Hence, BAL27862 activity is not affected by a number of factors that confer resistance to conventional microtubule targeting agents.

Moreover, it is known that compounds of general formula I have a different effect on the phenotype of cells compared to other microtubule targeting agents, including other microtubule destabilisers. Treatment with a compound of general formula I induces a consistent microtubule phenotype in tumour cell lines derived from a variety of organs, for example lung, cervix and breast, as seen in FIG. 1. Staining the microtubules in these cells with an anti-alpha-tubulin antibody shows that rather than the mitotic spindle fibres of untreated cells, only dot-like structures are visible in the treated cells. This same effect is also shown using Compounds C and B in FIG. 2, A and B respectively on the lung cancer cell line A549. It is however very distinct from that observed with the conventional microtubule targeting agents vinblastine, colchicine, paclitaxel and nocodazole as seen in FIGS. 3, (B, C, D) and 4, respectively. The microtubules were stained with an anti-alpha-tubulin antibody and the cells viewed at a 1000× magnification (FIGS. 3, 4). For the cells treated with BAL27862, multiple dot-like structures are visible, whereas, in stark contrast, the other conventional drugs produce filamentous microtubule structures, or dense microtubule aggregate structures. These differences at the phenotypic level, at compound doses considered optimal in terms of antiproliferative effect, indicate a difference in the mode of action at the molecular level.

Furthermore, it is known that BAL27862 elicits a dominant microtubule phenotype in the presence of the other microtubule targeting agents. Treatment with vinblastine, colchicine, paclitaxel or nocodazole alone induced the microtubule phenotypes characteristic of these agents (FIG. 5, A, D, G, C-F respectively). However, combination treatment with BAL27862 for the last 4 hours resulted in disruption of these phenotypes; despite the continued presence of vinblastine, colchicine, paclitaxel, or nocodazole (FIG. 5, B, E, H, J respectively). In contrast, treating first with BAL27862 and subsequently for 4 hours in combination with vinblastine, colchicine, paclitaxel or nocodazole had no impact on generation of the phenotype consistent with BAL27862 treatment (FIG. 5, C, F, I, K-N respectively).

These data all demonstrate that BAL27862 affects microtubule biology in a different manner than conventional microtubule targeting agents.

Thus, from information about conventional microtubule targeting agents, predictions cannot be made concerning if, or how, particular genes are involved in the action of compounds of formula I.

An object of the present invention is to identify factors which are associated with response to compounds of formula I or pharmaceutically acceptable derivatives thereof, for example to identify factors associated with resistance to compounds of general formula I, in particular BAL27862 or pharmaceutically acceptable derivatives thereof, as defined below.

It has surprisingly been found that BUBR1 may be used as a biomarker of response to treatment with a compound of general formula I or pharmaceutically acceptable derivatives thereof, as defined below.

In one preferred embodiment of the invention, relatively low BUBR1 levels in a sample are associated with inherent and acquired resistance to BAL27862, as described below.

BUBR1 has been assigned Human Gene Nomenclature Committee Identification number HGNC ID:1149 and Entrez Gene ID 701. A sequence corresponding to human BUBR1 is available via National Center for Biotechnology Information (NCBI) reference number NP_001202 (FIG. 18, SEQ ID No. 1, NP_001202.4).

BUBR1 is also known as hBUBR1 and BubR1; Budding uninhibited by benzimidazoles 1, *S. cerevisiae*, homolog, beta; mitotic checkpoint gene BUB1B; BUB1B; BUB1 beta; mitotic checkpoint kinase Mad3L; MAD3L; MAD3-like protein kinase; and SSK1. The name BUB1B is commonly associated with the nucleic acid sequence, while publications focusing on the protein have commonly used the term BUBR1. For simplicity, the term BUBR1 shall be used herein to encompass all the above mentioned synonyms and shall refer to this entity on both the nucleic acid and protein levels as appropriate.

The name budding uninhibited by benzimidazoles was assigned to the yeast homolog by Hoyt et al. after experiments conducted with benomyl. (Hoyt M A. et al., *S. Cerevisiae* Genes Required for Cell Cycle Arrest in Response to Loss of Microtubule Function. Cell, Vol. 66, 507-517, Aug. 9, 1991) This publication describes mutations in the bub yeast homolog that resulted in hypersensitivity to benomyl.

The human homologue is located on chromosome 15q15. The sequence of the human BUBR1 gene was published in U.S. Pat. No. 6,593,098 B1 and is identified therein as human BUB1A. Example VI of that patent describes an experiment performed in HeLa cells, wherein the activity of endogenous BUB1A (BUBR1) was inhibited by microinjection of anti-huBUB1A antibodies. The injected cells were then tested for their ability to remain arrested in mitosis when exposed to nocadozole, a microtubule destabiliser. The patent states that the cells injected with huBUB1a antibodies failed to arrest in mitosis in the presence of nocodazole and proceeded to undergo apoptosis as a result of premature exit from mitosis.

Similarly to the Hoyt publication, this suggests that loss of BUBR1 function in cells which are then treated with nocodazole results in a heightened rate of apoptosis.

However, in contrast, the present inventors have found that loss of BUBR1 expression is associated with lowered levels of cell death in response to compounds of general formula I, i.e. resistance to these compounds. It is again to be emphasized that compounds of formula I have a different effect on the phenotype of cells compared to other microtubule agents, including other microtubule destabilisers, as seen in FIGS. 3, 4, 5 and 6. The discrepancy between the findings of, on the one side U.S. Pat. No. 6,593,098 B1 and Hoyt, and on the other side, the present inventors, confirms that predictions from information concerning conventional microtubule agents cannot be made concerning if, or how, particular genes are involved in the activity of compounds of general formula I.

One aspect of the present invention relates to use of BUBR1 as a biomarker for predicting the response to a compound, wherein the compound is a compound of general formula I

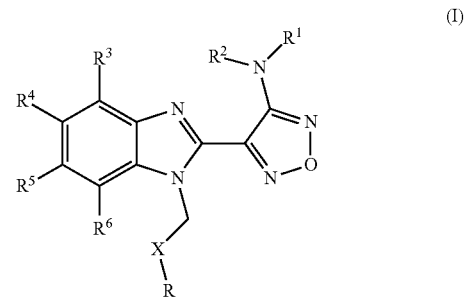

wherein

R represents phenyl, thienyl or pyridinyl wherein phenyl is optionally substituted by one or two substituents independently selected from alkyl, halo-lower alkyl, hydroxy-lower alkyl, lower alkoxy-lower alkyl, acyloxy-lower alkyl, phenyl, hydroxy, lower alkoxy, hydroxy-lower alkoxy, lower alkoxy-lower alkoxy, phenyl-lower alkoxy, lower alkylcarbonyloxy, amino, monoalkylamino, dialkylamino, lower alkoxycarbonylamino, lower alkylcarbonylamino, substituted amino wherein the two substituents on nitrogen form together with the nitrogen heterocyclyl, lower alkylcarbonyl, carboxy, lower alkoxycarbonyl, cyano, halogen, and nitro; and wherein two adjacent substituents are methylenedioxy;

and wherein pyridinyl is optionally substituted by lower alkoxy, amino or halogen;

X represents a group C=Y, wherein Y stands for oxygen or nitrogen substituted by hydroxy or lower alkoxy;

$R^1$ represents hydrogen, lower alkylcarbonyl, hydroxy-lower alkyl or cyano-lower alkyl;

$R^2$, $R^3$ and $R^6$ represent hydrogen;

$R^4$ and $R^5$, independently of each other, represent hydrogen, lower alkyl or lower alkoxy;

or $R^4$ and $R^5$ together represent methylenedioxy;

and pharmaceutically acceptable derivatives thereof, or wherein

R represents phenyl or pyridinyl wherein phenyl is optionally substituted by one or two substituents independently selected from alkyl, halo-lower alkyl, hydroxy-lower alkyl, lower alkoxy-lower alkyl, acyloxy-lower alkyl, phenyl, hydroxy, lower alkoxy, hydroxy-lower alkoxy, lower alkoxy-lower alkoxy, phenyl-lower alkoxy, lower alkylcarbonyloxy, amino, monoalkylamino, dialkylamino, lower alkoxycarbonylamino, lower alkylcarbonylamino, substituted amino wherein the two substituents on nitrogen form together with the nitrogen heterocyclyl, lower alkylcarbonyl, carboxy, lower alkoxycarbonyl, formyl, cyano, halogen, and nitro; and wherein two adjacent substituents are methylenedioxy;

and wherein pyridinyl is optionally substituted by lower alkoxy, amino or halogen;

X represents oxygen;

$R^1$ represents hydrogen, lower alkylcarbonyl, hydroxy-lower alkyl or cyano-lower alkyl;

$R^2$, $R^3$ and $R^6$ represent hydrogen;

$R^4$ and $R^5$, independently of each other, represent hydrogen, lower alkyl or lower alkoxy;

or $R^4$ and $R^5$ together represent methylenedioxy;

and pharmaceutically acceptable derivatives thereof;

and wherein the prefix lower denotes a radical having up to and including a maximum of 7, especially up to and including a maximum of 4 carbon atoms.

Preferably the response may be of a disease in a subject. Also preferably the response may be to treatment, i.e. to treatment with the compound of general formula I or pharmaceutically acceptable derivatives thereof.

The biomarker BUBR1 is measured ex vivo in a sample or samples taken from the human or animal body, preferably taken from the human body.

In a preferred embodiment, the invention relates to use of BUBR1 as a biomarker for predicting the resistance of a disease in a subject to a compound of general formula I or pharmaceutically acceptable derivatives thereof as defined above.

Preferably the pharmaceutically acceptable derivative is selected from the group consisting of a salt, solvate, pro-drug, salt of a pro-drug, polymorph and isomer of a compound of general formula I as defined above. Pro-drugs are preferably ester and amides of naturally occurring amino acids, small peptides or pegylated hydroxy acids. More preferably, the pro-drug is an amide formed from an amino group present within the R group of the compound of general formula I and the carboxy group of glycine, alanine or lysine.

Particularly preferably the compound is

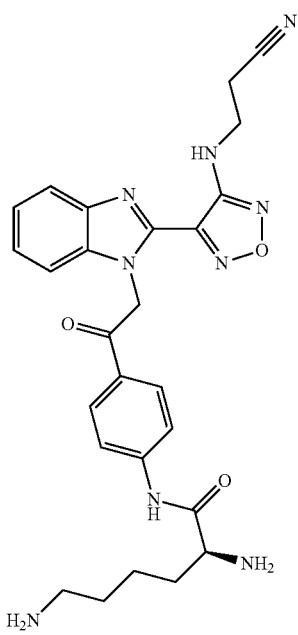 [SMILES: N#CCCNc1nonc1-c1nc2ccccc2n1CC(=O)c1ccc(NC(=O)[C@@H](N)CCCCN)cc1]

or a pharmaceutically acceptable salt thereof, preferably a hydrochloride salt thereof, most preferably a dihydrochloride salt thereof.

Another aspect of the present invention relates to a method for predicting the response of a disease in a subject to a compound of general formula I or pharmaceutically acceptable derivatives thereof as defined above, comprising the steps of:

a) measuring a level of BUBR1 in a sample pre-obtained from the subject to obtain a value or values representing this level; and b) comparing the value or values from step a) to a standard value or set of standard values.

Further preferably the response which is predicted is resistance.

The measuring of a level or levels of BUBR1 is performed ex-vivo in a sample or samples pre-obtained from the subject. Pre-obtained refers to the fact that the sample is obtained before it is subjected to any method involving measuring the level of the biomarker, and pre-obtained is not to be understood as in relation to treatment.

In a preferred embodiment, a lower level of BUBR1 in the sample from the subject relative to the standard value or set of standard values predicts resistance.

Also preferably, the disease is a neoplastic or autoimmune disease. More preferably the disease is cancer. Especially preferably, the cancer is selected from the group consisting of breast cancer, prostate cancer, cervical cancer, ovarian cancer, gastric cancer, colorectal cancer (i.e. including colon cancer and rectal cancer), pancreatic cancer, liver cancer, brain cancer, neuroendocrine cancer, lung cancer, kidney cancer, hematological malignancies, melanoma and sarcomas. More especially preferably the cancer is selected from the group consisting of breast cancer, cervical cancer, ovarian cancer, gastric cancer, pancreatic cancer, colon cancer and lung cancer. More particularly preferably the cancer is selected from the group consisting of cervical cancer, ovarian cancer, gastric cancer, pancreatic cancer, colon cancer and lung cancer. In another particularly preferred embodiment, wherein acquired resistance is determined, the cancer is lung cancer or ovarian cancer. In yet another particularly preferred embodiment, wherein inherent resistance is determined, the cancer is selected from the group consisting of cervical cancer, breast cancer, ovarian cancer, gastric cancer, pancreatic cancer, colon cancer and lung cancer, more preferably lung cancer or gastric cancer.

In a further aspect, the invention relates to a method of treating a neoplastic or autoimmune disease, preferably cancer, in a subject in need thereof, comprising measuring a level of BUBR1 in a sample from the subject to obtain a value or values representing this level, and treating the subject with a compound of general formula I or a pharmaceutically acceptable derivative thereof as defined above, if the level of BUBR1 in said sample is not lower than a standard value or set of standard values.

In yet a further aspect, the invention relates to BUBR1 for use in the treatment of a neoplastic or autoimmune disease, preferably cancer, comprising measuring a level of BUBR1 in a sample from the subject to obtain a value or values representing this level, and treating the subject with a compound of general formula I or a pharmaceutically acceptable derivative thereof as defined above, if the level of BUBR1 is not lower than a standard value or set of standard values.

The measuring of a level of BUBR1 is performed ex-vivo in a sample pre-obtained from the subject.

The invention also relates in another aspect to a method of treating a neoplastic or autoimmune disease, preferably cancer, by first increasing the level of BUBR1 in a subject that has a sample with a lower level of BUBR1 compared to a standard level or set of standard levels, then treating the subject with a compound of general formula I or a pharmaceutically acceptable derivative thereof as defined above.

In yet another aspect the invention relates to a kit for predicting the response to a compound of general formula I or a pharmaceutically acceptable derivative thereof, as defined above, comprising reagents necessary for measuring the level of BUBR1 in a sample. More preferably the kit also comprises a comparator module which comprises a standard value or set of standard values to which the level of BUBR1 in the sample is compared.

Furthermore preferably the kit comprises a compound of general formula I or a pharmaceutically acceptable derivative thereof as defined above. In an especially preferred embodiment the kit comprises a compound of the following formula or a pharmaceutically acceptable salt thereof:

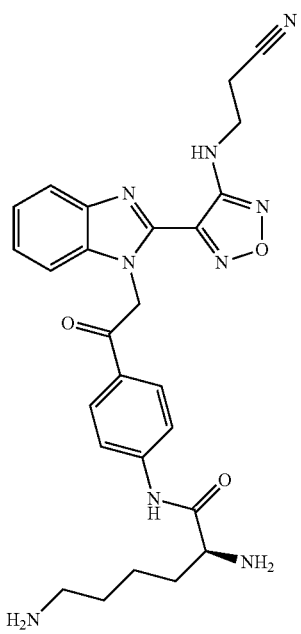

Chemical name: S-2,6-Diamino-hexanoic acid [4-(2-{2-[4-(2-cyano-ethylamino)-furazan-3-yl]-benzoimidazol-1-yl}-acetyl)-phenyl]-amide In a particularly preferred embodiment the pharmaceutically acceptable salt is a dihydrochloride salt.

Another further aspect of the invention relates to a device for predicting the response to a compound of general formula I or a pharmaceutically acceptable derivative thereof as defined above, comprising reagents necessary for measuring the level of BUBR1 in a sample and a comparator module which comprises a standard value or set of standard values to which the level of BUBR1 in the sample is compared.

In a preferred embodiment, the reagents in the kit or device comprise a capture reagent comprising a detector for BUBR1, and a detector reagent. Especially preferably the capture reagent is an antibody. Also preferably, the disease is predicted to be resistant to treatment with said compound when BUBR1 is lower relative to a standard value or set of standard values. In a preferred embodiment, the comparator module is included in instructions for use of the kit. In another preferred embodiment the comparator module is in the form of a display device.

Embodiments of the present invention will now be described by way of example with reference to the accompanying figures. The invention however is not to be understood as limited to these embodiments.

Figure 1:
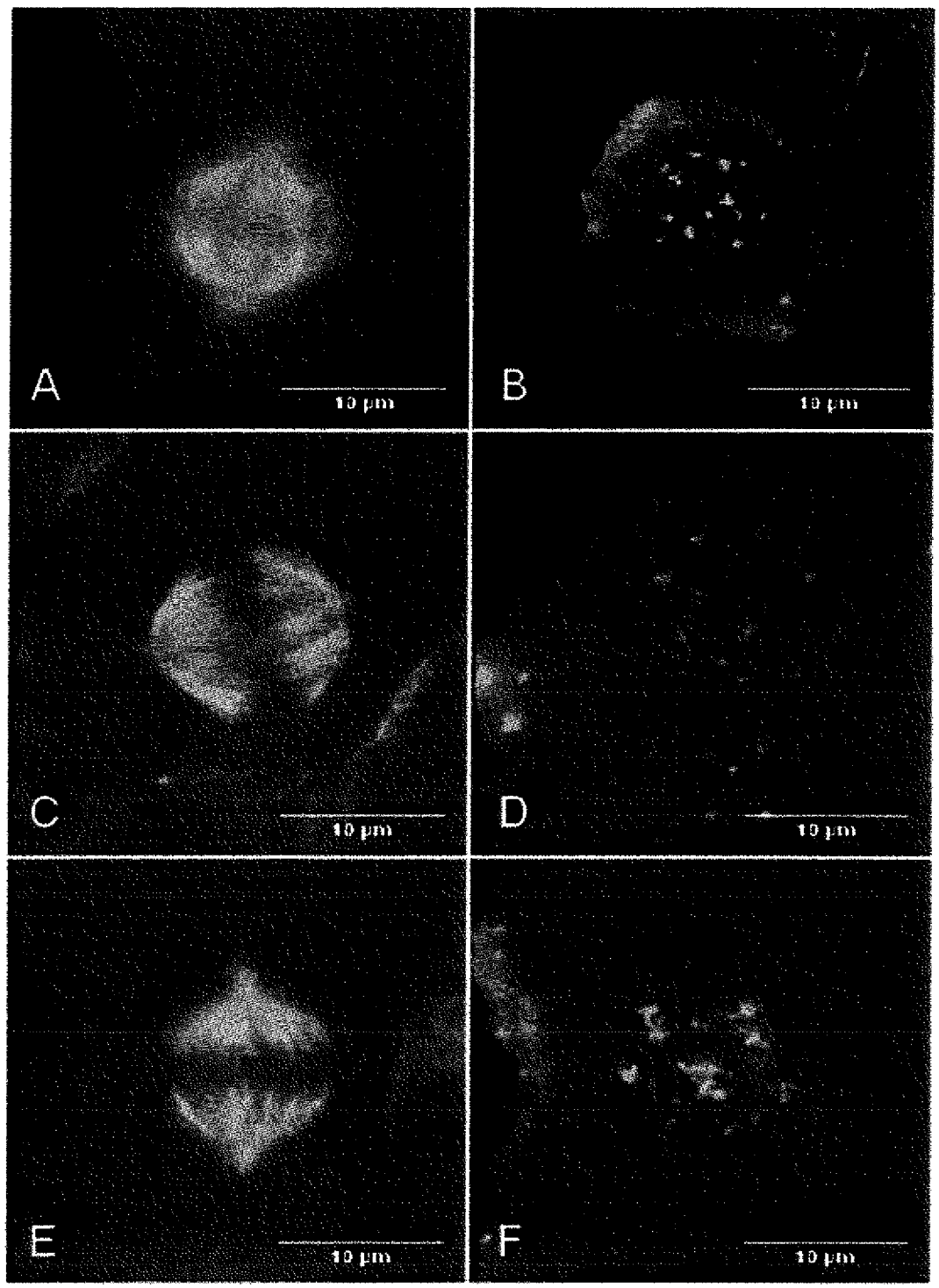
FIG. 1: Shows the treatment of human tumour cell lines from different histotypes with 50 nM BAL27862. The microtubules of mitotic or G2/M arrested cells were stained after 24 hours treatment with 50 nM BAL27862 or vehicle control.
A and B: A549 NSCLC cells;
C and D: HeLa cervical cancer cells;
E and F: SKBR3 breast cancer cells
Vehicle control treatment: A, C & E,
BAL27862 treatment: B, D & F.

A: 24 hours control treatment;
B: 24 hours of 25 nM BAL27862 treatment;
C: 24 hours of 50 nM nocodazole treatment
D: 24 hours of 100 nM nocodazole treatment
E: 24 hours of 150 nM nocodazole treatment
F: 24 hours of 200 nM nocodazole treatment
G: 24 hours of 50 nM nocodazole treatment with the final 4 hours including 25 nM BAL27862;
H: 24 hours of 100 nM nocodazole treatment with the final 4 hours including 25 nM BAL27862;
I: 24 hours of 150 nM nocodazole treatment with the final 4 hours including 25 nM BAL27862;
J: 24 hours of 200 nM nocodazole treatment with the final 4 hours including 25 nM BAL27862;
K: 24 hours of 25 nM BAL27862 treatment with the final 4 hours including 50 nM nocodazole;
L: 24 hours of 25 nM BAL27862 treatment with the final 4 hours including 100 nM nocodazole;
M: 24 hours of 25 nM BAL27862 treatment with the final 4 hours including 150 nM nocodazole;
N: 24 hours of 25 nM BAL27862 treatment with the final 4 hours including 200 nM nocodazole.

Figure 7:
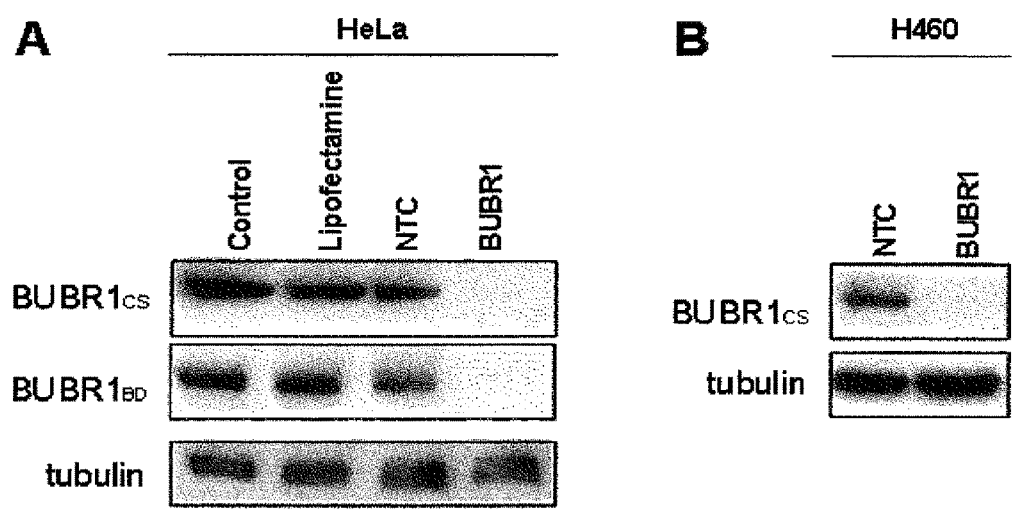

FIG. 7: Shows immunoblot analysis of BUBR1 expression after transfection with a BUBR1 siRNA pool. Control: non-transfected cells treated with medium alone; Lipofectamine: cells treated with transfection reagent alone; NTC: cells treated with non-targeting control siRNA; BUBR1: cells treated with a BUBR1specific siRNA pool. Alpha-tubulin levels act as a loading control. Cell Signaling (CS) or BD Transduction Laboratories (BD) BUBR1 antibodies were used as indicated. A: HeLa cervical cancer cells, B: H460 lung cancer cells FIG. 8: Effect of a BUBR1 siRNA pool on response to BAL27862 in HeLa cells. HeLa cells were seeded and treated with siRNA. After 48 hours incubation, the cells were treated with DMSO alone or 50 nM BAL27862 for 24 hours before analysis. Upper panel: Histogram of the fraction of cells per well (in %) displaying the untreated phenotype. Lower panel: Histogram of the number of cells per well. Error bars: Standard deviation. Negative control: non-targeting control siRNA. BubR1: BUBR1-specific siRNA pool treated cells.

Figure 9:
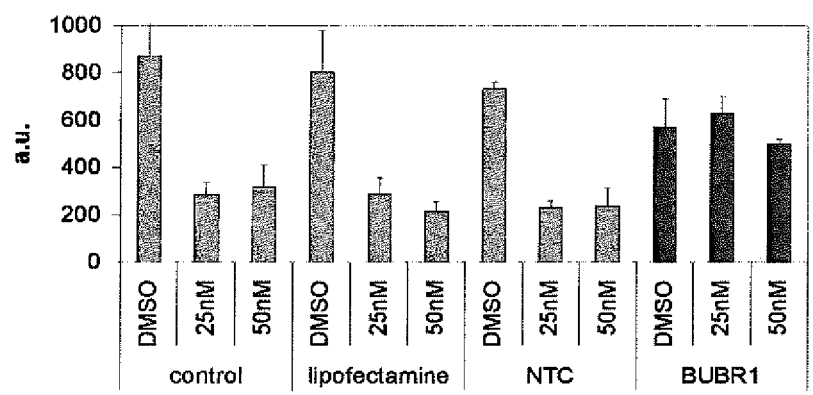
Figure 9:
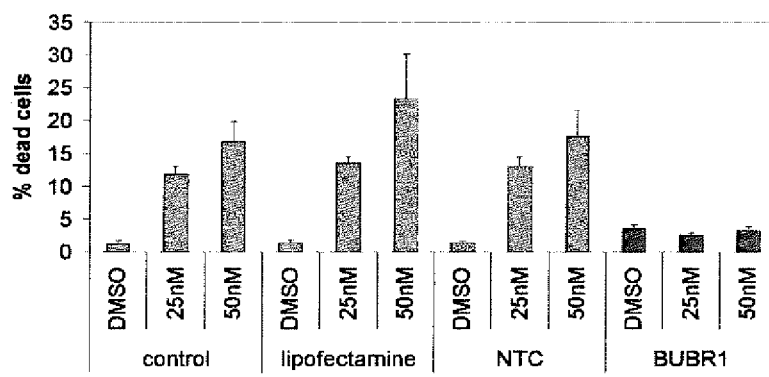
Figure 10:
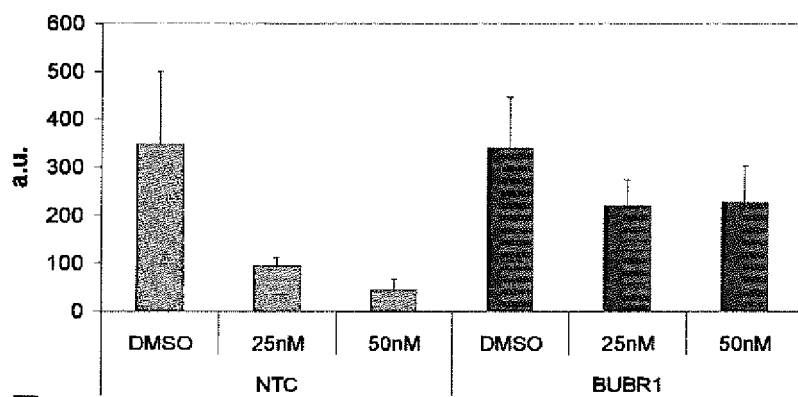
Figure 10:
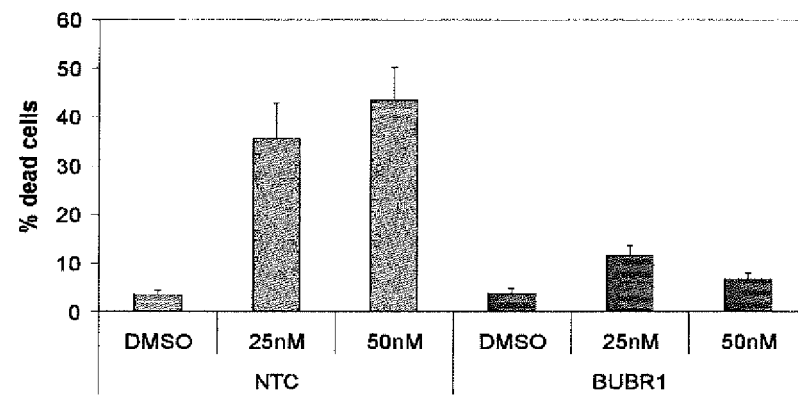

FIG. 9: Shows the effect of a BUBR1 siRNA pool on response of HeLa cells to BAL27862. Exponentially growing HeLa cells were treated with medium alone (control), or transfected with lipofectamine, non-targeting control (NTC) siRNA or a BUBR1-specific siRNA pool. After 24 hours, BAL27862 was added at the indicated concentrations, with DMSO vehicle used as a control. After 48 hours treatment, effects on HeLa cell proliferation (A) and viability (B) were assessed using the YO-PRO proliferation assay. a.u=data is expressed as arbitrary units FIG. 10: Shows the effect of a BUBR1 siRNA pool on response of H460 cells to BAL27862. Exponentially growing H460 cells were transfected with non-targeting control (NTC) siRNA or a BUBR1-specific siRNA pool. After 24 hours, BAL27862 was added at the indicated concentrations, with DMSO vehicle used as a control. After 48 hours treatment, effects on H460 cell proliferation (A) and viability (B) were assessed using the YO-PRO proliferation assay. a.u=data is expressed as arbitrary units FIG. 11: Shows the effect of a BUBR1 siRNA pool on response of MCF-7 cells to BAL27862. Exponentially growing MCF-7 cells were treated with non-targeting control (NTC) siRNA or a BUBR1-specific siRNA pool. After 24 hours, BAL27862 was added at the indicated concentrations, with DMSO vehicle used as a control. After 48 hours treatment, effects on MCF-7 cell proliferation (A) and viability (B) were assessed using the YO-PRO proliferation assay. a.u=data is expressed as arbitrary units FIG. 12: Shows the effect of a BUBR1 siRNA pool on response of HeLa, Panc1 and HCT116 cells to BAL27862. Exponentially growing cells were treated with non-targeting control (NTC) siRNA or a BUBR1-specific siRNA pool. After 24 hours, 50 nM (HeLa, HCT116) or 30 nM (Panc1) BAL27862 was added, with DMSO vehicle used as a control. After 48 hours treatment, effects on HeLa (A), Panc1 (B) and HCT116 (C) cell proliferation were assessed using the Crystal Violet assay. a.u=data is expressed as arbitrary units.

Figure 13:
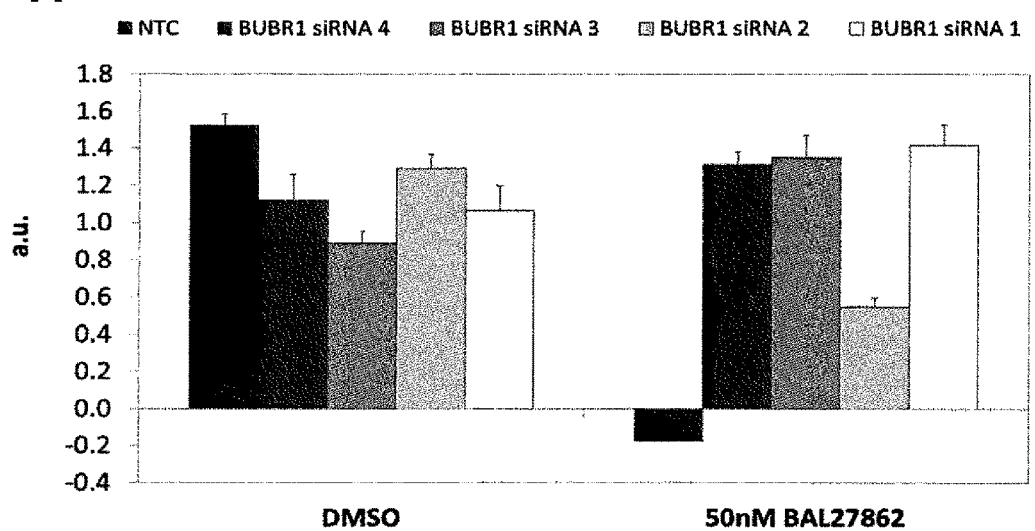
Figure 13:
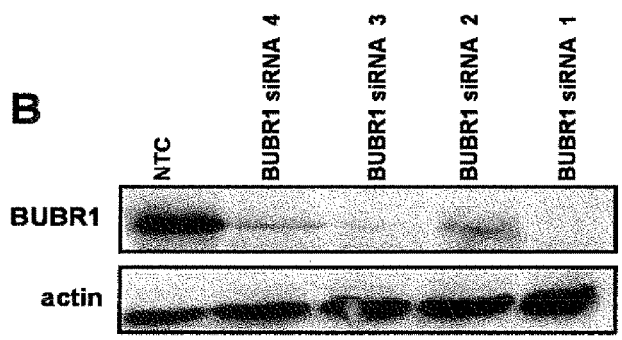

FIG. 13: Shows the effect of individual BUBR1 siRNAs on response of HeLa cells to BAL27862. Exponentially growing cells were treated with non-targeting control (NTC) siRNA or individual BUBR1-specific siRNAs (siRNA #1, 2, 3 and 4, as defined in the experimental methodology section below). After 24 hours, 50 nM BAL27862 was added, with DMSO vehicle used as a control. After 48 hours treatment, effects on HeLa cell proliferation (A) were assessed using the Crystal Violet assay and effects on BUBR1 protein expression were assessed by immunoblotting (B). a.u=data is expressed as arbitrary units.

Figure 14:
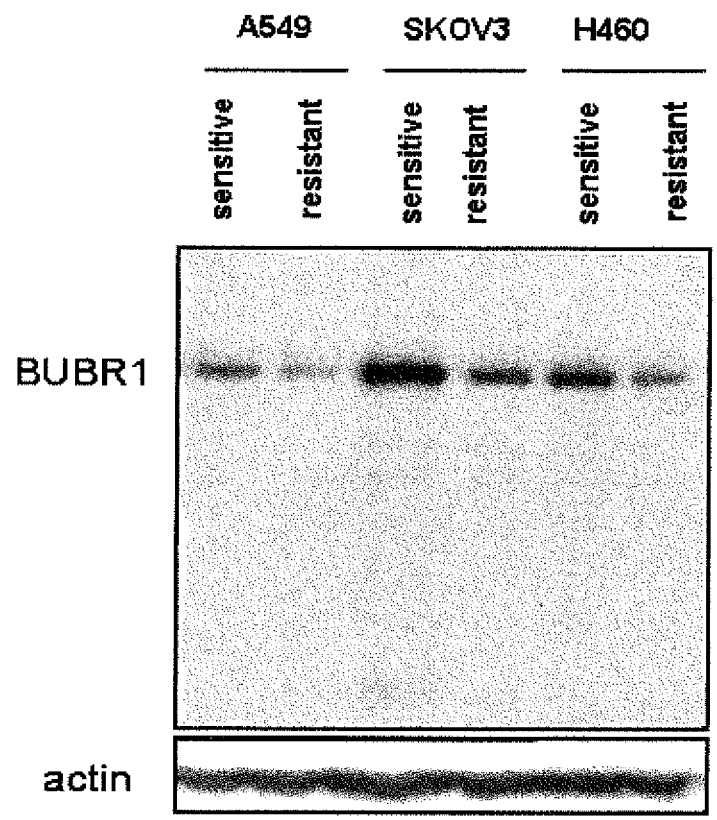

FIG. 14: Shows that BUBR1 protein levels decrease in tumour lines with acquired resistance to BAL27862. Tumour cell lines were selected for resistance to BAL27862 through in vitro cultivation in the presence of BAL27862. Based on $IC_{50}$ determinations, BAL27862 resistance factors versus parental lines were: A549 (3.0 fold); SKOV3 (7.6 fold—resistant 1 line); H460 (5.3 fold)(see Table 1). Whole cell protein extracts were prepared from parental and resistant lines and analysed by immunoblot for BUBR1 expression. Actin levels act as a loading control.

Figure 15:
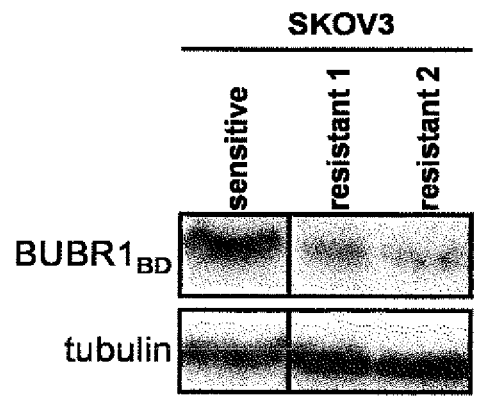

FIG. 15: Shows that decreased BUBR1 protein levels are maintained in the SKOV3 tumour line during resistance development. SKOV3 tumour cells were selected for resistance to BAL27862 through in vitro cultivation in the presence of BAL27862 for increasing time periods. Based on $IC_{50}$ determinations, BAL27862 resistance factors versus parental lines were: SKOV3 resistant 1 (7.6 fold), SKOV3 resistant 2 (11.6 fold)(see Table 1). Whole cell protein extracts were prepared from parental and resistant lines and analysed by immunoblot for BUBR1 expression using the BD Transduction Laboratories (BD) BUBR1 antibody. Alpha-tubulin levels act as a loading control.

Figure 16:
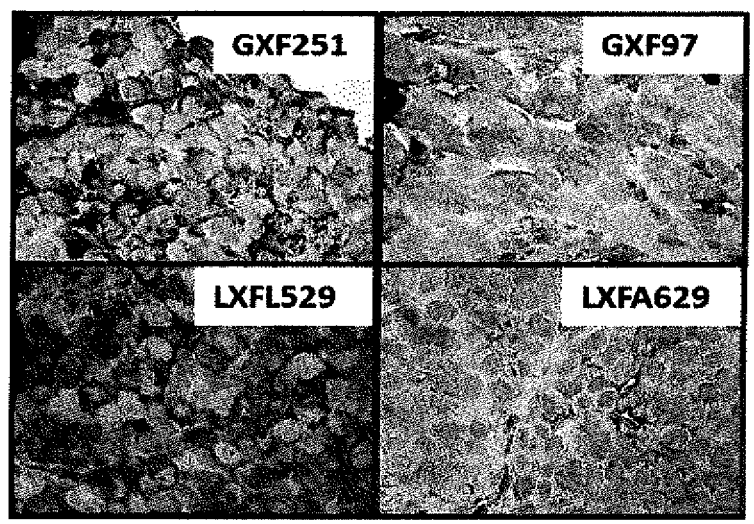

FIG. 16: Shows that tumour cell BUBR1 levels are decreased in patient-derived xenografted tumours defined as BAL27862 resistant by ex vivo colony outgrowth analysis. Patient-derived tumour xenografts (maintained in nude mice) were prepared, fixed and stained for BUBR1 protein expression using immunohistochemistry. BAL27862, paclitaxel and vinblastine resistance and sensitivity is as defined in Table 2.

Figure 17:
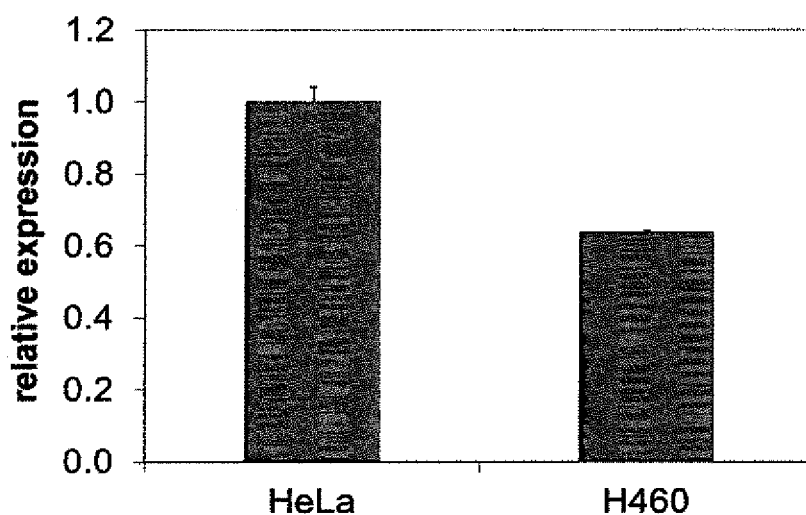
Figure 17:
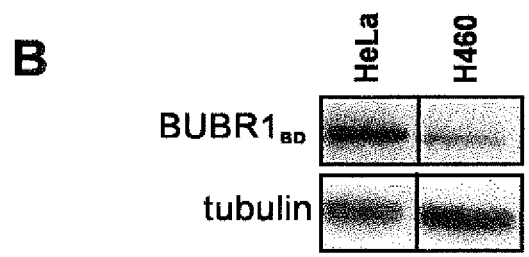

FIG. 17: Shows that for BUBR1, protein levels in tumour cells are reflected by its RNA expression levels. A: Samples were prepared from HeLa and H460 cell lines, and quantitative RT-PCR was performed on these to measure RNA levels. The HeLa results were set at 100%, and the graph shows the RNA expression levels in the H460 sample relative to the HeLa values. B: Whole cell protein extracts were prepared from the same passages of the HeLa and H460 cell lines and then analysed by immunoblotting using BD Transduction Laboratories (BD) BUBR1 antibodies for BUBR1 protein expression. Alpha-tubulin levels act as a loading control.

FIG. 18: Shows preferred protein sequence of BUBR1 (SEQ. ID No. 1)

FIGS. 19 and 20: Show preferred nucleic acid sequence of BUBR1 (SEQ. ID No. 2)

DETAILED DESCRIPTION

Compounds of General Formula I

The compounds according to the invention are represented by general formula I:

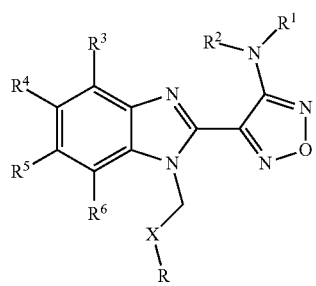

(I)

wherein

R represents phenyl, thienyl or pyridinyl wherein phenyl is optionally substituted by one or two substituents independently selected from alkyl, halo-lower alkyl, hydroxy-lower alkyl, lower alkoxy-lower alkyl, acyloxy-lower alkyl, phenyl, hydroxy, lower alkoxy, hydroxy-lower alkoxy, lower alkoxy-lower alkoxy, phenyl-lower alkoxy, lower alkylcarbonyloxy, amino, monoalkylamino, dialkylamino, lower alkoxycarbonylamino, lower alkylcarbonylamino, substituted amino wherein the two substituents on nitrogen form together with the nitrogen heterocyclyl, lower alkylcarbonyl, carboxy, lower alkoxycarbonyl, cyano, halogen, and nitro; and wherein two adjacent substituents are methylenedioxy;

and wherein pyridinyl is optionally substituted by lower alkoxy, amino or halogen;

X represents a group C=Y, wherein Y stands for oxygen or nitrogen substituted by hydroxy or lower alkoxy;

$R^1$ represents hydrogen, lower alkylcarbonyl, hydroxy-lower alkyl or cyano-lower alkyl;

$R^2$, $R^3$ and $R^6$ represent hydrogen;

$R^4$ and $R^5$, independently of each other, represent hydrogen, lower alkyl or lower alkoxy;

or $R^4$ and $R^5$ together represent methylenedioxy;

and pharmaceutically acceptable derivatives thereof, or wherein

R represents phenyl or pyridinyl wherein phenyl is optionally substituted by one or two substituents independently selected from alkyl, halo-lower alkyl, hydroxy-lower alkyl, lower alkoxy-lower alkyl, acyloxy-lower alkyl, phenyl, hydroxy, lower alkoxy, hydroxy-lower alkoxy, lower alkoxy-lower alkoxy, phenyl-lower alkoxy, lower alkylcarbonyloxy, amino, monoalkylamino, dialkylamino, lower alkoxycarbonylamino, lower alkylcarbonylamino, substituted amino wherein the two substituents on nitrogen form together with the nitrogen heterocyclyl, lower alkylcarbonyl, carboxy, lower alkoxycarbonyl, formyl, cyano, halogen, and nitro; and wherein two adjacent substituents are methylenedioxy;

and wherein pyridinyl is optionally substituted by lower alkoxy, amino or halogen;

X represents oxygen;

$R^1$ represents hydrogen, lower alkylcarbonyl, hydroxy-lower alkyl or cyano-lower alkyl;

$R^2$, $R^3$ and $R^6$ represent hydrogen;

$R^4$ and $R^5$, independently of each other, represent hydrogen, lower alkyl or lower alkoxy;

or $R^4$ and $R^5$ together represent methylenedioxy;

and pharmaceutically acceptable derivatives thereof;

and wherein the prefix lower denotes a radical having up to and including a maximum of 7, especially up to and including a maximum of 4 carbon atoms.

Heterocyclyl designates preferably a saturated, partially saturated or unsaturated, mono- or bicyclic ring containing 4-10 atoms comprising one, two or three heteroatoms selected from nitrogen, oxygen and sulfur, which may, unless otherwise specified, be carbon or nitrogen linked, wherein a ring nitrogen atom may optionally be substituted by a group selected from lower alkyl, amino-lower alkyl, aryl, aryl-lower alkyl and acyl, and a ring carbon atom may be substituted by lower alkyl, amino-lower alkyl, aryl, aryl-lower alkyl, heteroaryl, lower alkoxy, hydroxy or oxo. Examples of heterocyclyl are pyrrolidinyl, oxazolidinyl, thiazolidinyl, piperidinyl, morpholinyl, piperazinyl, dioxolanyl and tetrahydropyranyl.

Acyl designates, for example, alkylcarbonyl, cyclohexylcarbonyl, arylcarbonyl, aryl-lower alkylcarbonyl, or heteroarylcarbonyl. Lower acyl is preferably lower alkylcarbonyl, in particular propionyl or acetyl.

Preferably, the compound of general formula I according to the invention is defined as wherein $R^1$ is selected from the group consisting of hydrogen, acetyl, $CH_2CH_2CN$ and $CH_2CH_2CH_2OH$.

In one preferred embodiment, the compound of general formula I according to the invention is selected from the group consisting of:

4-(1-Phenacyl-1H-benzimidazol-2-yl)-furazan-3-ylamine,

4-[1-(4-Bromophenacyl)-1H-benzimidazol-2-yl]-furazan-3-ylamine oxime,

N-{4-[1-(4-Chlorophenacyl)-1H-benzimidazol-2-yl]-furazan-3-yl}-acetamide,

4-[1-(4-Chlorophenacyl)-1H-benzimidazol-2-yl]-furazan-3-yl-N-(2-cyanoethyl)-amine 4-[1-(4-Chlorophenacyl)-1H-benzimidazol-2-yl]-furazan-3-yl-N-(3-hydroxypropyl)-amine, 4-[1-(3-Amino-4-chlorophenacyl)-1H-benzimidazol-2-yl]-furazan-3-ylamine 4-[1-(3-Methoxy-4-methoxymethoxy-phenacyl)-1H-benzimidazol-2-yl]-furazan-3-ylamine, and pharmaceutically acceptable derivatives thereof.

In another preferred embodiment, the compound of general formula I according to the invention is:

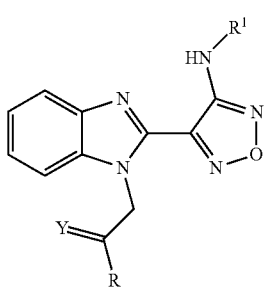
wherein
R, Y and R¹ are defined as follows:
| R | Y | R¹ |
|---|---|---|
| 4-Cl-C₆H₄- | O | H |
| C₆H₅- | NOH | H |
| C₆H₅- | NOMe | H |
| 4-MeO-C₆H₄- | O | H |
| 4-MeO-C₆H₄- | NOH | H |
| 4-Cl-C₆H₄- | NOH | H |
| 4-Cl-C₆H₄- | NOMe | H |
| 3-MeO-C₆H₄- | O | H |
| 3-MeO-C₆H₄- | NOH | H |
| 3-MeO-C₆H₄- | NOMe | H |
| 4-Ph-C₆H₄- | O | H |
| 4-Ph-C₆H₄- | NOH | H |
| 4-Ph-C₆H₄- | NOMe | H |
| 4-Br-C₆H₄- | O | H |
| 4-Br-C₆H₄- | NOMe | H |
| 2,4-Cl₂-C₆H₃- | O | H |
| 2-Cl-C₆H₄- | O | H |
| 2-Cl-C₆H₄- | NOH | H |
| 2-Cl-C₆H₄- | NOMe | H |
| 3-Cl-C₆H₄- | O | H |
| 3-Cl-C₆H₄- | NOH | H |
| 3-Cl-C₆H₄- | NOMe | H |
| 4-MeO-C₆H₄- | NOMe | H |

| R | Y | R¹ |
|---|---|---|
| 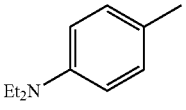 Et₂N-C₆H₄- | O | H |
| 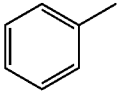 phenyl | O | Ac |
| 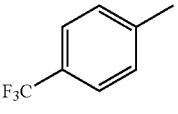 F₃C-C₆H₄- | O | H |
| 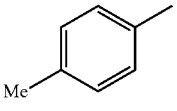 Me-C₆H₄- | O | H |
| 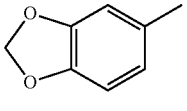 methylenedioxyphenyl | O | H |
| 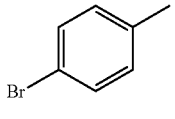 Br-C₆H₄- | O | CH₂CH₂CN |
| 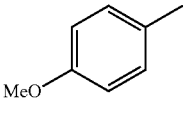 MeO-C₆H₄- | O | CH₂CH₂CN |
| 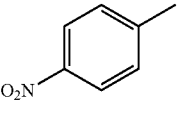 O₂N-C₆H₄- | O | H |
| 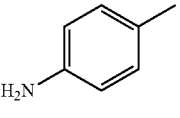 H₂N-C₆H₄- | O | H |
| 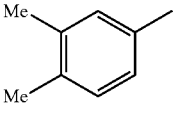 3,4-Me₂-C₆H₃- | O | CH₂CH₂CH₂OH |
| 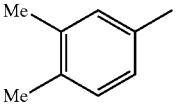 3,4-Me₂-C₆H₃- | O | H |
| 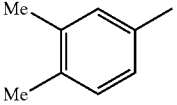 3,4-Me₂-C₆H₃- | O | CH₂CH₂CN |
| 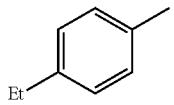 Et-C₆H₄- | O | H |

| R | Y | R¹ |
|---|---|---|
| 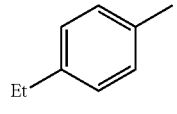 Et-C₆H₄- | O | CH₂CH₂CN |
| 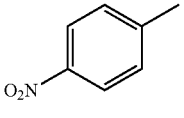 O₂N-C₆H₄- | O | CH₂CH₂CN |
| 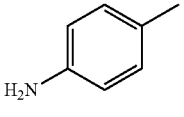 H₂N-C₆H₄- | O | CH₂CH₂CN |
| 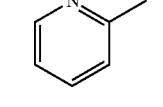 2-pyridyl | O | H |
| 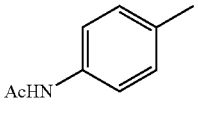 AcHN-C₆H₄- | O | H |
| 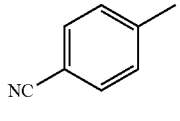 NC-C₆H₄- | O | H |
| 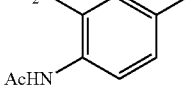 2-AcHN-4-Me-5-O₂N-C₆H₂- | O | H |
| 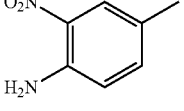 2-H₂N-4-Me-5-O₂N-C₆H₂- | O | H |
| 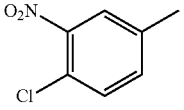 2-Cl-4-Me-5-O₂N-C₆H₂- | O | H |
| 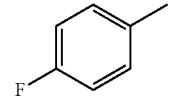 F-C₆H₄- | O | H |
| 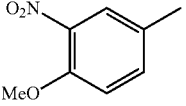 2-MeO-4-Me-5-O₂N-C₆H₂- | O | H |
| 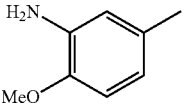 2-MeO-4-Me-5-H₂N-C₆H₂- | O | CH₂CH₂CN |
| 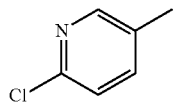 6-Cl-pyridin-3-yl | O | H |

-continued

| R | Y | R¹ |
|---|---|---|
| 2,5-difluoro-phenyl | O | H |
| thiophen-2-yl | O | H |
| 2-methoxy-4-benzyloxy-phenyl | O | H |
| 2-methoxy-4-hydroxy-phenyl | O | H |
| 2-methoxy-4-acetoxy-phenyl | O | H |
| 2,4-dimethoxy-phenyl | O | H |
| 4-(2-methoxyethoxy)-phenyl | O | H |
| 6-amino-pyridin-3-yl | O | H |
| 6-amino-pyridin-3-yl | O | CH₂CH₂CN |
| 3,4-dihydroxy-phenyl | O | H |
| 3,4-bis(methoxymethoxy)-phenyl | O | H |
| 6-methoxy-pyridin-3-yl | O | CH₂CH₂CN | or pharmaceutically acceptable derivatives thereof.

In yet another preferred embodiment, the compound of general formula I according to the invention is selected from the group consisting of:
4-(1-Phenoxymethyl-1H-benzimidazol-2-yl)-furazan-3-ylamine,
4-[1-(4-Fluorophenoxymethyl)-1H-benzimidazol-2-yl]-furazan-3-ylamine,
4-[1-(3,4-Dimethylphenoxymethyl)-1H-benzimidazol-2-yl]-furazan-3-yl-N-(2-cyanoethyl)-amine,
and compounds represented by the formula:

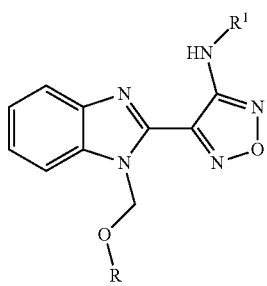

wherein R and R¹ are as defined below

| R | R¹ |
|---|---|
| 4-chloro-phenyl | H |
| 4-bromo-phenyl | H |
| 4-methoxy-phenyl | H |
| 4-trifluoromethyl-phenyl | H |
| 3,4-dichloro-phenyl | H |
| 4-chloro-phenyl | CH₂CH₂CN |
| 4-bromo-phenyl | CH₂CH₂CN |
| phenyl | CH₂CH₂CN |

-continued

| R | R¹ |
|---|---|
| 4-methylphenyl-CHO (OHC-C6H4-) | H |
| 4-methylphenyl-CH2OH (HO-CH2-C6H4-) | H |
| 4-methylphenyl-NO2 (O2N-C6H4-) | H |
| 4-methylphenyl-NH2 (H2N-C6H4-) | H |
| 4-methylphenyl-NH2 (H2N-C6H4-) | H |
| 3,4-dimethylphenyl | H |
| 3,5-bis(trifluoromethyl)phenyl | H |
| 3-(trifluoromethyl)phenyl | H |
| 4-methylphenyl | CH2CH2CN |
| 3,4-dimethylphenyl | CH2CH2CH2OH |
| 6-chloropyridin-3-yl | H |
| 6-aminopyridin-3-yl | H | or pharmaceutically acceptable derivatives thereof.

In still yet another preferred embodiment the compound of general formula I according to the invention is:

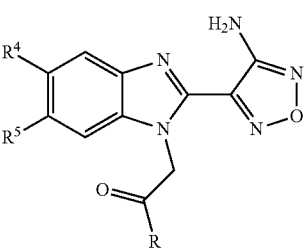

wherein R, R⁴ and R⁵ are as defined below

| R | R⁴ | R⁵ |
|---|---|---|
| phenyl | Me | Me |
| 4-bromophenyl | Me | Me |
| 4-chlorophenyl | Me | Me |
| 4-methoxyphenyl | Me | Me |
| 4-phenylphenyl | Me | Me |
| phenyl | OMe | OMe |
| 4-chlorophenyl | OMe | OMe |
| 4-bromophenyl | OMe | OMe |
| 4-methoxyphenyl | OMe | OMe |
| 4-phenylphenyl | OMe | OMe | or pharmaceutically acceptable derivatives thereof.

More preferably, the compound according to the invention is a compound of general formula I

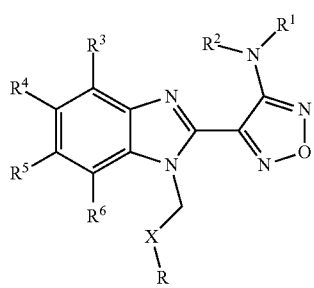

(I)

wherein
R represents phenyl or pyridinyl
wherein phenyl is optionally substituted by one or two substituents independently selected from lower alkyl, lower alkoxy, amino, acetylamino, halogen and nitro; and wherein pyridinyl is optionally substituted by amino or halogen;
X represents a group C=O;
$R^1$ represents hydrogen or cyano-lower alkyl;
$R^2$, $R^3$, $R^4$, Fe and $R^6$ represent hydrogen;
and pharmaceutically acceptable derivatives thereof,
and wherein the prefix lower denotes a radical having up to and including a maximum of 7, especially up to and including a maximum of 4 carbon atoms.

Especially preferably, the compound according to the invention is represented by the following formula

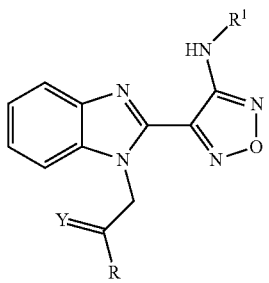

wherein R, Y and $R^1$ are defined as follows:

| R | Y | $R^1$ |
|---|---|---|
| H₂N-⟨phenyl⟩- | O | H |
| H₂N-⟨phenyl⟩- | O | CH₂CH₂CN |
| H₂N-⟨pyridinyl⟩- | O | H |
| H₂N-⟨pyridinyl⟩- | O | CH₂CH₂CN | or pharmaceutically acceptable derivatives thereof.

More especially preferably, the compound according to the invention is represented by the following formula

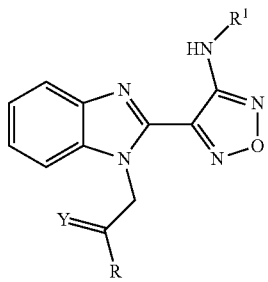

wherein R, Y and $R^1$ are defined as follows:

| R | Y | $R^1$ |
|---|---|---|
| H₂N-⟨phenyl⟩- | O | CH₂CH₂CN |
| H₂N-⟨phenyl⟩- | O | H |
| H₂N-⟨pyridinyl⟩- | O | CH₂CH₂CN | or pharmaceutically acceptable derivatives thereof.

Particularly preferably, the compound according to the invention is

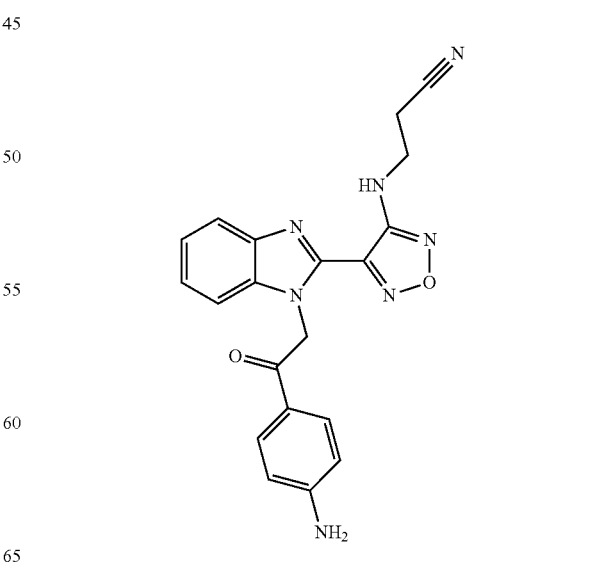

or pharmaceutically acceptable derivatives thereof.

The term derivative or derivatives in the phrase "pharmaceutically acceptable derivative" or "pharmaceutically acceptable derivatives" of compounds of general formula I relates to salts, solvates and complexes thereof and to solvates and complexes of salts thereof, as well as to pro-drugs, polymorphs, and isomers thereof (including optical, geometric and tautomeric isomers) and also salts of pro-drugs thereof. In a more preferred embodiment, it relates to salts and pro-drugs, as well as to salts of pro-drugs thereof.

Salts are preferably acid addition salts. Salts are formed, preferably with organic or inorganic acids, from compounds of formula (I) with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethanesulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

The compound according to the invention may be administered in the form of a pro-drug which is broken down in the human or animal body to give a compound of the formula I. Examples of pro-drugs include in vivo hydrolysable esters and amides of a compound of the formula I. Particular pro-drugs considered are ester and amides of naturally occurring amino acids and ester or amides of small peptides, in particular small peptides consisting of up to five, preferably two or three amino acids as well as esters and amides of pegylated hydroxy acids, preferably hydroxy acetic acid and lactic acid. Pro-drug esters are formed from the acid function of the amino acid or the C terminal of the peptide and suitable hydroxy group(s) in the compound of formula I. Pro-drug amides are formed from the amino function of the amino acid or the N terminal of the peptide and suitable carboxy group(s) in the compound of formula I, or from the acid function of the amino acid or the C terminal of the peptide and suitable amino group(s) in the compound of formula I. Particularly preferably the pro-drug amides are formed from the amino group(s) present within the R group of formula I.

More preferably, the pro-drug is an amide formed from an amino group present within the R group of the compound of general formula I as defined above and the carboxy group of glycine, alanine or lysine.

Even more preferably the compound of general formula I is in the form of a pro-drug selected from the compounds of formulae:

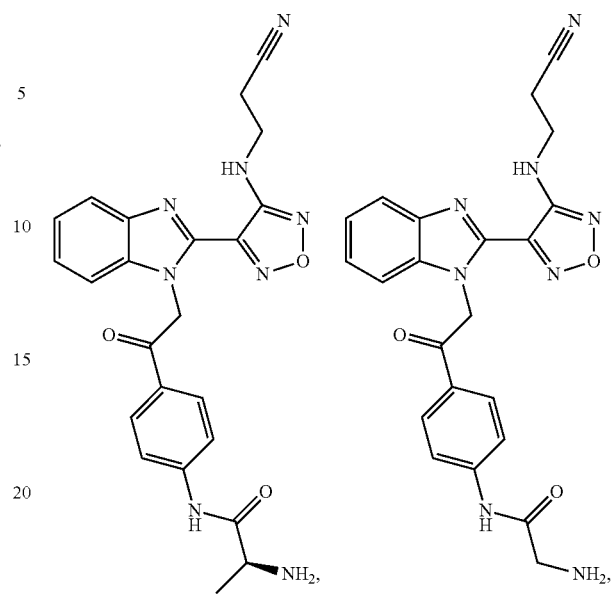

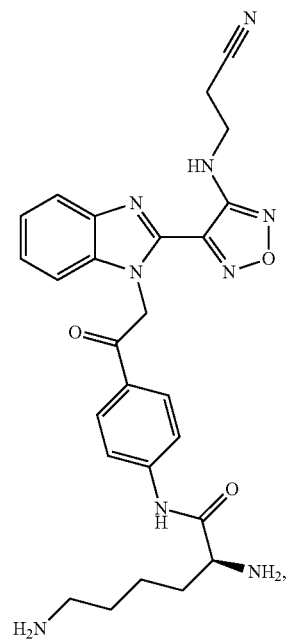

27
-continued
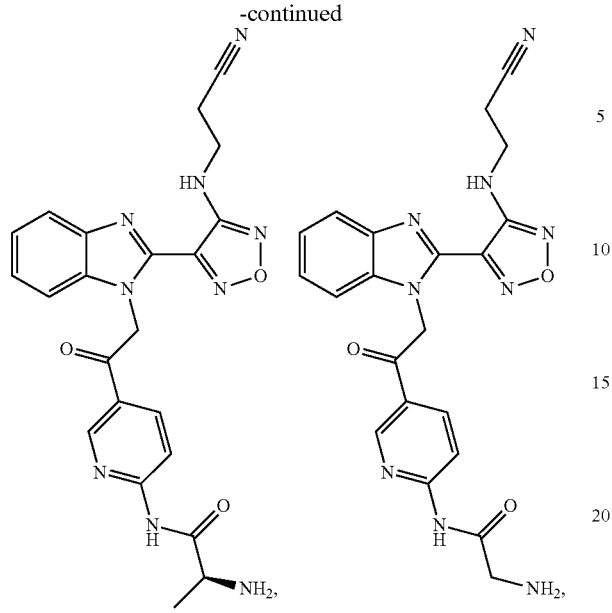
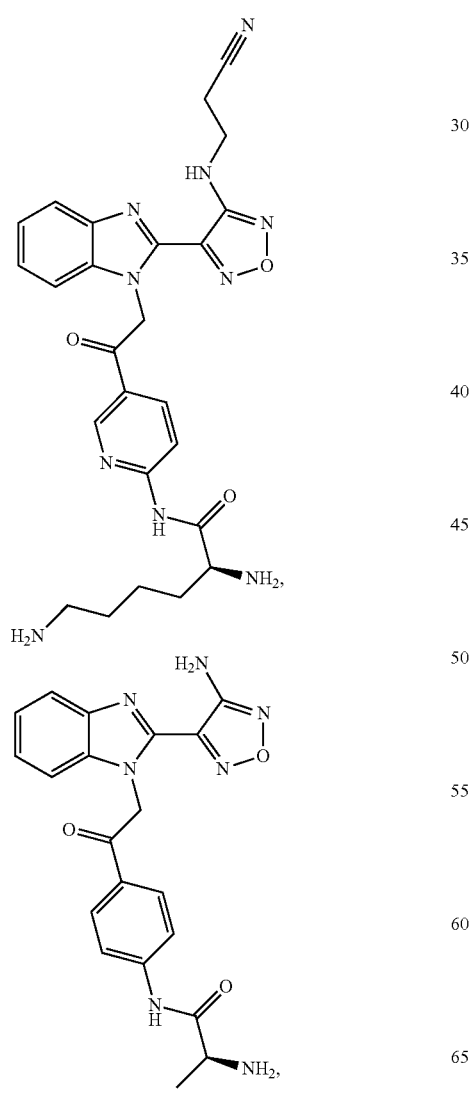
28
-continued
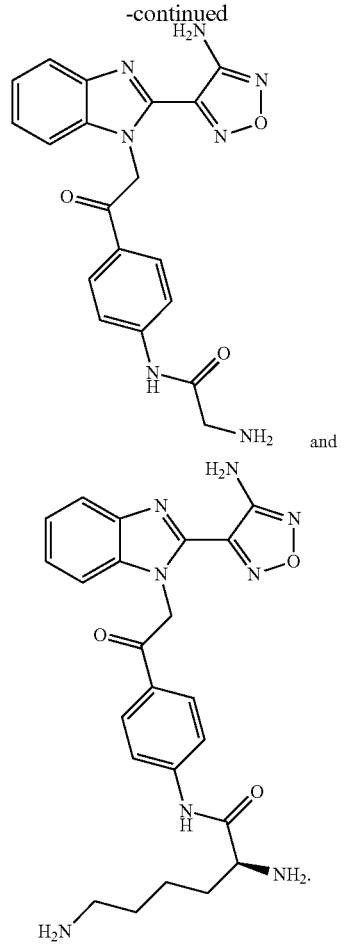
In an especially preferred embodiment the compound of general formula I according to the invention is in the form of a pro-drug which has the following formula
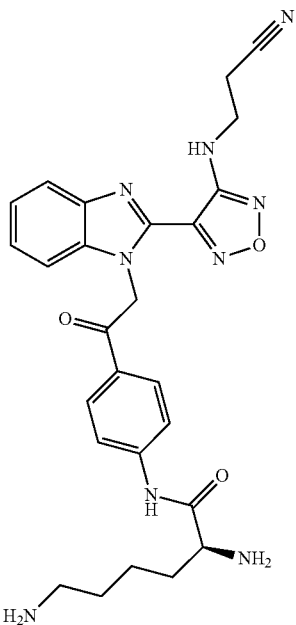

In a most especially preferred embodiment the compound according to the invention is

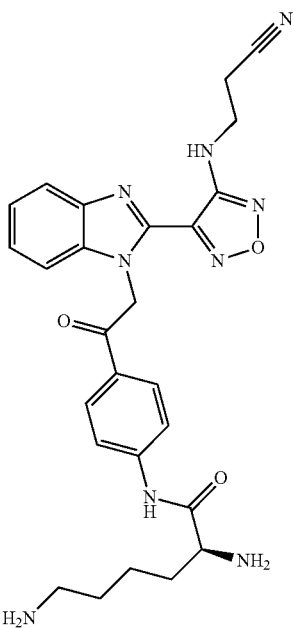 [SMILES: N#CCCNc1nonc1-c1nc2ccccc2n1CC(=O)c1ccc(NC(=O)[C@@H](N)CCCCN)cc1]

or a pharmaceutically acceptable salt thereof, preferably a hydrochloride salt, most preferably a dihydrochloride salt.

The pharmaceutically active metabolite in vivo in this case is BAL27862.

These pro-drugs may be prepared by processes that are known per se, in particular, a process, wherein a compound of formula (II)

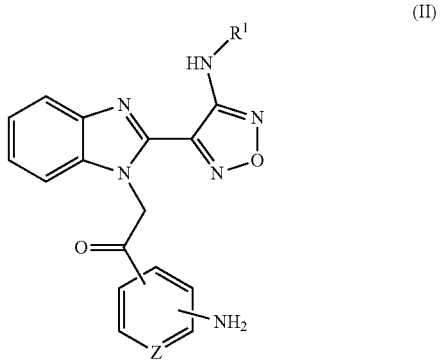

wherein R$^1$ is defined as for formula (I) and Z is CH or N, or a derivative of such a compound comprising functional groups in protected form,
or a salt thereof is
(1) acylated with an amino acid of formula (III)

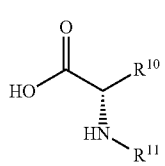

wherein
R$^{10}$ is selected from hydrogen (Gly); methyl (Ala) and protected aminobutyl (Lys) and R$^{11}$ is a suitable amino protecting group, and
(2) any protecting groups in a protected derivative of the resulting compound are removed to yield a pro-drug as shown above, and, if so desired,
(3) said pro-drug is converted into a salt by treatment with an acid, or a salt of a compound of formula (II) is converted into the corresponding free compound of formula (II) or into another salt, and/or a mixture of isomeric product compounds is separated into the individual isomers.

Acylation of a compound of formula (II) with an amino acid of formula (III) is performed in a manner known per se, usually in the presence of a suitable polar or dipolar aprotic solvent, with cooling or heating as required, for example in a temperature range from approximately minus 80° C. to approximately plus 150° C., more preferably from minus 30° C. to plus 120° C., especially in a range from approximately around 0° C. to the reflux temperature of the used solvent. Optionally a suitable base is added, in particularly an aromatic base like pyridine or collidine or a tertiary amine base such as triethylamine or diisopropylethylamine, or an inorganic basic salt, e.g. potassium or sodium carbonate.

Acylation may be accomplished under conditions used for amide formation known per se in peptide chemistry, e.g. with activating agents for the carboxy group, such as carbodiimides like N,N'-diethyl-, N,N'-dipropyl-, N,N'-diisopropyl-, N,N'-dicyclohexylcarbodiimide and N-(3-dimethylaminoisopropyl)-N'-ethylcarbodiimide-hydrochloride (EDC), or with agents such as 1-hydroxybenzotriazole (HOBt), benzotriazol-1-yloxytris(dimethylamino)-phosphonium hexafluorophosphate (BOP), O-(7-aza-benzotriazol-1-yl)-N,N,N',N'-tetramethyl-uronium hexafluorophosphate (HATU), 2-(2-oxo-1-(2H)-pyridyl)-1,1,3,3-tetramethyluronium tetrafluoroborate (TPTU), optionally in the presence of suitable bases, catalysts or co-reagents. The carboxy group may also be activated as acyl halogenide, preferably as acyl chloride, e.g. by reaction with thionylchloride or oxalylchloride, or as symmetrical or unsymmetrical anhydride, e.g. by reaction with halogeno formates like ethyl chloroformate, optionally in the presence of suitable bases, catalysts or co-reagents.

If one or more other functional groups, for example carboxy, hydroxy or amino, are or need to be protected in a compound of formula (II) or (III), because they should not take part in the reaction, these are such protecting groups as are usually applied in the synthesis of amides like, in particular peptide compounds, cephalosporins, penicillins, nucleic acid derivatives and sugars, which are known to the skilled persons. Suitable protecting groups for amino groups are for example t-butyl carbamate, benzyl carbamate or 9-fluorenylmethyl carbamate.

The protecting groups may already be present in precursors and should protect the functional groups concerned against unwanted secondary reactions, such as alkylations, acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end products. The specialist knows, or can easily establish, which protecting groups are suitable with the reactions mentioned hereinabove and hereinafter.

The protection of such functional groups by such protecting groups, the protecting groups themselves, and their removal reactions are described for example in standard reference books for peptide synthesis and in special books on protective groups such as
J. F. W. McOmie, "Protective Groups in Organic Chemistry", Plenum Press, London and New York 1973, in "Methoden der organischen Chemie" (Methods of organic chemistry), Houben-Weyl, 4th edition, Volume 15/I, Georg Thieme Verlag, Stuttgart 1974, and in T. W. Greene, G. M. Wuts "Protective Groups in Organic Synthesis", Wiley, New York, 2006.

Disease

The compounds of general formula I according to the invention have been shown to arrest cell proliferation and induce apoptosis.

Deregulation of cell proliferation, or lack of appropriate cell death, has wide ranging clinical implications. A number of diseases associated with such deregulation involve hyperproliferation, inflammation, tissue remodeling and repair. Familiar indications in this category include cancers, restenosis, neointimal hyperplasia, angiogenesis, endometriosis, lymphoproliferative disorders, transplantation related pathologies (graft rejection), polyposis, loss of neural function in the case of tissue remodeling and the like.

Cancer is associated with abnormal cell proliferation and cell death rates. As apoptosis is inhibited or delayed in most types of proliferative, neoplastic diseases, induction of apoptosis is an option for treatment of cancer, especially in cancer types which show resistance to classic chemotherapy, radiation and immunotherapy (Apoptosis and Cancer Chemotherapy, Hickman and Dive, eds., Blackwell Publishing, 1999). Also in autoimmune and transplantation related diseases and pathologies compounds inducing apoptosis may be used to restore normal cell death processes and therefore can eradicate the symptoms and might cure the diseases. Further applications of compounds inducing apoptosis may be in restenosis, i.e. accumulation of vascular smooth muscle cells in the walls of arteries, and in persistent infections caused by a failure to eradicate bacteria- and virus-infected cells. Furthermore, apoptosis can be induced or reestablished in epithelial cells, in endothelial cells, in muscle cells, and in others which have lost contact with extracellular matrix.

A compound according to general formula I may be used for the prophylactic or especially therapeutic treatment of the human or animal body, in particular for treating a neoplastic disease, autoimmune disease, transplantation related pathology and/or degenerative disease. Examples of such neoplastic diseases include, but are not limited to, epithelial neoplasms, squamous cell neoplasms, basal cell neoplasms, transitional cell papillomas and carcinomas, adenomas and adenocarcinomas, adnexal and skin appendage neoplasms, mucoepidermoid neoplasms, cystic neoplasms, mucinous and serous neoplasms, ducal-, lobular and medullary neoplasms, acinar cell neoplasms, complex epithelial neoplasms, specialized gonadal neoplasms, paragangliomas and glomus tumours, naevi and melanomas, soft tissue tumours and sarcomas, fibromatous neoplasms, myxomatous neoplasms, lipomatous neoplasms, myomatous neoplasms, complex mixed and stromal neoplasms, fibroepithelial neoplasms, synovial like neoplasms, mesothelial neoplasms, germ cell neoplasms, trophoblastic neoplasms, mesonephromas, blood vessel tumours, lymphatic vessel tumours, osseous and chondromatous neoplasms, giant cell tumours, miscellaneous bone tumours, odontogenic tumours, gliomas, neuroepitheliomatous neoplasms, meningiomas, nerve sheath tumours, granular cell tumours and alveolar soft part sarcomas, Hodgkin's and non-Hodgkin's lymphomas, other lymphoreticular neoplasms, plasma cell tumours, mast cell tumours, immunoproliferative diseases, leukemias, miscellaneous myeloproliferative disorders, lymphoproliferative disorders and myelodysplastic syndromes.

The compounds of general formula I or pharmaceutically acceptable derivatives thereof may be used to treat autoimmune diseases. Examples of such autoimmune diseases include, but are not limited to, systemic, discoid or subacute cutaneous lupus erythematosus, rheumatoid arthritis, antiphospholipid syndrome, CREST, progressive systemic sclerosis, mixed connective tissue disease (Sharp syndrome), Reiter's syndrome, juvenile arthritis, cold agglutinin disease, essential mixed cryoglobulinemia, rheumatic fever, ankylosing spondylitis, chronic polyarthritis, myasthenia gravis, multiple sclerosis, chronic inflammatory demyelinating polyneuropathy, Guillan-Barre syndrome, dermatomyositis/polymyositis, autoimmune hemolytic anemia, thrombocytopenic purpura, neutropenia, type I diabetes mellitus, thyroiditis (including Hashimoto's and Grave's disease), Addison's disease, polyglandular syndrome, pemphigus (vulgaris, foliaceus, sebaceous and vegetans), bullous and cicatricial pemphigoid, pemphigoid gestationis, epidermolysis bullosa acquisita, linear IgA disease, lichen sclerosus et atrophicus, morbus Duhring, psoriasis vulgaris, guttate, generalized pustular and localized pustular psoriasis, vitiligo, alopecia areata, primary biliary cirrhosis, autoimmune hepatitis, all forms of glomerulonephritis, pulmonal hemorrhage (goodpasture syndrome), IgA nephropathy, pernicious anemia and autoimmune gastritis, inflammatory bowel diseases (including colitis ulcerosa and morbus Crohn), Behcet's disease, Celic-Sprue disease, autoimmune uveitis, autoimmune myocarditis, granulomatous orchitis, aspermatogenesis without orchitis, idiopatic and secondary pulmonary fibrosis, inflammatory diseases with a possibility of autoimmune pathogensesis, such as pyoderma gangrensosum, lichen ruber, sarcoidosis (including Lofgren and cutaneous/subcutaneous type), granuloma anulare, allergic type I and type IV immunolgical reaction, asthma bronchiale, pollinosis, atopic, contact and airborne dermatitis, large vessel vasculitis (giant cell and Takayasu's arteritis), medium sized vessel vasculitis (polyarteritis nodosa, Kawasaki disease), small vessel vasculitis (Wegener's granulomatosis, Churg Strauss syndrome, microscopic polangiitis, HenochSchoenlein purpura, essential cryoglobulinemic vasculitis, cutaneous leukoklastic angiitis), hypersensitivity syndromes, toxic epidermal necrolysis (Stevens-Johnson syndrome, erythema multiforme), diseases due to drug side effects, all forms of cutaneous, organ-specific and systemic effects due to type I-vu (Coombs classification) immunologic forms of reaction, transplantation related pathologies, such as acute and chronic graft versus host and host versus graft disease, involving all organs (skin, heart, kidney, bone marrow, eye, liver, spleen, lung, muscle, central and peripheral nerve system, connective tissue, bone, blood and lymphatic vessel, genito-urinary system, ear, cartilage, primary and secondary lymphatic system including bone marrow, lymph node, thymus, gastrointestinal tract, including oropharynx, esophageus, stomach, small intestine, colon, and rectum, including parts of above mentioned organs down to single cell level and substructures, e. g. stem cells).

Particularly preferably, the disease according to the invention is a neoplastic or autoimmune disease. In an especially preferred embodiment the disease is cancer.

Examples of cancers in terms of the organs and parts of the body affected include, but are not limited to, the breast, cervix, ovaries, colon, rectum, (including colon and rectum i.e. colorectal cancer), lung, (including small cell lung cancer, non-small cell lung cancer, large cell lung cancer and mesothelioma), endocrine system, bone, adrenal gland, thymus, liver, stomach, intestine, (including gastric cancer), pancreas, bone marrow, hematological malignancies, (such as lymphoma, leukemia, myeloma or lymphoid malignancies), bladder, urinary tract, kidneys, skin, thyroid, brain, head, neck, prostate and testis. Preferably the cancer is selected from the group consisting of breast cancer, prostate cancer, cervical cancer, ovarian cancer, gastric cancer, colorectal cancer, pancreatic cancer, liver cancer, brain cancer, neuroendocrine cancer, lung cancer, kidney cancer, hematological malignancies, melanoma and sarcomas. Especially preferably the cancer is selected from the group consisting of breast cancer, cervical cancer, ovarian cancer, gastric cancer, pancreatic cancer, colon cancer and lung cancer. More especially preferably the cancer is selected from the group consisting of cervical cancer, gastric cancer, ovarian cancer, pancreatic cancer, colon cancer and lung cancer.

Samples

The measurement of the level of BUBR1 may be performed in vitro, on a sample of biological tissue derived from the subject. The sample may be any biological material separated from the body such as, for example, normal tissue, tumour tissue, cell lines, plasma, serum, whole blood, cerebrospinal fluid, lymph fluid, circulating tumour cells, cell lysate, tissue lysate, urine and aspirates. Preferably the sample is derived from normal tissue, tumour tissue, cell lines, circulating tumour cells or blood. More preferably the sample is derived from tumour tissue or circulating tumour cells. In one particularly preferred embodiment the sample is derived from tumour tissue. For example, the level of BUBR1 may be measured in a fresh, frozen or formalin fixed/paraffin embedded tumour tissue sample.

The sample is pre-obtained from the subject before the sample is subjected to the method steps involving measuring the level of the biomarker. The methods for removal of the sample are well known in the art, and it may for example be removed from the subject by biopsy, for example by punch biopsy, core biopsy or aspiration fine needle biopsy, endoscopic biopsy, or surface biopsy. A blood sample may be collected by venipuncture and further processed according to standard techniques. Circulating tumour cells may also be obtained from blood based on, for example, size (e.g. ISET—Isolation by Size of Epithelial Tumour cells) or immunomagnetic cell enrichment. (e.g. CellSearch®, Veridex, Raritan, N.J.).

Sample Comparison

The subject according to the invention may be human or animal. Preferably the subject is human.

The biomarker BUBR1 is measured ex vivo in a sample or samples taken from the human or animal body, preferably taken from the human body. The sample or samples are pre-obtained from the human or animal body, preferably pre-obtained from the human body before the sample is subjected to the method steps involving measuring the level of the biomarker.

A biomarker is in general a substance that is used as an indicator of a biological response, preferably as an indicator of the susceptibility to a given treatment, which in the present application is treatment with a compound of general formula I or a pharmaceutically acceptable derivative thereof.

In a particularly preferred embodiment, lower BUBR1 levels in the sample relative to a standard value or set of standard values predicts resistance. As used herein, a decrease or relatively low or low or lower levels relative to a standard level or set of standard levels means the amount or concentration of the biomarker in a sample is detectably less in the sample relative to the standard level or set of standard levels. This encompasses at least a decrease of, or lower level of, about 1% relative to the standard, preferably at least a decrease of about 5% relative to the standard. More preferably it is a decrease of, or lower level of, at least about 10% relative to the standard. More particularly preferably it is a decrease of, or lower level of, at least about 20% relative to the standard. For example, such a decrease of, or lower level of, may include, but is not limited to, at least about 1%, about 10%, about 20%, about 30%, about 50%, about 70%, about 80%, about 90% or about a 100% decrease relative to the standard. Thus a decrease also includes the absence of detectable BUBR1 in the sample.

Preferably, lower BUBR1 levels in a sample or samples
i) relative to a standard value or set of standard values from subjects with the same tumour histotype; or
ii) taken after treatment initiation and compared to a sample or samples taken from the same subject before treatment initiation, or
iii) relative to a standard value or set of standard values from normal cells, tissue or body fluid;
are predictive of resistance.

The measuring of a level of BUBR1 is performed ex-vivo in a sample pre-obtained from the subject. Further preferably the response which is to be predicted is resistance.

More preferably, lower BUBR1 levels in a sample or samples
i) relative to a standard value or set of standard values from subjects with the same tumour histotype; or
ii) taken after treatment initiation and compared to a sample or samples taken from the same subject before treatment initiation;
are predictive of resistance.

Especially preferably, lower BUBR1 levels in a sample or samples relative to a standard value or set of standard values from subjects with the same tumour histotype are predictive of resistance.

In one preferred embodiment, for the case i) where the measurement is compared in a sample or samples relative to a standard value or set of standard values from samples from subjects with the same tumour histotype as the sample to which it is to be compared, the standard value or set of standard values are established from samples from a population of subjects with that cancer type. The samples from these standard subjects may for example be derived from tumour tissue or from circulating tumour cells, as long as the origin of the sample is consistent between the standard and the sample to be compared.

In another preferred embodiment, for the case ii) where the measurement is compared in a sample or samples taken after treatment initiation and compared to a sample or samples taken from the same subject before treatment initiation, it is measured preferably to predict acquired resistance. The samples are compared to cells or tissue from the same biological origin. The prediction of acquired resistance would then indicate that the treatment with the compound should be discontinued. The biomarker is thus used to monitor whether further treatment with the compound is likely to give the required response (e.g. reduction of abnormal cells), or whether the cells have become non-responsive or resistant to such treatment.

In yet another preferred embodiment, for the case iii) where the measurement is compared in a sample or samples relative to a standard value or set of standard values from normal cells, tissue or body fluid, the standard value or set of standard values may be established from a sample of normal (e.g. non-tumourous) cells, tissue or body fluid. Such data may be gathered from a population of subjects in order to develop the standard value or set of standard values.

The standard value or set of standard values are established ex-vivo from pre-obtained samples which may be from cell lines, or preferably biological material from at least one subject and more preferably from an average of subjects (e.g., n=2 to 1000 or more).

The standard value or set of standard values may then be correlated with the response data of the same cell lines, or same subjects, to treatment with a compound of general formula I or a pharmaceutically acceptable derivative thereof. From this correlation a comparator module, for example in the form of a relative scale or scoring system, optionally including cut-off or threshold values, can be established which indicates the levels of biomarker associated with a spectrum of response levels to the compound of formula I or a pharmaceutically acceptable derivative thereof. The spectrum of response levels may comprise relative sensitivity to the therapeutic activity of the compound, (e.g. high sensitivity to low sensitivity), as well as resistance to the therapeutic activity. In a preferred embodiment this comparator module comprises a cut-off value or set of values which predicts resistance to treatment.

For example, if an immunohistochemical method is used to measure the level of BUBR1 in a sample, standard values may be in the form of a scoring system. Such a system might take into account the percentage of cells in which staining for BUBR1 is present. The system may also take into account the relative intensity of staining in the individual cells. The standard values or set of standard values of the level of BUBR1 may then be correlated with data indicating the response, especially resistance, of the subject or tissue or cell line to the therapeutic activity of a compound of formula I or a pharmaceutically acceptable derivative thereof. Such data may then form part of a comparator module.

Response is the reaction of the cell lines, or preferably of the subject, or more preferably of the disease in a subject, to the activity, preferably therapeutic activity, of a compound of general formula I or a pharmaceutically acceptable derivative thereof. The spectrum of response levels may comprise relative sensitivity to the activity, preferably therapeutic activity, of the compound, (e.g. high sensitivity to low sensitivity), as well as resistance to the activity, preferably therapeutic activity. The response data may for example be monitored in terms of: objective response rates, time to disease progression, progression free survival, and overall survival.

The response of a cancerous disease may be evaluated by using criteria well known to a person in the field of cancer treatment, for example but not restricted to, Response Evaluation Criteria in Solid Tumors (RECIST) Guidelines, Source: Eisenhauer E A, Therasse P, Bogaerts J, Schwartz L H, Sargent D, Ford R, Dancey J, Arbuck S, Gwyther S, Mooney M, Rubinstein L, Shankar L, Dodd L, Kaplan R, Lacombe D, Verweij J. New response evaluation criteria in solid tumours: revised RECIST guideline (version 1.1). Eur J Cancer. 2009; 45:228-47;

RANO Criteria for High-Grade Gliomas, Source: Wen P Y, Macdonald D R, Reardon D A, Chloughesy T F, Sorensen A G, Galanis E, Degroot J, Wick W, Gilbert M R, Lassman A B, Tsien C, Mikkelsen T, Wong E T, Chamberlain M C, Stupp R, Lamborn K R, Vogelbaum M A, van den Bent M J, Chang S M. Updated response assessment criteria for high-grade gliomas: response assessment in neuro-oncology working group. J Clin Oncol. 2010; 28(11):1963-72;

CA-125 Rustin Criteria for Ovarian Cancer Response,
Source: Rustin G J, Quinn M, Thigpen T, du Bois A, Pujade-Lauraine E, Jakobsen A, Eisenhauer E, Sagae S, Greven K, Vergote I, Cervantes A, Vermorken J. Re: New guidelines to evaluate the response to treatment in solid tumors (ovarian cancer). J Natl Cancer Inst. 2004; 96(6): 487-8;

and

PSA Working Group 2 Criteria for Prostate Cancer Response,
Source: Scher H I, Halabi S, Tannock I, Morris M, Sternberg C N, Carducci M A, Eisenberger M A, Higano C, Bubley G J, Dreicer R, Petrylak D, Kantoff P, Basch E, Kelly W K, Figg W D, Small E J, Beer T M, Wilding G, Martin A, Hussain M; Prostate Cancer Clinical Trials Working Group. Design and end points of clinical trials for patients with progressive prostate cancer and castrate levels of testosterone: recommendations of the Prostate Cancer Clinical Trials Working Group. J Clin Oncol. 2008; 26(7): 1148-59.

Resistance is associated with there not being an observable and/or measurable reduction in, or absence of, one or more of the following: reduction in the number of abnormal cells, preferably cancerous cells or absence of the abnormal cells, preferably cancerous cells; for cancerous diseases: reduction in tumour size; inhibition (i.e., slowed to some extent and preferably stopped) of further tumour growth; reduction in the levels of tumour markers such as PSA and CA-125, inhibition (i.e., slowed to some extent and preferably stopped) of cancer cell infiltration into other organs (including the spread of cancer into soft tissue and bone); inhibition (i.e., slowed to some extent and preferably stopped) of tumour metastasis; alleviation of one or more of the symptoms associated with the specific cancer; and reduced morbidity and mortality.

In a preferred embodiment resistance means there is no observable and/or measurable reduction in, or absence of, one or more of the following criteria: reduction in tumour size; inhibition of further tumour growth, inhibition of cancer cell infiltration into other organs; and inhibition of tumour metastasis.

In a more preferred embodiment resistance refers to one or more of the following criteria: no reduction in tumour size; no inhibition of further tumour growth, no inhibition of cancer cell infiltration into other organs; and no inhibition of tumour metastasis.

Measurement of the aforementioned resistance criteria is according to clinical guidelines well known to a person in the field of cancer treatment, such as those listed above for measuring the response of a cancerous disease.

Response may also be established in vitro by assessing cell proliferation and/or cell death. For example, effects on cell death or proliferation may be assessed in vitro by one or more of the following well established assays: A) Nuclear staining with Hoechst 33342 dye providing information about nuclear morphology and DNA fragmentation which are hallmarks of apoptosis. B) AnnexinV binding assay which reflects the phosphatidylserine content of the outer lipid bilayer of the plasma membrane. This event is considered an early hallmark of apoptosis. C) TUNEL assay (Terminal deoxynucleotidyl transferase mediated dUTP Nick End Labeling assay), a fluorescence method for evaluating cells undergoing apoptosis or necrosis by measuring DNA fragmentation by labeling the terminal end of nucleic acids. D) MTS proliferation assay measuring the metabolic activity of cells. Viable cells are metabolically active whereas cells with a compromised respiratory chain show a reduced activity in this test. E) Crystal violet staining assay, where effects on cell number are monitored through direct staining of cellular components. F) Proliferation assay monitoring DNA synthesis through incorporation of bromodeoxyuridine (BrdU). Inhibitory effects on growth/proliferation can be directly determined. G) YO-PRO assay which involves a membrane impermeable, fluorescent, monomeric cyanine, nucleic acid stain, which permits analysis of dying (e.g. apoptotic) cells without interfering with cell viability. Overall effects on cell number can also be analysed after cell permeabilisation. H) Propidium iodide staining for cell cycle distribution which shows alterations in distribution among the different phases of the cell cycle. Cell cycle arresting points can be determined. I) Anchorage-independent growth assays, such as colony outgrowth assays which assess the ability of single cell suspensions to grow into colonies in soft agar.

In a preferred embodiment relating to determination of resistance in vitro, resistance means there is no decrease in the proliferation rate of abnormal cells and/or reduction in the number of abnormal cells. More preferably resistance means there is no decrease in the proliferation rate of cancerous cells and/or no reduction in the number of cancerous cells. The reduction in the number of abnormal, preferably cancerous, cells may occur through a variety of programmed and non-programmed cell death mechanisms. Apoptosis, caspase-independent programmed cell death and autophagic cell death are examples of programmed cell death. However the cell death criteria involved in embodiments of the invention is not to be taken as limited to any one cell death mechanism.

BUBR1

As described above, the term BUBR1 is used herein to encompass all the previously mentioned synonyms and refers to this entity on both the nucleic acid and protein levels as appropriate. Nucleic acid levels refer to for example mRNA, cDNA or DNA and the term protein includes the translated polypeptide or protein sequence and post-translationally modified forms thereof.

A preferred example of the protein sequence of BUBR1 (human BUBR1) is listed in SEQ. ID No. 1, FIG. 18. However the term BUBR1 also encompasses homologues, mutant forms, allelic variants, isotypes, splice variants and equivalents of this sequence. Preferably also it encompasses human homologues, mutant forms, allelic variants, isotypes, splice variants and equivalents of this sequence. More preferably it encompasses sequences having at least about 75% identity, especially preferably at least about 85% identity, particularly preferably at least about 95% identity, and more particularly preferably about 99% identity, to said sequence.

In an especially preferred embodiment, BUBR1 is the entity on the nucleic acid or protein levels, which is represented on the protein level by SEQ ID NO. 1 or sequences having at least 95% identity with this sequence, preferably at least 99% identity. In a particularly preferred embodiment, BUBR1 is represented by SEQ. ID. No. 1.

A preferred example of the nucleic acid sequence of BUBR1 (Human BUBR1) is accessible via NCBI Reference Sequence NM_001211, and is listed in SEQ. ID. No. 2 (NM_001211.5), FIGS. 19 and 20. The term BUBR1 also encompasses modifications, more degenerate variants of said sequence, complements of said sequence, and oligonucleotides that hybridise to one of said sequences. Such modifications include, but are not limited to, mutations, insertions, deletions, and substitutions of one or more nucleotides. More preferably it encompasses sequences having at least about 75% identity to said sequence, especially preferably at least about 85% identity, particularly preferably at least about 95% identity and more particularly preferably about 99% identity.

In yet another preferred embodiment, BUBR1 is the entity on the nucleic acid or protein levels, which is represented on the nucleic acid level by SEQ ID NO. 2 or sequences having at least 95% identity with this sequence, preferably at least 99% identity. In a particularly preferred embodiment, BUBR1 is represented by SEQ. ID. No. 2.

Level of BUBR1

The level of BUBR1 may be assayed in the sample by technical means well known to a skilled person. It may be assayed at the transcriptional or translational level.

In one preferred embodiment the level of BUBR1 nucleic acid, preferably BUBR1 mRNA, in a sample is measured. Examples of methods of gene expression analysis known in the art which are suitable to measure the level of BUBR1 at the nucleic acid level include, but are not limited to, i) using a labelled probe that is capable of hybridising to mRNA; ii) using PCR involving one or more primers based on the BUBR1 gene sequence, for example using quantitative PCR methods using labelled probes, e.g. fluorogenic probes, such as quantitative real-time PCR; iii) micro-arrays; IV) northern blotting V) serial analysis of gene expression (SAGE), READS (restriction enzyme amplification of digested cDNAs), differential display and measuring microRNA.

In a preferred embodiment the level of BUBR1 at the protein level is measured. Examples of methods of protein expression analysis known in the art which are suitable to measure the level of BUBR1 at the protein level include, but are not limited to, i) immunohistochemistry (IHC) analysis, ii) western blotting iii) immunoprecipitation iv) enzyme linked immunosorbant assay (ELISA) v) radioimmunoassay vi) Fluorescence activated cell sorting (FACS) vii) mass spectrometry, including matrix assisted laser desorption/ionization (MALDI, e.g. MALDI-TOF) and surface enhanced laser desorption/ionization (SELDI, e.g. SELDI-TOF).

The antibodies involved in some of the above methods may be monoclonal or polyclonal antibodies, antibody fragments, and/or various types of synthetic antibodies, including chimeric antibodies. The antibody may be labelled to enable it to be detected or capable of detection following reaction with one or more further species, for example using a secondary antibody that is labelled or capable of producing a detectable result. Antibodies specific to BUBR1 are available commercially from BD Transduction Laboratories and Cell Signaling Technology, Inc., or can be prepared via conventional antibody generation methods well known to a skilled person.

Preferred methods of protein analysis are ELISA, mass spectrometry techniques, immunohistochemistry and western blotting, more preferably western blotting and immunohistochemistry. In western blotting, also known as immunoblotting, labelled antibodies may be used to assess levels of protein, where the intensity of the signal from the detectable label corresponds to the amount of protein, and can be quantified for example by densitometry.

Immunohistochemistry again uses labelled antibodies to detect the presence and relative amount of the biomarker. It can be used to assess the percentage of cells for which the biomarker is present. It can also be used to assess the localisation or relative amount of the biomarker in individual cells; the latter is seen as a function of the intensity of staining.

ELISA stands for enzyme linked immunosorbant assay, since it uses an enzyme linked to an antibody or antigen for the detection of a specific protein. ELISA is typically performed as follows (although other variations in methodology exist): a solid substrate such as a 96 well plate is coated with a primary antibody, which recognises the biomarker. The bound biomarker is then recognised by a secondary antibody specific for the biomarker. This may be directly joined to an enzyme or a third anti-immunoglobulin antibody may be used which is joined to an enzyme. A substrate is added and the enzyme catalyses a reaction, yielding a specific colour. By measuring the optical density of this colour, the presence and amount of the biomarker can be determined.

Uses of Biomarker

In one preferred embodiment, the biomarker is used to predict inherent resistance of the disease in a subject to the compound of general formula I or a pharmaceutically acceptable derivative thereof as defined above.

In another preferred embodiment, the biomarker is used to predict acquired resistance of the disease in a subject to the compound of general formula I or a pharmaceutically acceptable derivative thereof as defined above.

The biomarker may be used to select subjects suffering or predisposed to suffering from a disease, preferably cancer, for treatment with a compound of general formula I or a pharmaceutically acceptable derivative thereof as defined above. The levels of such a biomarker may be used to identify patients likely to respond or to not respond or to continue to respond or to not continue to respond to treatment with such agents. Stratification of patients may be made in order to avoid unnecessary treatment regimes. In particular the biomarker may be used to identify subjects from whom a sample or samples do not display a lower level of BUBR1, relative to a standard level or set of standard levels, whereupon such subjects may then be selected for treatment with the compound of formula I or a pharmaceutically acceptable derivative thereof as defined above.

The biomarker may also be used to assist in the determination of treatment regimes, regarding amounts and schedules of dosing. Additionally, the biomarker may be used to assist in the selection of a combination of drugs to be given to a subject, including a compound or compounds of general formula I or a pharmaceutically acceptable derivative thereof, and another chemotherapeutic (cytotoxic) agent or agents. Furthermore, the biomarker may be used to assist in the determination of therapy strategies in a subject including whether a compound of general formula I or a pharmaceutically acceptable derivative thereof is to be administered in combination with targeted therapy, endocrine therapy, radiotherapy, immunotherapy or surgical intervention, or a combination of these.

BUBR1 may also be used in combination with other biomarkers to predict the response to a compound of general formula I or a pharmaceutically acceptable derivative thereof and to determine treatment regimes. It may furthermore be used in combination with chemo-sensitivity testing to predict resistance and to determine treatment regimes. Chemo-sensitivity testing involves directly applying a compound of general formula I to cells taken from the subject, for example from a subject with haematological malignancies or accessible solid tumours, for example breast and head and neck cancers or melanomas, to determine the response of the cells to the compound.

Method of Treatment

The invention also involves in some aspects a method of treatment and BUBR1 for use in a method of treatment, wherein the level of BUBR1 is first established relative to a standard level or set of standard levels or pre-treatment initiation levels and then a compound of general formula I or a pharmaceutically acceptable derivative thereof as defined above, is administered if the level of BUBR1 in said sample is not lower than a standard value or set of standard values or has not decreased relative to pre-treatment initiation levels respectively. The compound of formula I or a pharmaceutically acceptable derivative thereof may be administered in a pharmaceutical composition, as is well known to a person skilled in the art. Suitable compositions and dosages are for example disclosed in WO 2004/103994 A1 pages 35-39, which are specifically incorporated by reference herein. Compositions for enteral administration, such as nasal, buccal, rectal or, especially, oral administration, and for parenteral administration, such as intravenous, intramuscular or subcutaneous administration, to warm-blooded animals, especially humans, are especially preferred. More particularly, compositions for intravenous administration are preferred.

The compositions comprise the active ingredient and a pharmaceutically acceptable carrier. An example of a composition includes, but is not limited to, the following: 5000 soft gelatin capsules, each comprising as active ingredient 0.05 g of one of the compounds of general formula (I), are prepared as follows: 250 g pulverized active ingredient is suspended in 2 liter Lauroglykol® (propylene glycol laurate, Gattefossé S. A., Saint Priest, France) and ground in a wet pulverizer to produce a particle size of about 1 to 3 μm. 0.419 g portions of the mixture are then introduced into soft gelatin capsules using a capsule-filling machine.

The invention also relates in one aspect to a method of treating a neoplastic or autoimmune disease, preferably cancer, by first increasing the level of BUBR1 in a subject that has a sample with a lower level of BUBR1 compared to a standard level or set of standard levels, or pre-treatment initiation levels, then treating the subject with a compound of general formula I or a pharmaceutically acceptable derivative as defined above. The level of BUBR1 may be increased by direct or indirect chemical or genetic means. Examples of such methods are treatment with a drug that results in increased BUBR1 expression and targeted delivery of viral, plasmid or peptide constructs, or antibody or siRNA or antisense to upregulate the level of BUBR1. For example viral or plasmid constructs may be used to increase the expression of BUBR1 in the cell. The subject may then be treated with a compound of general formula I or a pharmaceutically acceptable derivative thereof.

A compound of general formula I or a pharmaceutically acceptable derivative thereof can be administered alone or in combination with one or more other therapeutic agents. Possible combination therapy may take the form of fixed combinations, or the administration of a compound of the invention and one or more other therapeutic agents which are staggered or given independently of one another, or the combined administration of fixed combinations and one or more other therapeutic agents.

A compound of general formula I or a pharmaceutically acceptable derivative thereof can, besides or in addition, be administered especially for tumour therapy in combination with chemotherapy (cytotoxic therapy), targeted therapy, endocrine therapy, radiotherapy, immunotherapy, surgical intervention, or a combination of these. Long-term therapy is equally possible as is adjuvant therapy in the context of other treatment strategies, as described above. Other possible treatments are therapy to maintain the patient's status after tumour regression, or even chemo-preventive therapy, for example in patients at risk.

Kit and Device

In one aspect the invention relates to a kit, and in another aspect to a device, for predicting the response, preferably of a disease in a subject, to a compound of general formula I or a pharmaceutically acceptable derivative thereof as defined above, comprising reagents necessary for measuring the level of BUBR1 in a sample. Preferably, the reagents comprise a capture reagent comprising a detector for BUBR1 and a detector reagent.

The kit and device may also preferably comprise a comparator module which comprises a standard value or set of standard values to which the level of BUBR1 in the sample is compared. In a preferred embodiment, the comparator module is included in instructions for use of the kit. In another preferred embodiment the comparator module is in the form of a display device, for example a strip of colour or numerically coded material which is designed to be placed next to the readout of the sample measurement to indicate resistance levels. The standard value or set of standard values may be determined as described above.

The reagents are preferably antibodies or antibody fragments which selectively bind to BUBR1. These may for example be in the form of one specific primary antibody which binds to BUBR1 and a secondary antibody which binds to the primary antibody, and which is itself labelled for detection. The primary antibody may also be labelled for direct detection. The kits or devices may optionally also contain a wash solution(s) that selectively allows retention of the bound biomarker to the capture reagent as compared with other biomarkers after washing. Such kits can then be used in ELISA, western blotting, flow cytometry, immunohistochemical or other immunochemical methods to detect the level of the biomarker.

The reagents may also in another preferred embodiment be those that are capable of measuring the level of BUBR1 nucleic acids in a sample. Suitable samples are tissue or tumour tissue samples, sections of fixed and paraffin-embedded or frozen tissue or tumour tissue specimens, circulating tumour cells and blood and body liquid-derived samples. Preferably, the reagents comprise a labelled probe or primers for hybridisation to BUBR1 nucleic acid in the sample. Suitable detection systems, either based on PCR amplification techniques or detection of labelled probes, allow quantification of BUBR1 nucleic acid in the sample. This can be done i) in-situ on the specimen itself, preferably in sections from paraffin-em bedded or frozen specimens, ii) in extracts from tumour, tissue or blood-derived specimens, where suitable reagents selectively enrich for nucleic acids. The kits or devices enable the measurement and quantification of i) the amount of hybridised labelled probes to the specimens in-situ or ii) the amount of primer-based amplification products by methods based on specific physicochemical properties of the probes itself or the reporters attached to the primers.

Furthermore the device may comprise imaging devices or measurement devices (for example, but not restricted to, measurement of fluorescence) which further process the measured signals and transfer them into a scale in a comparator module.

More preferably the kit comprises a compound of general formula I, or a pharmaceutically acceptable derivative thereof as defined above. This compound may then be administered to the subject, in accordance with the level of the biomarker in the sample from the subject, as measured by the reagents comprised in the kit. Therefore the kit according to the invention may be used in the method of treatment according to the invention, as defined above. In an especially preferred embodiment the kit comprises a compound of the following formula or a pharmaceutically acceptable salt thereof

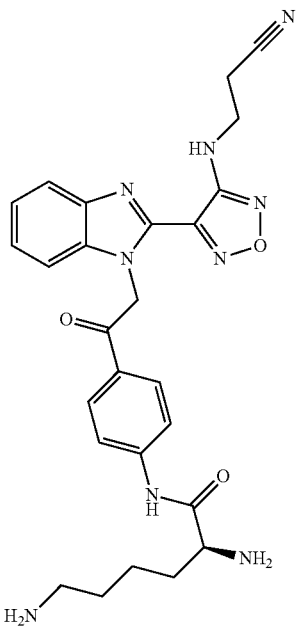 [SMILES: N#CCCNc1nonc1-c1nc2ccccc2n1CC(=O)c1ccc(NC(=O)[C@@H](N)CCCCN)cc1]

In a particularly preferred embodiment of the kit the salt is a dihydrochloride salt. In another aspect the invention relates to the use of such a kit as described above.

In the present specification the words "comprise" or "comprises" or "comprising" are to be understood as to imply the inclusion of a stated item or group of items, but not the exclusion of any other item or group of items.

Experimental Methodology

Immunofluorescent Staining of Cultured Cells

A549 human non-small cell lung cancer (NSCLC, ATCC reference number CCL-185) cells, HeLa cervical cancer cells (ATCC reference number CCL-2) and SKBR3 breast carcinoma cells (ATCC reference number HTB-30) were seeded at densities of 50% on round microscope coverslips and cultured for 24 hours in RPMI-1640 containing 10% FCS (also referred to as FBS) at 37° C., 5% $CO_2$. Compounds to be tested were dissolved in DMSO. The cell culture medium was replaced with medium containing the diluted compound(s) (paclitaxel, vinblastine, colchicine and nocodazole were purchased from Sigma-Aldrich) or vehicle. After treatment, coverslips were washed and cells were fixed in methanol/acetone (1:1) for 5 minutes at room temperature and subsequently incubated in blocking buffer (0.5% BSA and 0.1% TX-100 in PBS) for 30 minutes at room temperature. Specimens were then incubated with anti-alpha-tubulin antibody (Sigma, 1:2000) for 1 hour at room temperature in blocking buffer. After several washing steps cells were incubated with AlexaFluor-488 goat-anti-mouse IgG (Molecular Probes, 1:3000) for 1 hour at room temperature followed by several washing steps with blocking buffer. Specimens were then mounted with ProLong Gold antifade (Molecular Probes), sealed with nail polish and examined with a Leica immunofluorescence microscope. Images were captured with a cooled CCD-camera and processed by ImageJ software.

siRNA Transfection

In order to show BUBR1 is a biomarker of resistance, siRNA experiments were performed. For siRNA experiments to assess effects on tumour cell phenotype and numbers (FIG. 8), HeLa (ATCC reference CCL-2) cervical cancer cells were cultured at 37° C. and 5% $CO_2$ in DMEM with 10% FCS (Invitrogen). 1000 HeLa cells per well were seeded into black 384 well multititer plates (BD Falcon). Cells were reversely transfected with 20 nM non-targeting control siRNA (ON-Target-plus non-targeting pool D001810, Dharmacon) or a mixture of four BUBR1 siRNAs (ON-Target-plus Smartpool L-004101, Dharmacon, see sequence information below) using Dharmafect1 (Dharmacon, Thermo) transfection reagent. 48 hours after cell seeding and siRNA transfection, one replicate pair of siRNA clones was treated with BAL27862 (50 nM, 0.1% DMSO) and another replicate pair with control solution (0.1% DMSO) for 24 hours. The experiment was terminated by methanol-based fixation (−20° C., 5 min) and subsequent immunostaining (1 hour, room temperature) using alpha-tubulin (FITC labelled, 1:500, F2168, Sigma) and actin (TRITC-phalloidin, 1:3000, P1951, Sigma) antibodies as well as Hoe33342 DNA stain (1:8000, Sigma). Based on the immunostaining, the morphology of treated cells was analysed using a multiparametric approach (BD Pathway 855 fluorescence microscope; 20× objective) with appropriate software. The number of cells per well was also calculated based on Hoe33342 staining of nuclei. This enabled calculation of the fraction of cells displaying an untreated (normal) phenotype (in %).

For siRNA experiments to assess effects on BUBR1 expression levels by immunoblotting and effects on tumour cell proliferation and viability using the YO-PRO assay (FIGS. 7, 9,10 and 11), and Crystal Violet Assay (FIGS. 12 and 13), cells were seeded in 6 well plates at an appropriate density: HeLa (cervical cancer cells; ATCC reference CCL-2) 2.5E+04 (for YO-PRO) or 4.0E+04 (for Crystal Violet) cells per well, H460 (NSCLC cells; ATCC reference HTB-177) 5.0E+04 cells per well, MCF-7 (breast carcinoma cells; ATCC reference HTB-22) 2.4E+05 cells per well, Panc1 (pancreatic cancer cells, ATCC reference CRL-1469) and HCT116 (colon cancer cells, ATCC reference CCl-247) 8E+04 cells per well, and were cultured at 37° C. and 5% $CO_2$ in RPMI-1640 or DMEM containing 10% FCS (complete medium). Cells were transfected the following day with a mixture of four BUBR1 siRNAs (ON-Target-plus Smartpool L-004101, Dharmacon, see sequence information below), the four individual BUBR1 siRNAs (ON-Target-plus Set of four upgrade LU-004101) or non-targeting control siRNAs (ON-Target-plus non-targeting pool D001810, Dharmacon), using Hiperfect (Qiagen) for H460, Panc1 and HCT116 or Lipofectamine2000 (Invitrogen) for HeLa and MCF-7 according to manufacturer's instructions. The final concentration of siRNA was 10 nM (H460) or 20-30 nM (HeLa) or 20 nM (MCF-7, Panc1, HCT116). Cells were maintained at 37° C. and 5% $CO_2$ for 24 hours before compound treatment for 48 hours, followed by YO-PRO analysis, Crystal Violet Assay or extraction for immunoblot assay. ON-Target-plus siRNAs are dual-strand siRNAs, chemically modified to improve specificity for the desired target.

The sequences of the four BUBR1 siRNAs used were:

```
ON-TARGETplus BUBR1 siRNA #1
                                     SEQ ID. No. 3
5' GAUGGUGAAUUGUGGAAUA ON-TARGETplus BUBR1 siRNA #2
                                     SEQ ID. No. 4
5' GAAACGGGCAUUUGAAUAU ON-TARGETplus BUBR1 siRNA #3
                                     SEQ ID. No. 5
5' GCAAUGAGCCUUUGGAUAU ON-TARGETplus BUBR1 siRNA #4
                                     SEQ ID. No. 6
5' CAAUACAGCUUCACUGAUA
```

YO-PRO Assay of siRNA-treated Cells

BAL27862, dissolved in DMSO, was diluted into complete medium before addition to the cells at the indicated concentrations (final concentration DMSO 0.5%). Cells were incubated for 48 hours followed by YO-PRO analysis.

YO-PRO®-1 iodide is a membrane impermeable, fluorescent, monomeric cyanine, nucleic acid stain, which permits analysis of dying (e.g. apoptotic) cells without interfering with cell viability.

12.5 µl YO-PRO®-1 iodide (491/509)(Invitrogen/Molecular Probes, # Y-3603; 1 mM in DMSO) were added to 1 ml 5-times concentrated YO-PRO buffer (100 mM Na-citrate, pH 4.0; 134 mM NaCl) to produce the YO-PRO Mix. For the determination of cytotoxicity/apoptosis, 500 µl of YO-PRO Mix were added per well in 6 well plates (dilution 1:5), and incubated for 10 min at room temperature in the dark. The uptake of YO-PRO dye into cells was assessed by using a SpectraMax $M2^e$ plate reader (Molecular Devices) using 485 nm excitation and 538 nm emission at a cutoff of 530 nm. For the determination of overall effects on cell growth/total cell number, 500 µl of Lysis buffer (30 mM EDTA; 30 mM EGTA; 0.6% NP-40; in 0.33 times YO-PRO buffer) were added per well and incubated for 30 min at room temperature in the dark. Fluorescent read-out was performed in a SpectraMax $M2^e$ plate reader (Molecular Devices) using 485 nm excitation and 538 nm emission at a cut off of 530 nm. The % of dead cells was calculated as a percentage of the total remaining cell number.

Crystal Violet Assay of siRNA-treated Cells

Cells were incubated for 48 hours with DMSO or BAL27862 diluted in complete medium (final concentration DMSO 0.5%). After medium was removed, cells were fixed and stained by adding 1 ml Crystal Violet Staining (0.2% Crystal Violet in 50% Methanol) per well. Plates were incubated for 1 hour at room temperature. Subsequently the stain was decanted and plates were washed 4 times with double-distilled water. Plates were air-dried for several hours. Stain was dissolved by adding 2 ml buffer (0.1 M Tris pH 7.5, 0.2% SDS, 20% Ethanol) per well and shaking the plates. Absorbance at 590 nm was measured using a SpectraMax $M2^e$ plate reader (Molecular Devices). In order to subtract starting cell numbers, a control plate was fixed and stained on the same day the compound was added. Final results were calculated by subtracting the starting cell absorbance from that of control (DMSO) or compound treated cells. Values lower than zero indicate cell death.

Colony Outgrowth Assay:

Single cell suspensions of patient-derived tumour xenografts (maintained in nude mice) were prepared. For colony outgrowth assays, cells were plated in soft agar in 24-well plates according to the assay introduced by Hamburger & Salmon (Primary bioassay of human tumour stem cells, Science, 1977, 197:461-463). 2.0E+04-6.0E+04 cells in 0.2 mL medium containing 0.4% agar were plated out on a bottom layer of 0.75% agar. Test compounds were applied in 0.2 mL culture medium. Every 24-well plate contained untreated controls and samples in triplicates. Cultures were incubated at 37° C. and 7.5% $CO_2$ for 5-28 days. 24 hours prior to analysis, vital colonies were stained with a solution of metabolizable tetrazolium salt (Alley M C et al, Life Sci. 1982, 31:3071-3078) and were counted with an automatic image analysis system (Omnicon 3600, Biosys GmbH).

Relative drug effects were expressed by the ratio of the mean number of colonies in the treated wells and the control wells. $IC_{70}$-values were determined by plotting compound concentrations versus relative colony counts.

Quantitative Real-time PCR

HeLa cervical cancer and H460 NSCLC (ATCC Reference number HTB-177) cells were grown in 10 cm-dishes until they reached 80% confluency, followed by trypsinisation, pelleting and resuspension in 1 ml Trizol reagent (Invitrogen). Total RNA was isolated according to manufacturer's instructions. Real-time PCR was performed using the TaqMan RNA-to-Ct 1-step kit (Applied Biosystems, reference number 4392938) and gene expression assays (Applied Biosystems) with 100 ng RNA per reaction using the ABI Prism 7000 Sequence Detection System. The following gene expression assays were used: Assay ID Hs01084828_m1 for quantification of BUBR1 or Assay ID HS99999901_s1 for quantification of 18S-RNA. All samples were analysed in triplicate. Data analysis was performed using SDS software (Applied Biosystems). BUBR1 expression levels were normalised to 18S-RNA.

Generation and Crystal Violet Assay of BAL27862-Resistant Cell Lines

BAL27862-resistant sublines of human non-small cell lung cancer (H460 ATCC reference HTB-177; A549 ATCC reference CCL-185), ovarian cancer (SKOV3 ATCC reference HTB-77) lines were generated by long-term selection in complete cell culture medium (RPMI-1640 containing 10% FCS; Sigma-Aldrich) by stepwise increasing concentrations of BAL27862. Dependent on the cell line, the selection process was carried out for 8-12 months in order to achieve resistance factors (ratio of $IC_{50}$ of resistant cell line and appropriate wild-type cell line) between 3 and 11.6. The resistant sublines were expanded at the highest tolerated BAL27862 concentration and subsequently frozen and stored in liquid nitrogen.

Cells were seeded in 96 well plates at the following densities: A549: 2000, H460: 1000, SKOV3: 2000 and, after 24 hours incubation, were incubated for 72 hours with DMSO, BAL27862, colchicine, nocodazole, paclitaxel or vinblastine diluted in complete medium (final concentration DMSO max. 0.5%). After medium was removed, cells were fixed and stained by adding 50 µl Crystal Violet Staining (0.2% Crystal Violet in 50% Methanol) per well. Plates were incubated for 1 hour at room temperature. Subsequently the stain was decanted and plates were washed 4 times with double-distilled water. Plates were air-dried for several hours. Stain was dissolved by adding 100 µl buffer (0.1 M Tris pH 7.5, 0.2% SDS, 20% Ethanol) per well and shaking the plates. Absorbance at 590 nm was measured using a SpectraMax M2e plate reader (Molecular Devices). Antiproliferative $IC_{50}$ values were calculated from concentration response curves using GraphPad Prism software. Resistance factors were calculated as a ratio of BAL27862 $IC_{50}$ in the resistant line variant versus the $IC_{50}$ in the parental line.

Protein Extraction

Tumour cell extraction: Cells were washed with ice-cold PBS containing 1 mM phenylmethylsulfonyl fluoride (PMSF) and with ice-cold buffer containing 50 mM HEPES (pH 7.5), 150 mM NaCl, 25 mM β-glycerophosphate, 25 mM NaF, 5 mM EGTA, 1 mM EDTA, 15 mM pyrophosphate, 2 mM sodium orthovanadate, 10 mM sodium molybdate, leupeptin (10 µg/mL), aprotinin (10 µg/mL) and 1 mM phenylmethylsulphonyl fluoride (PMSF). Cells were extracted in the same buffer containing 1% NP-40. After homogenisation, lysates were clarified by centrifugation and frozen at −80° C.

Immunoblotting/Western Blotting

Immunoblotting was performed using 20 µg of total protein per lane. Total protein concentration was determined with the BCA Protein Assay (Pierce). Protein was separated on a 7.5% SDS-gel and transferred to a PVDF membrane using Semidry Blotting (90 min, 50 mA/gel). The primary antibodies used for immunoblotting were as follows:

BUBR1 Ab. No 1: $BUBR1_{CS}$ (available from Cell Signaling Technology, Inc, reference number 4116) origin: rabbit, polyclonal, dilution 1:1000, buffer conditions: 5% milk in PBS/0.1% Tween BUBR1 Ab. No 2: $BUBR1_{BD}$ (available from BD Transduction Laboratories, reference number 612502) origin: mouse, monoclonal, dilution 1:5000, buffer conditions: 3% BSA in PBS/0.1° A Tween Alpha-tubulin: (available from Sigma, reference number T5168) origin: mouse, monoclonal, dilution 1:10000, buffer conditions: 5% milk or 3% BSA in PBS/0.1% Tween Actin: (available from Chemicon, reference number MAB1501) origin: mouse, monoclonal, dilution 1:5000, buffer conditions: 5% milk or 3% BSA in PBS/0.1% Tween The secondary antibodies used for immunoblotting were peroxidase-conjugated goat anti-rabbit or goat anti-mouse (available from Jackson ImmunoResearch Laboratories INC: reference number 111-035-144 JIR and 115-035-146 JIR), dilution 1:5000, buffer conditions: 0.5% milk in PBS/ 0.1% Tween. Labelled bands were revealed using a Raytest Stella 3200 High Performance Imaging System.

Immunohistochemistry

Fixation of patient-derived tumour xenografts (maintained in nude mice) was performed in 10% neutral-buffered formalin containing 4% formaldehyde for 20-28 hours at room temperature. Fixed specimens were kept in a solution of 70% ethanol for a maximum of one week prior to dehydration and paraffin embedding according to a standard procedure, using the conditions listed below:

| Sequential Treatment | time (hours) |
| --- | --- |
| 70% EtOH | 1 |
| 80% EtOH | 2 |
| 99% EtOH | 1 |
| 100% Isopropanol | 0.5 |
| 100% Isopropanol | 1 |
| Xylol | 0.5 |
| Xylol | 1 |
| Xylol | 1 |
| Paraffin | 1 |
| Paraffin | 2 |
| Paraffin | 2 |

Paraffin sections of approximately 2 µm were cut and processed by using the automated immunostainer Benchmark XT® (Roche) running the standard processing steps. The visualisation of the specific antibody staining was done with DAB (3,3-diaminobenzidine) as chromogenic substrate at a concentration of 5 mg/m I. The following primary antibody and processing conditions were used for staining:

| Antibody Specification | Processing |
|---|---|
| Anti-BubR1, BD Transduction Lab, # 612503, mouse Mab | Cell conditioning 1 buffer from Roche for 30 minutes, antibody incubation at 37° C. for 32 minutes at a dilution of 1:200 |

DETAILED EXAMPLES

Example 1

A Distinct Mitotic Phenotype Induced by Compounds of General Formula I

Figure 2:
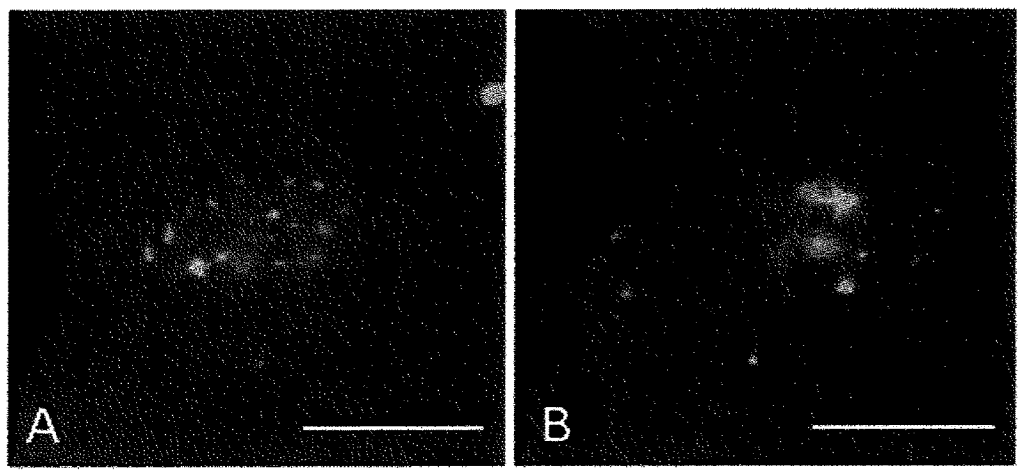
FIG. 2: Shows the treatment of A549 NSCLC cells with the Compounds B and C. The microtubules of mitotic or G2/M arrested A549 NSCLC cells were stained after 24 hours treatment with 80 nM or 20 nM of Compounds B and C, respectively. The white scale bar represents 10 micrometers.
A: treatment with 20 nM Compound C
B: treatment with 80 nM Compound B
Figure 3:
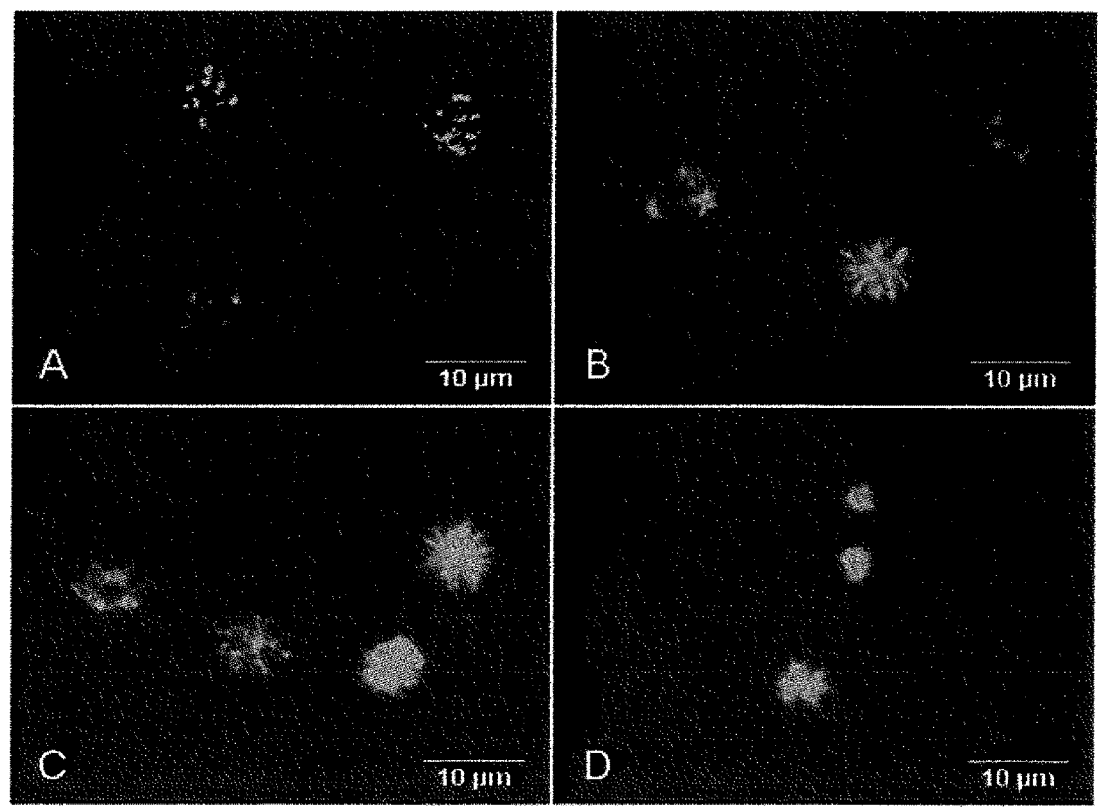
FIG. 3: Shows a comparison of treatment of cells with BAL27862 compared to conventional microtubule targeting agents. Microtubules of mitotic or G2/M arrested A549 NSCLC cells were stained after 24 hours of treatment with 50 nM of A: BAL27862; B: vinblastine; C: colchicine; D: paclitaxel. Stacks of images taken every 1 µm were processed by using ImageJ software.
Figure 4:
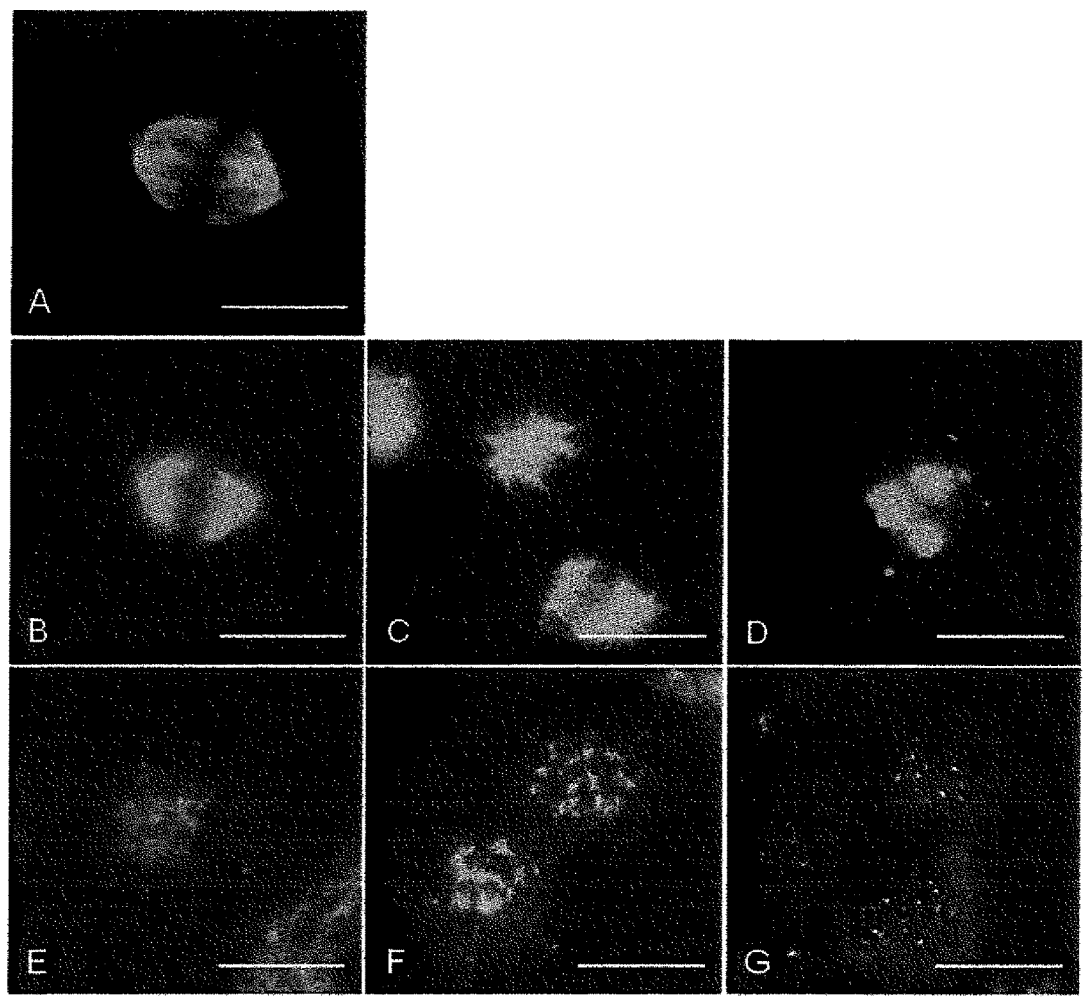
FIG. 4: Shows a comparison of treatment of A549 NSCLC cells with BAL27862 compared to nocodazole. Microtubules of mitotic or G2/M arrested cells were stained after 24 h of treatment with various concentrations of nocodazole (B, C & D) and BAL27862 (E, F & G). A: control, B: Nocodazole 50 nM, C: Nocodazole 100 nM, D: Nocodazole 200 nM, E: BAL27862 20 nM; F: BAL27862 30 nM and G: BAL27862 50 nM. The white scale bar represents 10 micrometers. Representative images of the microtubule phenotypes observed are shown.

Treatment with compound A (BAL27862) or with compound B or compound C, induced a highly reproducible and distinct microtubule phenotype in all tumour cell lines tested (shown for compound A in A549, HeLa and SKBR3 cells in FIG. 1, and for compound B and compound C in A549 cells in FIG. 2). In dividing cells an apparent fragmentation of the mitotic spindle occurred, resulting in the formation of dot-like structures (FIG. 1). This phenotype was shown to be distinct from that observed with conventional microtubule targeting agents, such as the microtubule stabiliser paclitaxel and the microtubule destabilisers vinblastine and colchicine (FIG. 3) and nocodazole (FIG. 4).

Example 2

Figure 5:
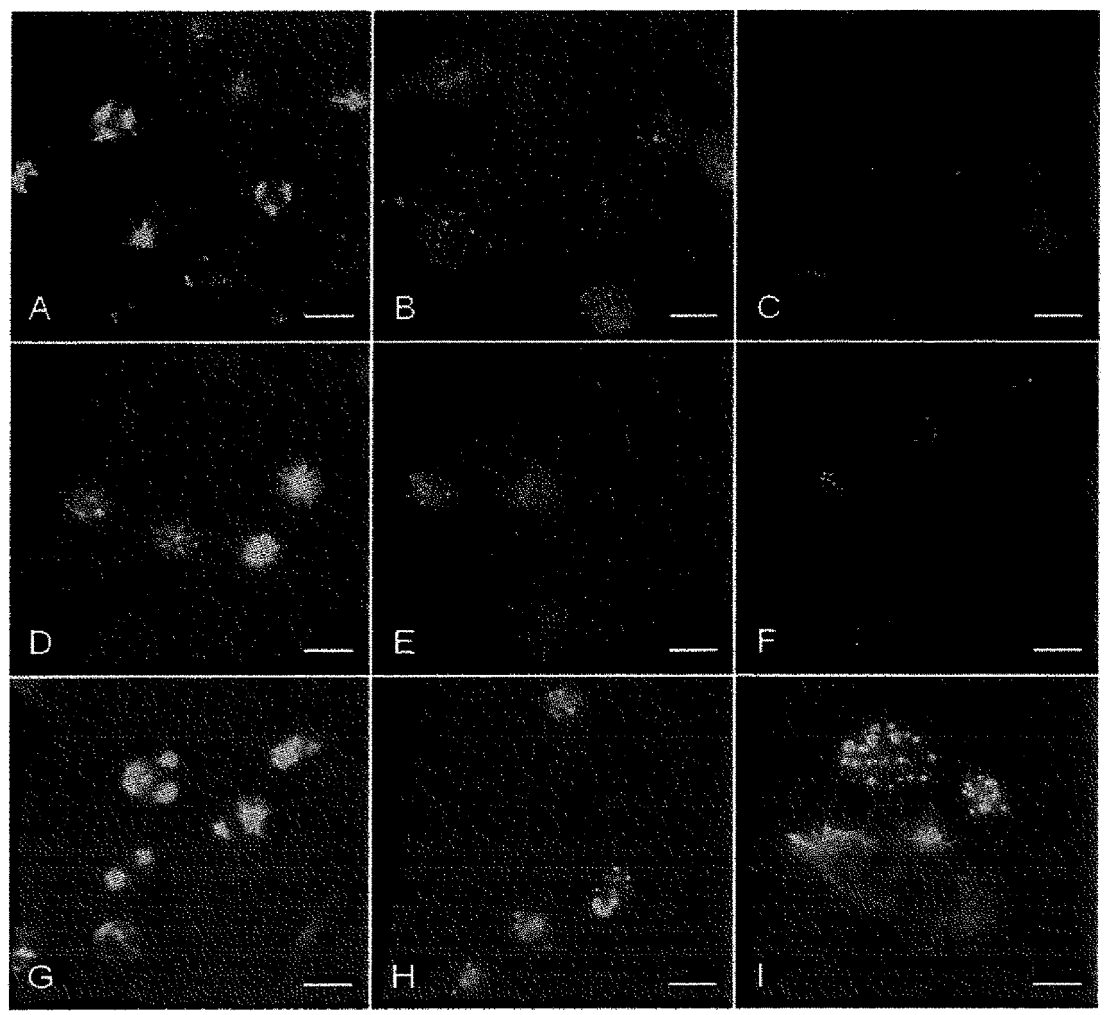
FIG. 5: Shows a combination of treatment with BAL27862 and conventional microtubule-targeting agents. Microtubules of mitotic or G2/M arrested A549 NSCLC cells were stained after treatment for the times indicated below. 50 nM BAL27862, 50 nM vinblastine, 50 nM colchicine and 25 nM paclitaxel were used. The white scale bar represents 10 micrometers.
A: 24 hours vinblastine treatment;
B: 24 hours vinblastine treatment with the final 4 hours including BAL27862;
C: 24 hours BAL27862 treatment with the final 4 hours including vinblastine.
D: 24 hours colchicine treatment;
E: 24 hours colchicine treatment with the final 4 hours including BAL27862;
F: 24 hours BAL27862 treatment with the final 4 hours including colchicine.
G: 24 hours paclitaxel treatment;
H: 24 hours paclitaxel treatment with the final 4 hours including BAL27862;
I: 24 hours BAL27862 treatment with the final 4 hours including paclitaxel.
Figure 6:
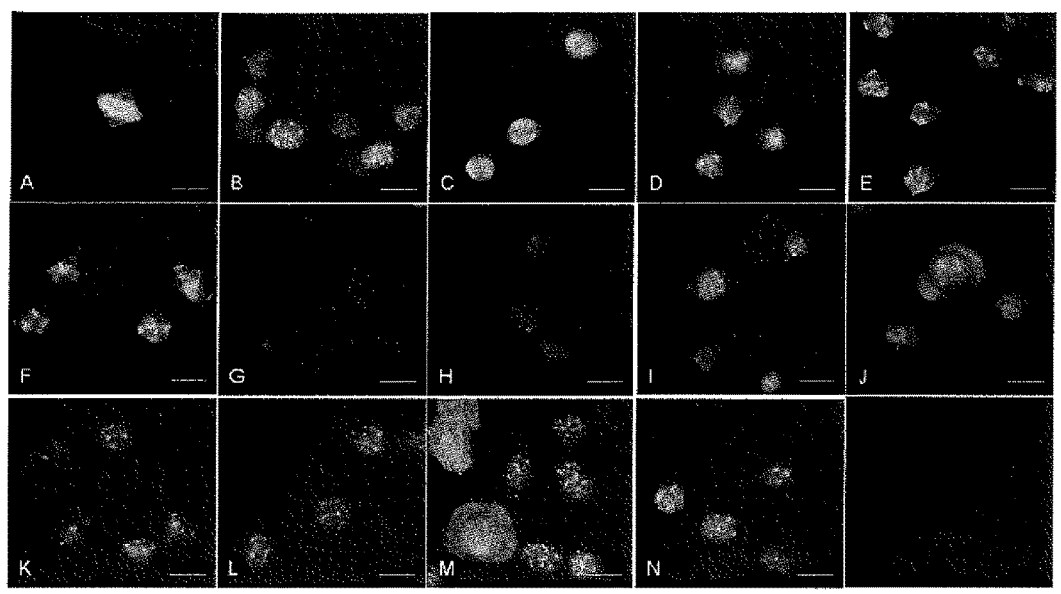
FIG. 6: Shows a combination of treatment with BAL27862 and nocodazole. Microtubules of mitotic or G2/M arrested A549 NSCLC cells were stained after treatment for the times indicated below. 25 nM BAL27862 and nocodazole at the concentrations indicated below were used. The white scale bar represents 10 micrometers.

BAL27862 Overcomes Microtubule Phenotype Induced by Conventional Microtubule-targeting Drugs in a Dominant Fashion In order to show the uniqueness of its activity on microtubules, BAL27862 was tested in combination with vinblastine, colchicine and paclitaxel (FIG. 5) and nocodazole (FIG. 6) using A549 cells. Treatment with vinblastine, colchicine, paclitaxel or nocodazole alone induced the mitotic microtubule phenotypes characteristic of these agents. However, combination treatment with BAL27862 for the last 4 hours resulted in disruption of the microtubule structures; creating a phenotype consistent with treatment of BAL27862 alone, despite the continued presence of vinblastine, colchicine, paclitaxel or nocodazole. In contrast, treating first with BAL27862 and subsequently for 4 hours in combination with vinblastine, colchicine, paclitaxel or nocodazole had no impact on the observed microtubule phenotype that was consistent with treatment with BAL27862.

These data demonstrate that compounds of formula I affect microtubule biology consistently, but in a different manner than conventional microtubule targeting agents.

Detailed Examples According to the Invention

Example 3 siRNA-mediated Down Regulation of BUBR1 Expression Suppresses the Antiproliferative Effect and Tumour Cell Death Induced by BAL27862 Treatment Through immunoblot analysis (using both BUBR1 Ab. No. 1 and 2) down regulation of BUBR1 expression using a pool of four BUBR1 siRNAs was shown to be very efficient in both HeLa cervical tumour and H460 NSCLC cell lines (FIG. 7).

Figure 8:
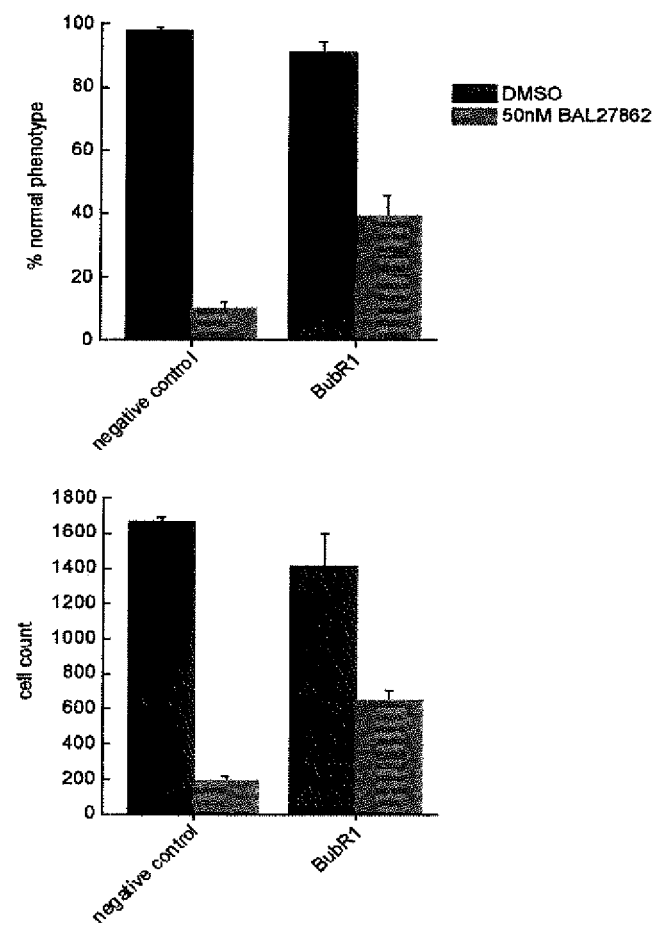

Strikingly, analysis of the effects of pooled BUBR1 siRNA treatment on HeLa cell number and the fraction of HeLa cells with a normal phenotype in the presence of BAL27862 indicated that BUBR1 was required for optimal effects (FIG. 8). Further analysis of the effects of reduced BUBR1 expression on HeLa cell proliferation and viability using the YO-PRO assay, indicated that, although loss of BUBR1 expression itself caused a slight reduction in proliferation rate, the antiproliferative effect of BAL27862 was dramatically reduced (FIG. 9, upper panel). Moreover, there was no increase in tumour cell death observed, as compared to a number of BAL27862-treated controls (FIG. 9, lower panel).

Figure 11:
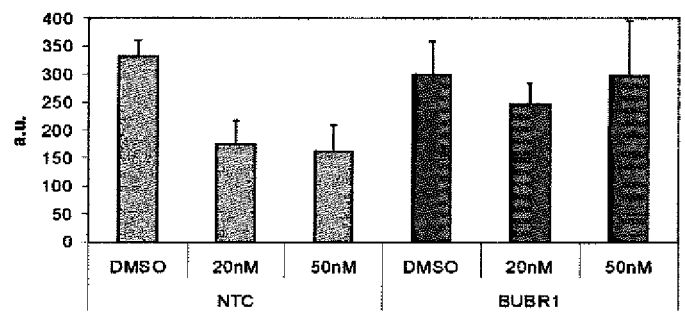
Figure 11:
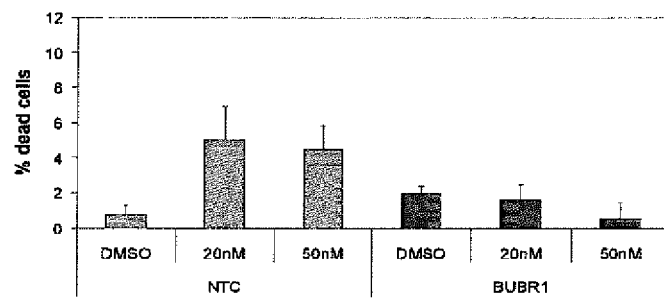
Figure 12:
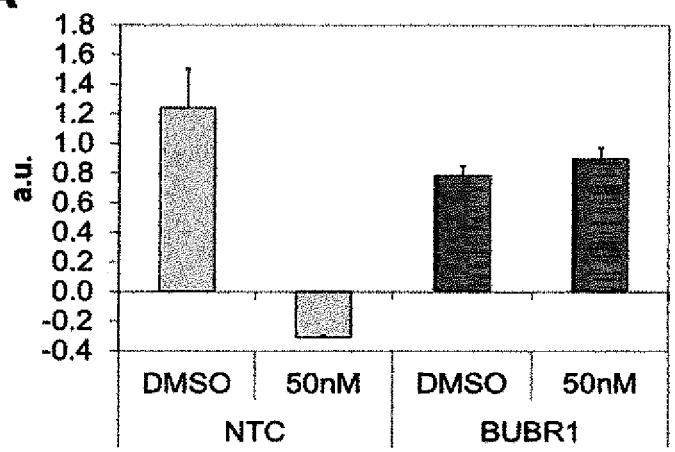
Figure 12:
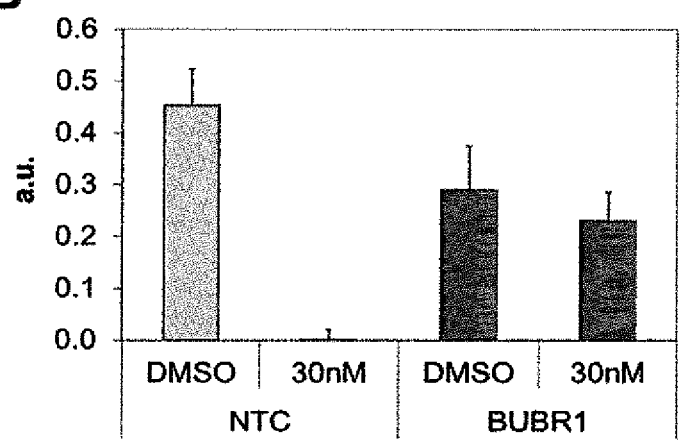
Figure 12:
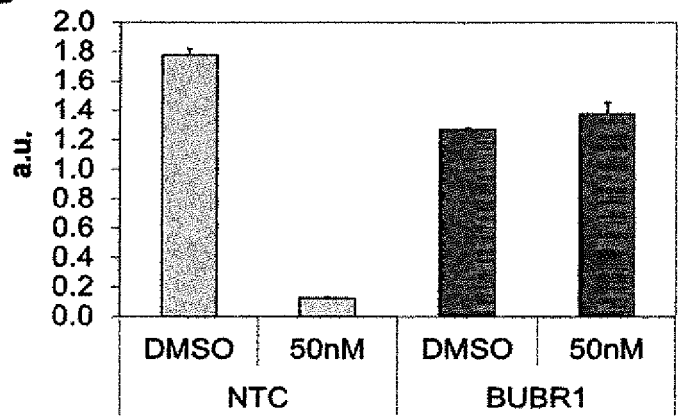

This effect was shown to be not cell-line or tumour-type-specific, as the same observation was made after treatment of H460 (FIG. 10) and MCF7 breast cancer cells (FIG. 11). Moreover, using an alternative method to analyse cellular proliferation (Crystal Violet assay), the same effects were again observed in HeLa, as well as in pancreatic (Panc1) and colon cancer (HCT116) cells (FIG. 12).

In order to control the specificity of the BUBR1 siRNA pool used for the experiments presented in FIGS. 7-12, the individual siRNAs contained within the pool were also evaluated. Treatment with all individual siRNAs decreased the effect of BAL27862 on cellular proliferation (as assessed by Crystal Violet assay)(FIG. 13, A). Importantly, the degree of reduction correlated with the efficiency of BUBR1 protein down regulation caused by each individual siRNA (compare A with B).

Example 4

Down Regulation of BUBR1 Expression is Observed in Tumour Lines Selected for BAL27862 Resistance In vitro selection for resistance to BAL27862 resulted in the generation of 3 relatively resistant tumour cell lines, with the following resistance factors versus parental lines (based on $IC_{50}$ determinations using the Crystal Violet assay): A549 (3.0 fold); SKOV3 resistant 1 (7.6 fold); SKOV3 resistant 2 (11.6 fold); H460 (5.3 fold) (Table 1).

TABLE 1

Resistance factors (ratio of $IC_{50}$ BAL27862-resistant cell line variant and $IC_{50}$ parental cell line)

| Treatment compound | A549 | H460 | SKOV3 resistant 1 | SKOV3 resistant 2 |
|---|---|---|---|---|
| BAL27862 | 3.0 | 5.3 | 7.6 | 11.6 |
| Colchicine | 0.9 | 1.6 | 2.0 | 2.8 |
| Nocodazole | 1.6 | 1.3 | 3.6 | 3.9 |
| Vinblastine | 2.3 | 4.6 | 15.7 | 17.8 |
| Paclitaxel | 0.06 | 0.3 | 0.4 | 0.5 |

In general these BAL27862-resistant cells exhibited a different level of response to other microtubule destabilising agents, such as colchicine, nocodazole and vinblastine, as compared to BAL27862; and indeed increased sensitivity to the microtubule stabiliser paclitaxel was observed in all lines (Table 1).

Extraction and immunoblot analysis of these lines (with BUBR1 Ab. No. 2, mouse monoclonal) indicated reduced expression of the BUBR1 protein as compared to the parental line (FIG. 14). This was maintained throughout resistance development in the SKOV3 cells (FIG. 15). These data show the association of the reduction in BUBR1 expression levels with acquired resistance to BAL27862.

Example 5

Association of Low BUBR1 Expression Levels with Patient-derived Tumour Cells Resistant to BAL27862 Treatment Based on colony outgrowth assays, using tumour cells derived from patient-derived tumours maintained as xenografts in mice, BAL27862-sensitive or relatively resistant tumour cells were identified from gastric and lung cancer (see Table 2). Concentrations at which 70% growth inhibition was observed versus controls ($IC_{70}$) are shown in Table 2. In this table, BAL27862-sensitive tumour cells have $IC_{70}$ values in the low nanomolar range, while BAL27862-resistant tumour cells are defined by $IC_{70}$ values >600 nanomolar. Paclitaxel and vinblastine data, using the same ex vivo assay, was also available for all tumour models. All were resistant to treatment with paclitaxel, while all were sensitive to treatment with vinblastine.

TABLE 2

| Tumour type | | Sensitive (S)/Resistant (R) | | |
|---|---|---|---|---|
| | | BAL27862 | Paclitaxel | Vinblastine |
| Gastric | GXF251 | S | R | S |
| | GXF97 | R | R | S |
| Lung | LXFL529 | S | R | S |
| | LXFA629 | R | R | S |

Immunohistochemistry analysis was performed in order to measure tumour cell BUBR1 protein expression in the same tumours maintained as xenografts. Analysis of whole-tumour BUBR1 levels indicated that BUBR1 levels varied between the different tumours (FIG. 16).

Based on the colony outgrowth assay and the same $IC_{70}$ criteria, there was no association between paclitaxel or vinblastine resistance and low BUBR1 expression levels. This is evident since for the gastric tumour type, both models were resistant to paclitaxel and yet for GXF 97 the BUBR1 levels were much lower than in GXF 251. The same lack of association was true for the vinca alkaloid, vinblastine in the gastric model, since both these tumours were sensitive to vinblastine. This lack of association was repeated in the lung tumour models. Thus BUBR1 levels were shown to be unsuitable as a reliable biomarker of resistance to the conventional microtubule agents paclitaxel and vinblastine in patient-derived tumour models.

Surprisingly, in contrast, when the BAL27862 resistance data, as defined by the colony outgrowth assay, was compared with the BUBR1 level, BUBR1 expression was shown to be lower only in the resistant tumours and not in the sensitive tumours derived from the same tumour histotype (compare FIG. 16 with Table 2). Low BUBR1 levels were therefore consistently indicative of resistance to BAL2786. Thus BUBR1 levels were shown to be a biomarker of resistance for the compound according to the invention, BAL27862.

Example 6

BUBR1 RNA Versus Protein Expression Levels

In order to show that BUBR1 RNA expression levels reflect protein expression levels, and hence that RNA expression levels can be used in the prediction of resistance to BAL27862, expression levels were measured on both the RNA and protein levels as follows. Whole cell protein extracts were prepared from HeLa and H460 cell lines and analysed by immunoblot for BUBR1 protein expression (FIG. 17, B). RNA samples were prepared from the same cell passage, and quantitative RT-PCR was performed (FIG. 17, A). Comparison of the immunoblot data (B) and the RT-PCR data (A), indicated that there was a good correlation between protein and RNA expression levels for BUBR1 in these lines.

LIST OF ABBREVIATIONS

A549 human non-small cell lung cancer cell line
BCA bicinchoninic acid
Bcl-2 B-cell lymphoma 2 protein
BRCA1 breast cancer type 1 susceptibility protein
BrdU bromodeoxyuridine
BSA bovine serum albumin
CCD charged-coupled device
cDNA complementary deoxyribonucleic acid
CA-125 cancer antigen 125
CREST limited scleroderma syndrome
DAB 3,3-diaminobenzidine
DMSO Dimethylsulphoxide
DMEM Dulbecos modified essential medium
DNA Deoxyribonucleic acid
dUTP 2"-Deoxyuridine 5"-Triphosphate
EDTA/EGTA Ethylendiamintetraacetate/Ethyleneglycol-bis (β-aminoethyl)-N,N,N',N'-tetraacetate
ELISA enzyme-linked immunosorbent assay
ErbB-2 human epidermal growth factor receptor 2
EtOH Ethanol
FACS fluorescence activated cell scan/sorting
FCS/FBS foetal calf/foetal bovine serum
G2/M transition from G2 to the mitotic phase in the cell cycle
GXF 251 patient-derived gastric cancer
GXF 97 patient-derived gastric cancer
HCT116 human colorectal carcinoma cell line
HeLa human squamous cell cancer cell line
HEPES 4-(2-Hydroxyethyl)piperazine-1-ethanesulphonic acid
Hoe33342 2'-(4'-Ethoxyphenyl)-5-(4-methylpiperazin-1-yl)-2,5'-bis-1H-benzimidazole trihydrochloride trihydrate
H460 human non-small-cell lung cancer cell line
IgA immunoglobulin A
IgG immunoglobulin G
IHC immunohistochemistry
ISET Isolation by size of epithelial tumor cells
LXFA 629 patient-derived lung carcinoma cells
LXFL 529 patient-derived lung carcinoma cells
MALDI matrix-assisted-laser-desorption/ionisation mass-spectrometry
MALDI-TOF matrix-assisted-laser-desorption/ionisation-time-of-flight-mass-spectrometry
MCF-7 human mammary carcinoma cell line
mRNA messenger ribonucleic acid
MTS 3-(4,5-dimethylthiazol-2-yl)-5-(3-carboxymethoxyphenyl)-2-(4-sulphophenyl)-2H-tetrazolium
NaCl Sodium chloride
NaF Sodium fluoride
NCBI National center for Biotechnology Information
NSCLC non-small cell lung cancer
NP40 Nonidet P40
NTC non-template control PBS phosphate buffered saline
PCR polymerase chain reaction
P-gp P-glycoprotein
PMSF phenylmethylsulphonyl fluoride
PSA prostate-specific antigen
PVDF Polyvinylidene fluoride
RANO response assessment for high-grade gliomas
RECIST response evaluation criteria in solid tumours
READS restriction enzyme amplification of digested cDNAs
RPMI-1640 cell culture medium used for culturing transformed and non-transformed eukaryotic cells and cell lines
RT-PCR real-time polymerase chain reaction SAGE serial analysis of gene expression
SDS sodium dodecyl sulphate
SELDI surface enhanced laser desorption/Ionization mass-spectrometry
SELDI-TOF surface enhanced laser desorption/Ionisation-time-of-flight-mass-spectrometry
SEQ. ID No. sequence identification number
siRNA small inhibitory ribonucleic acid
SKBR3 human mammary carcinoma cell line
SKOV3 human ovarian carcinoma cell line
TUNEL terminal deoxynucleotidyl transferase dUTP nick end labeling
TX-100 Triton-X100
YO-PRO fluorescent, monomeric cyanine, nucleic acid stain

What we claim:

1. A method of treating a neoplastic disease in a patient in need thereof, comprising the steps of:
   a) obtaining a sample of biologic material from the body of said patient;
   b) determining the level of the BUBR1 proteins or BUBR1 nucleic acid in said sample; and
   c) destabilizing microtubules in said patient by administering to said patient a therapeutically effective amount of a compound according to formula I:

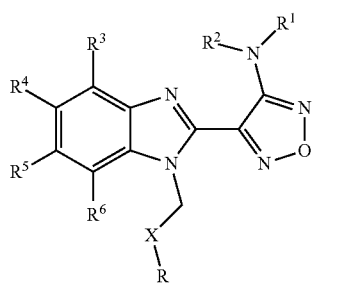

(I)

wherein R represents phenyl or pyridinyl,
wherein said phenyl is optionally substituted by one or two substituents independently selected from alkyl, halo-lower alkyl, hydroxy-lower alkyl, lower alkoxy-lower alkyl, acyloxy-lower alkyl, phenyl, hydroxy, lower alkoxy, hydroxy-lower alkoxy, lower alkoxy-lower alkoxy, phenyl-lower alkoxy, lower alkylcarbonyloxy, amino, monoalkylamino, dialkylamino, lower alkoxycarbonylamino, lower alkylcarbonylamino, substituted amino wherein the two substituents on nitrogen form together with the nitrogen heterocyclyl, lower alkylcarbonyl, carboxy, lower alkoxycarbonyl, cyano, halogen, and nitro; and wherein two adjacent substituents are methylenedioxy,
and wherein said pyridinyl is optionally substituted by lower alkoxy, amino or halogen;
X represents a group C=Y, wherein Y is oxygen or nitrogen substituted by hydroxy or lower alkoxy; or when R1 is phenyl or pyridinyl, X is additionally oxygen;
R$^1$ represents hydrogen, lower alkylcarbonyl, hydroxy-lower alkyl or cyano-lower alkyl;
R$^2$, R$^3$ and R$^6$ represent hydrogen;
R$^4$ and R$^5$, independently of each other, represent hydrogen, lower alkyl or lower alkoxy;
or R$^4$ and R$^5$ together represent methylenedioxy;
or a pharmaceutically acceptable derivative thereof;
and wherein said prefix lower denotes a radical having up to 7 carbon atoms,
if the level of BUBR1 proteins or BUBR1 nucleic acid in said sample is not lower than a standard value or set of standard values for the level of BUBR1 proteins or BUBR1 nucleic acids; and
wherein the neoplastic disease is selected from the group consisting of epithelial neoplasms, squamous cell neoplasms, basal cell neoplasms, transitional cell papillomas and carcinomas, adenomas and adenocarcinomas, adnexal and skin appendage neoplasms, mucoepidermoid neoplasms, cystic neoplasms, mucinous and serous neoplasms, ducal-, lobular and medullary neoplasms, acinar cell neoplasms, complex epithelial neoplasms, specialized gonadal neoplasms, paragangliomas and glomus tumours, naevi and melanomas, soft tissue tumours and sarcomas, fibromatous neoplasms, myxomatous neoplasms, lipomatous neoplasms, myomatous neoplasms, complex mixed and stromal neoplasms, fibroepithelial neoplasms, synovial like neoplasms, mesothelial neoplasms, germ cell neoplasms, trophoblastic neoplasms, mesonephromas, blood vessel turnouts, lymphatic vessel tumours, osseous and chondromatous neoplasms, giant cell tumours, miscellaneous bone tumours, odontogenic tumours, gliomas, neuroepitheliornatous neoplasms, meningiomas, nerve sheath tumours, granular cell turnouts and alveolar soft part sarcomas, Hodgkin's and non-Hodgkin's lymphomas, other lymphoreticular neoplasms, plasma cell turnouts, mast cell tumours, immunoproliferative diseases, leukemias, miscellaneous myeloproliferative disorders, lymphoproliferative disorders and myelodysplastic syndromes.

2. The method of claim 1, wherein said patient is an animal or human being and the level of BUBR1 proteins or BUBR1 nucleic acids is measured ex vivo in the sample taken from said animal or human being.

3. The method according to claim 2, wherein said sample is derived from normal tissue, tumor tissue, circulating tumor cells, plasma or whole blood.

4. The method according to claim 3, wherein said sample is derived from tumor tissue or circulating tumor cells.

5. The method of claim 1, wherein a lower level of BUBR1 proteins or BUBR1 nucleic acids in the sample relative to a standard value or a set of standard values predicts resistance to treating said disease with said compound of formula I, or a pharmaceutically acccptable derivative thereof.

6. The method of claim 5, wherein the determination of a lower level of BUBR1 proteins or BUBR1 nucleic acids in said sample obtained from the animal or human being is carried out by comparing the measured BUBR1 protein level or BUBR1 nucleic acid level in said sample i) relative to a standard value or a set of standard values of levels of BUBR1 proteins or BUBR1 nucleic acids from samples from other subjects having the same tumour histotype as said animal or human being; or
ii) relative to a standard value or a set of standard values of levels of BUBR1 proteins or BUBR1 nucleic acids from a sample or samples of levels of BUBR1 from normal tissue; or
iii) relative to a standard value or a set of standard values of BUBR1 proteins or BUBR1 nucleic acids from samples obtained from the same patient before initiation of treatment with the compound of formula I or a pharmaceutically acceptable derivative thereof.

7. The method of claim 1, wherein the protein sequence of BUBR1 proteins is selected from the groups consisting of SEQ ID No. 1 and homologues, mutant forms, allelic variants, isoforms, splice variants and proteins with sequences having at least 75% identity to SEQ ID 1.

8. The method according to claim 1, wherein the nucleic acid sequence representing BUBR1 nucleic acids is selected from the group consisting of SEQ ID No. 2 and sequences having at least about 75% identity to SEQ ID No. 2.

9. The method of claim 1, wherein the compound is a compound of general formula I wherein
R represents phenyl or pyridinyl
wherein phenyl is optionally substituted by one or two substituents independently selected from lower alkyl, lower alkoxy, amino, acetylamine, halogen and nitro; and wherein pyridinyl is optionally substituted by amino or halogen;
X represents a group C=O;
$R^1$ represents hydrogen or cyano-lower alkyl;
$R^2$, $R^3$, $R^4$, $R^5$ and $R^6$ represent hydrogen;
or a pharmaceutically acceptable derivative thereof,
and wherein said prefix lower denotes a radical having up to and including a maximum of 7 carbon atoms.

10. The method according to claim 9, wherein said patient is an animal or human being and the level of BUBR1 proteins or BUBR1 nucleic acids is measured ex vivo in a sample taken from the animal or human being's body.

11. The method according to claim 10, wherein said sample is derived from normal tissue, tumor tissue, circulating tumor cells, plasma or whole blood.

12. The method according to claim 11, wherein said sample is derived from tumor tissue or circulating tumor cells.

13. The method of claim 9, wherein a lower level of BUBR1 proteins or BUBR1 nucleic acids in a sample obtained from said animal or human being relative to a standard value or a set of standard values predicts resistance to a therapy with compounds of formula I or a pharmaceutically acceptable derivative thereof.

14. The method of claim 13, wherein the determination of a lower level of BUBR1 in said sample obtained from the animal or human being is carried out by comparing the measured BUBR1 protein level or BUBR1 nucleic acids in said sample
i) relative to a standard value or a set of standard values of levels of BUBR1 proteins or BUBR1 nucleic acids from samples from other subjects having the same tumour histotype as said animal or human being; or
ii) relative to a standard value or a set of standard values of levels of BUBR1 proteins or BUBR1 nucleic acids from a sample or samples of levels of BUBR1 from normal tissue; or
iii) relative to a standard value or a set of standard values of BUBR1 proteins or BUBR1 nucleic acids from samples obtained from the same patient before initiation of treatment with the compound of formula I or a pharmaceutically acceptable derivative thereof.

15. The method of claim 9, wherein the BUBR1 proteins or BUBR1 nucleic acids are used as biomarker to select subjects suffering or predisposed to suffering from a disease for treatment with a compound of general formula I or a pharmaceutically acceptable derivative thereof.

16. The method of claim 15, wherein the BUBR1 proteins or BUBR1 nucleic acids are used as biomarker to select subjects suffering or predisposed to suffering from cancer for treatment with a compound of general formula I or a pharmaceutically acceptable derivative thereof.

17. The method of claim 1, wherein the BUBR1 proteins or BUBR1 nucleic acids are used as biomarker to select subjects suffering or predisposed to suffering from a disease for treatment with a compound of general formula I or a pharmaceutically acceptable derivative thereof.

18. The method of claim 17, wherein the BUBR1 proteins or BUBR1 nucleic acids are used as biomarker to select subjects suffering or predisposed to suffering from cancer for treatment with a compound of general formula I or a pharmaceutically acceptable derivative thereof.

19. The method of claim 1, wherein the compound is represented by the following formula

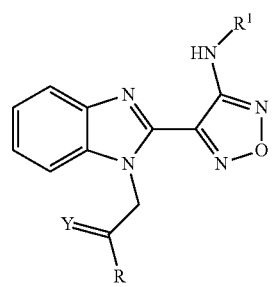

wherein R, Y and R1 are defined as follows:

| R | Y | $R^1$ |
|---|---|---|
| H₂N–⟨phenyl⟩– | O | CH₂CH₂CN |
| H₂N–⟨phenyl⟩– | O | H |
| H₂N–⟨pyridinyl⟩– | O | CH₂CH₂CN | or pharmaceutically aceeptable derivative thereof.

20. The method of claim 1, wherein the compound is

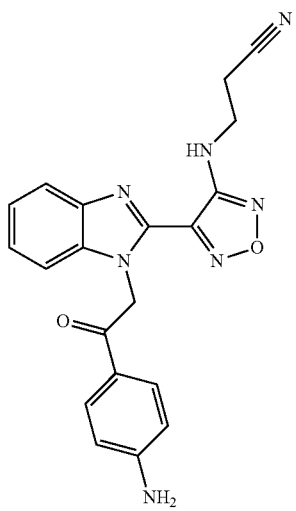 [SMILES: N#CCCNc1nonc1-c1nc2ccccc2n1CC(=O)c1ccc(N)cc1]

or a pharmaceutically acceptable derivative thereof.

21. The method of claim 20, wherein the pharmaceutically acceptable derivative is selected from the group consisting of a salt, solvate, pro-drug, salt of a pro-drug, polymorph and isomer of the compound of general formula I as defined in claim 20.

22. The method of claim 21, wherein the pharmaceutically acceptable pro-drug is an amide formed from an amino group present within the R group of the compound of formula I as defined in claim 1 and the carboxy group of glycine, alanine or lysine.

23. The method of claim 20, wherein the disease is breast cancer.

24. The method of claim 20, wherein the disease is ovarian cancer.

25. The method of claim 20, wherein the disease is colorectal cancer.

26. The method of claim 20, wherein the disease is lung cancer.

27. The method of claim 20, wherein the disease is liver cancer.

28. The method of claim 20, wherein the disease is gastric cancer.

29. The method of claim 20, wherein the disease is pancreatic cancer.

30. The method of claim 20, wherein the disease is a hematological malignancy.

31. The method of claim 20, wherein the disease is kidney cancer.

32. The method of claim 20, wherein the disease is skin cancer.

33. The method of claim 20, wherein the disease is brain cancer.

34. The method of claim 20, wherein the disease is prostate cancer.

35. The method of claim 20, wherein the disease is head and neck cancer.

36. The method of claim 20, wherein the disease is a sarcomas.

37. The hod of claim 20, wherein the disease is glioma.

38. The method of claim 1, wherein the pharmaceutically acceptable derivative is selected from the group consisting of a salt, solvate, pro-drug, salt of a pro-drug, polymorph and isomer of the compound of general formula I.

39. The method of claim 38, wherein the pharmaceutically acceptable pro-drug is an amide formed from an amino group present within the R group of the compound of formula I as defined in claim 1 and the carboxy group of glycine, alanine or lysine.

40. The method of claim 1, wherein the compound is

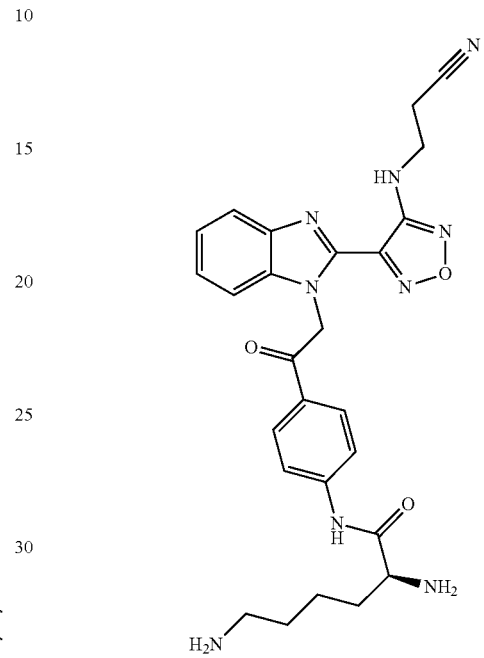

or a pharmaceutically acceptable salt thereof.

41. The method of claim 40, wherein the disease is breast cancer.

42. The method of claim 40, wherein the disease is ovarian cancer.

43. The method of claim 40, wherein the disease is colorectal cancer.

44. The method of claim 40, wherein the disease is lung cancer.

45. The method of claim 40, wherein the disease is liver cancer.

46. The method of claim 40, wherein the disease is gastric cancer.

47. The method of claim 40, wherein the disease is pancreatic cancer.

48. The method of claim 40, wherein the disease is a hematological malignancy.

49. The method of claim 40, wherein the disease is kidney cancer.

50. The method of claim 40, wherein the disease is skin cancer.

51. The method of claim 40, wherein the disease is brain cancer.

52. The method of claim 40, wherein the disease is prostate cancer.

53. The method of claim 40, wherein the disease is head and neck cancer.

54. The method of claim 40, wherein the disease is a sarcomas.

55. The method of claim 40, wherein the disease is glioma.

56. The method according to claim 1, wherein step a) comprises determining the level of BUBR1 proteins.

57. The method of claim 1, wherein the neoplastic disease is selected from the group consisting of breast cancer, prostate cancer, cervical cancer, ovarian cancer, gastric cancer, colorectal cancer, pancreatic cancer, liver cancer, brain cancer, neuroendocrine cancer, lung cancer, kidney cancer, hematological malignancies, melanoma and sarcomas.

58. The method of claim 1, wherein the neoplastic disease is selected from the group consisting of ovarian cancer, breast cancer, gastric cancer, pancreatic cancer, colon cancer, lung cancer and cervical cancer.

59. The method of claim 1, wherein the neoplastic disease is selected from the group consisting of gastric cancer and lung cancer.

60. The method of claim 1, wherein the disease is a cancer selected from cancers in telins of the organs and parts of the body affected, selected from the breast, cervix, ovaries, colon, rectum, colorectal cancer, lung, endocrine system, bone, adrenal gland, thymus, liver, stomach, intestine, gastric cancer, pancreas, bone marrow, hematological malignancies, bladder, urinary tract, kidneys, skin, thyroid, brain, head, neck, prostate and testis.

* * * * *

UNITED STATES PATENT AND TRADEMARK OFFICE
CERTIFICATE OF CORRECTION

PATENT NO.       : 9,970,938 B2
APPLICATION NO.  : 15/060998
DATED            : May 15, 2018
INVENTOR(S)      : Heidi Alexandra Lane et al.

Page 1 of 1

It is certified that error appears in the above-identified patent and that said Letters Patent is hereby corrected as shown below:

In the Claims

At Column 62, Line 37, "turnouts" should be replaced with "tumours."

At Column 62, Line 40, "neuroepitheliornatous" should be replaced with "neuroepitheliomatous."

At Column 62, Lines 41 and 44, "turnouts" should be replaced with "tumours."

At Column 63, Line 28, "acetylamine" should be replaced with "acetylamino."

At Column 67, Line 18, "telins" should be replaced with "terms."

Signed and Sealed this
Tenth Day of July, 2018

Andrei Iancu
*Director of the United States Patent and Trademark Office*

```
                        SEQUENCE LISTING

<160> NUMBER OF SEQ ID NOS: 6

<210> SEQ ID NO 1
<211> LENGTH: 1050
<212> TYPE: PRT
<213> ORGANISM: Homo sapiens

<400> SEQUENCE: 1

Met Ala Ala Val Lys Lys Glu Gly Gly Ala Leu Ser Glu Ala Met Ser
1               5                   10                  15

Leu Glu Gly Asp Glu Trp Glu Leu Ser Lys Glu Asn Val Gln Pro Leu
            20                  25                  30

Arg Gln Gly Arg Ile Met Ser Thr Leu Gln Gly Ala Leu Ala Gln Glu
        35                  40                  45

Ser Ala Cys Asn Asn Thr Leu Gln Gln Gln Lys Arg Ala Phe Glu Tyr
    50                  55                  60

Glu Ile Arg Phe Tyr Thr Gly Asn Asp Pro Leu Asp Val Trp Asp Arg
65                  70                  75                  80

Tyr Ile Ser Trp Thr Glu Gln Asn Tyr Pro Gln Gly Gly Lys Glu Ser
                85                  90                  95

Asn Met Ser Thr Leu Leu Glu Arg Ala Val Glu Ala Leu Gln Gly Glu
            100                 105                 110

Lys Arg Tyr Tyr Ser Asp Pro Arg Phe Leu Asn Leu Trp Leu Lys Leu
        115                 120                 125

Gly Arg Leu Cys Asn Glu Pro Leu Asp Met Tyr Ser Tyr Leu His Asn
    130                 135                 140

Gln Gly Ile Gly Val Ser Leu Ala Gln Phe Tyr Ile Ser Trp Ala Glu
145                 150                 155                 160

Glu Tyr Glu Ala Arg Glu Asn Phe Arg Lys Ala Asp Ala Ile Phe Gln
                165                 170                 175

Glu Gly Ile Gln Gln Lys Ala Glu Pro Leu Glu Arg Leu Gln Ser Gln
            180                 185                 190

His Arg Gln Phe Gln Ala Arg Val Ser Arg Gln Thr Leu Leu Ala Leu
        195                 200                 205

Glu Lys Glu Glu Glu Glu Val Phe Glu Ser Ser Val Pro Gln Arg
        210                 215                 220

Ser Thr Leu Ala Glu Leu Lys Ser Lys Gly Lys Lys Thr Ala Arg Ala
225                 230                 235                 240

Pro Ile Ile Arg Val Gly Gly Ala Leu Lys Ala Pro Ser Gln Asn Arg
                245                 250                 255

Gly Leu Gln Asn Pro Phe Pro Gln Gln Met Gln Asn Asn Ser Arg Ile
            260                 265                 270
```

```
Thr Val Phe Asp Glu Asn Ala Asp Glu Ala Ser Thr Ala Glu Leu Ser
            275                 280                 285

Lys Pro Thr Val Gln Pro Trp Ile Ala Pro Met Pro Arg Ala Lys
    290                 295                 300

Glu Asn Glu Leu Gln Ala Gly Pro Trp Asn Thr Gly Arg Ser Leu Glu
305                 310                 315                 320

His Arg Pro Arg Gly Asn Thr Ala Ser Leu Ile Ala Val Pro Ala Val
                325                 330                 335

Leu Pro Ser Phe Thr Pro Tyr Val Glu Thr Ala Gln Gln Pro Val
                340                 345                 350

Met Thr Pro Cys Lys Ile Glu Pro Ser Ile Asn His Ile Leu Ser Thr
        355                 360                 365

Arg Lys Pro Gly Lys Glu Gly Asp Pro Leu Gln Arg Val Gln Ser
    370                 375                 380

His Gln Gln Ala Ser Glu Glu Lys Lys Glu Lys Met Met Tyr Cys Lys
385                 390                 395                 400

Glu Lys Ile Tyr Ala Gly Val Gly Glu Phe Ser Phe Glu Glu Ile Arg
                405                 410                 415

Ala Glu Val Phe Arg Lys Lys Leu Lys Glu Gln Arg Glu Ala Glu Leu
                420                 425                 430

Leu Thr Ser Ala Glu Lys Arg Ala Glu Met Gln Lys Gln Ile Glu Glu
            435                 440                 445

Met Glu Lys Lys Leu Lys Glu Ile Gln Thr Thr Gln Gln Glu Arg Thr
        450                 455                 460

Gly Asp Gln Gln Glu Glu Thr Met Pro Thr Lys Glu Thr Thr Lys Leu
465                 470                 475                 480

Gln Ile Ala Ser Glu Ser Gln Lys Ile Pro Gly Met Thr Leu Ser Ser
                485                 490                 495

Ser Val Cys Gln Val Asn Cys Cys Ala Arg Glu Thr Ser Leu Ala Glu
            500                 505                 510

Asn Ile Trp Gln Glu Gln Pro His Ser Lys Gly Pro Ser Val Pro Phe
            515                 520                 525

Ser Ile Phe Asp Glu Phe Leu Leu Ser Glu Lys Lys Asn Lys Ser Pro
    530                 535                 540

Pro Ala Asp Pro Pro Arg Val Leu Ala Gln Arg Arg Pro Leu Ala Val
545                 550                 555                 560

Leu Lys Thr Ser Glu Ser Ile Thr Ser Asn Glu Asp Val Ser Pro Asp
                565                 570                 575

Val Cys Asp Glu Phe Thr Gly Ile Glu Pro Leu Ser Glu Asp Ala Ile
            580                 585                 590

Ile Thr Gly Phe Arg Asn Val Thr Ile Cys Pro Asn Pro Glu Asp Thr
            595                 600                 605

Cys Asp Phe Ala Arg Ala Ala Arg Phe Val Ser Thr Pro Phe His Glu
        610                 615                 620

Ile Met Ser Leu Lys Asp Leu Pro Ser Asp Pro Glu Arg Leu Leu Pro
625                 630                 635                 640

Glu Glu Asp Leu Asp Val Lys Thr Ser Glu Asp Gln Thr Ala Cys
                645                 650                 655

Gly Thr Ile Tyr Ser Gln Thr Leu Ser Ile Lys Lys Leu Ser Pro Ile
                660                 665                 670

Ile Glu Asp Ser Arg Glu Ala Thr His Ser Ser Gly Phe Ser Gly Ser
        675                 680                 685

Ser Ala Ser Val Ala Ser Thr Ser Ser Ile Lys Cys Leu Gln Ile Pro
```

```
                690             695              700
Glu Lys Leu Glu Leu Thr Asn Glu Thr Ser Glu Asn Pro Thr Gln Ser
705                 710             715                 720

Pro Trp Cys Ser Gln Tyr Arg Arg Gln Leu Leu Lys Ser Leu Pro Glu
                725             730             735

Leu Ser Ala Ser Ala Glu Leu Cys Ile Glu Asp Arg Pro Met Pro Lys
            740             745             750

Leu Glu Ile Glu Lys Glu Ile Glu Leu Gly Asn Glu Asp Tyr Cys Ile
        755             760             765

Lys Arg Glu Tyr Leu Ile Cys Glu Asp Tyr Lys Leu Phe Trp Val Ala
    770             775             780

Pro Arg Asn Ser Ala Glu Leu Thr Val Ile Lys Val Ser Ser Gln Pro
785             790             795                 800

Val Pro Trp Asp Phe Tyr Ile Asn Leu Lys Leu Lys Glu Arg Leu Asn
                805             810             815

Glu Asp Phe Asp His Phe Cys Ser Cys Tyr Gln Tyr Gln Asp Gly Cys
            820             825             830

Ile Val Trp His Gln Tyr Ile Asn Cys Phe Thr Leu Gln Asp Leu Leu
        835             840             845

Gln His Ser Glu Tyr Ile Thr His Glu Ile Thr Val Leu Ile Ile Tyr
    850             855             860

Asn Leu Leu Thr Ile Val Glu Met Leu His Lys Ala Glu Ile Val His
865             870             875                 880

Gly Asp Leu Ser Pro Arg Cys Leu Ile Leu Arg Asn Arg Ile His Asp
                885             890             895

Pro Tyr Asp Cys Asn Lys Asn Asn Gln Ala Leu Lys Ile Val Asp Phe
            900             905             910

Ser Tyr Ser Val Asp Leu Arg Val Gln Leu Asp Val Phe Thr Leu Ser
        915             920             925

Gly Phe Arg Thr Val Gln Ile Leu Glu Gly Gln Lys Ile Leu Ala Asn
    930             935             940

Cys Ser Ser Pro Tyr Gln Val Asp Leu Phe Gly Ile Ala Asp Leu Ala
945             950             955                 960

His Leu Leu Leu Phe Lys Glu His Leu Gln Val Phe Trp Asp Gly Ser
                965             970             975

Phe Trp Lys Leu Ser Gln Asn Ile Ser Glu Leu Lys Asp Gly Glu Leu
            980             985             990

Trp Asn Lys Phe Phe Val Arg Ile  Leu Asn Ala Asn Asp  Glu Ala Thr
        995             1000             1005

Val Ser  Val Leu Gly Glu Leu  Ala Ala Glu Met Asn  Gly Val Phe
1010             1015             1020

Asp Thr  Thr Phe Gln Ser His  Leu Asn Lys Ala Leu  Trp Lys Val
    1025             1030             1035

Gly Lys  Leu Thr Ser Pro Gly  Ala Leu Leu Phe Gln
    1040             1045             1050

<210> SEQ ID NO 2
<211> LENGTH: 3749
<212> TYPE: DNA
<213> ORGANISM: Homo sapiens

<400> SEQUENCE: 2 agggcgtgg   ccacgtcgac   cgcgcgggac   cgttaaattt   gaaacttggc   ggctaggggt      60
gtgggcttga   ggtggccggt   ttgttaggga   gtcgtgtacg   tgccttggtc   gcttctgtag     120
```

```
ctccgagggc aggttgcgga agaaagccca ggcggtctgt ggcccagagg aaaggcctgc      180
agcaggacga ggacctgagc caggaatgca ggatggcggc ggtgaagaag aaggggggtg      240
ctctgagtga agccatgtcc ctggagggag atgaatggga actgagtaaa gaaaatgtac      300
aacctttaag gcaagggcgg atcatgtcca cgcttcaggg agcactggca caagaatctg      360
cctgtaacaa tactcttcag cagcagaaac gggcatttga atatgaaatt cgattttaca      420
ctggaaatga ccctctggat gtttgggata ggtatatcag ctggacagag cagaactatc      480
ctcaaggtgg gaaggagagt aatatgtcaa cgttattaga agagctgta gaagcactac       540 aaggagaaaa acgatattat agtgatcctc gatttctcaa tctctggctt aaattagggc      600
gtttatgcaa tgagcctttg gatatgtaca gttacttgca caaccaaggg attggtgttt      660
cacttgctca gttctatatc tcatgggcag aagaatatga agctagagaa aactttagga      720
aagcagatgc gatatttcag gagggattc aacagaaggc tgaaccacta gaaagactac       780
agtcccagca ccgacaattc caagctcgag tgtctcggca aactctgttg gcacttgaga      840
aagaagaaga ggaggaagtt tttgagtctt ctgtaccaca acgaagcaca ctagctgaac      900
taaagagcaa agggaaaaag acagcaagag ctccaatcat ccgtgtagga ggtgctctca      960
aggctccaag ccagaacaga ggactccaaa atccatttcc tcaacagatg caaaataata     1020
gtagaattac tgttttgat gaaaatgctg atgaggcttc tacagcagag ttgtctaagc      1080
ctacagtcca gccatggata gcacccccca tgcccagggc caaagagaat gagctgcaag     1140
caggcccttg gaacacaggc aggtccttgg aacacaggcc tcgtggcaat acagcttcac     1200
tgatagctgt acccgctgtg cttcccagtt tcactccata tgtggaagag actgcacaac     1260
agccagttat gacaccatgt aaaattgaac ctagtataaa ccacatccta agcaccagaa     1320
agcctggaaa ggaagaagga gatcctctac aaagggttca gagccatcag caagcgtctg     1380
aggagaagaa agaagatg atgtattgta aggagaagat ttatgcagga gtagggaat        1440 tctcctttga agaaattcgg gctgaagttt tccggaagaa attaaaagag caagggaag      1500 ccgagctatt gaccagtgca gagaagagag cagaaatgca gaaacagatt gaagagatgg     1560
agaagaagct aaaagaaatc caaactactc agcaagaaag aacaggtgat cagcaagaag     1620
agacgatgcc tacaaaggag acaactaaac tgcaaattgc ttccgagtct cagaaaatac     1680
caggaatgac tctatccagt tctgtttgtc aagtaaactg ttgtgccaga gaaacttcac     1740
ttgcggagaa catttggcag gaacaacctc attctaaagg tcccagtgta cctttctcca     1800
tttttgatga gtttcttctt tcagaaaaga gaataaaag tcctcctgca gatccccac      1860 gagttttagc tcaacgaaga ccccttgcag ttctcaaaac ctcagaaagc atcacctcaa     1920
atgaagatgt gtctccagat gtttgtgatg aatttacagg aattgaaccc ttgagcgagg     1980
atgccattat cacaggcttc agaaatgtaa caatttgtcc taaccagaa gacacttgtg      2040 actttgccag agcagctcgt tttgtatcca ctcctttca tgagataatg tccttgaagg      2100 atctccttc tgatcctgag agactgttac cggaagaaga tctagatgta aagacctctg     2160
aggaccagca gacagcttgt ggcactatct acagtcagac tctcagcatc aagaagctga      2220
gcccaattat tgaagacagt cgtgaagcca cacactcctc tggcttctct ggttcttctg     2280
cctcggttgc aagcacctcc tccatcaaat gtcttcaaat tcctgagaaa ctagaactta     2340
ctaatgagac ttcagaaaac cctactcagt caccatggtg ttcacagtat cgcagacagc     2400
tactgaagtc cctaccagag ttaagtgcct ctgcagagtt gtgtatagaa gacagaccaa     2460
```

```
tgcctaagtt ggaaattgag aaggaaattg aattaggtaa tgaggattac tgcattaaac      2520
gagaatacct aatatgtgaa gattacaagt tattctgggt ggcgccaaga aactctgcag      2580
aattaacagt aataaaggta tcttctcaac ctgtcccatg ggactttat atcaacctca       2640 agttaaagga acgtttaaat gaagattttg atcattttg cagctgttat caatatcaag       2700
atggctgtat tgtttggcac aatatataa actgcttcac ccttcaggat cttctccaac       2760
acagtgaata tattacccat gaaataacag tgttgattat ttataacctt ttgacaatag      2820
tggagatgct acacaaagca gaaatagtcc atggtgactt gagtccaagg tgtctgattc      2880
tcagaaacag aatccacgat ccctatgatt gtaacaagaa caatcaagct ttgaagatag      2940
tggacttttc ctacagtgtt gaccttaggg tgcagctgga tgttttacc ctcagcggct       3000 ttcggactgt acagatcctg gaaggacaaa agatcctggc taactgttct tctcccctacc    3060 aggtagacct gtttggtata gcagatttag cacatttact attgttcaag gaacacctac     3120
aggtcttctg ggatgggtcc ttctggaaac ttagccaaaa tatttctgag ctaaaagatg     3180
gtgaattgtg gaataaattc tttgtgcgga ttctgaatgc caatgatgag gccacagtgt     3240
ctgttcttgg ggagcttgca gcagaaatga atggggtttt tgacactaca ttccaaagtc     3300
acctgaacaa agccttatgg aaggtaggga agttaactag tcctgggct ttgctctttc      3360 agtgagctag gcaatcaagt ctcacagatt gctgcctcag agcaatggtt gtattgtgga    3420
acactgaaac tgtatgtgct gtaatttaat ttaggacaca tttagatgca ctaccattgc    3480
tgttctactt tttggtacag gtatatttg acgtcactga tatttttat acagtgatat      3540 acttactcat ggccttgtct aacttttgtg aagaactatt ttattctaaa cagactcatt    3600
acaaatggtt accttgttat ttaacccatt tgtctctact tttccctgta cttttcccat    3660
ttgtaatttg taaaatgttc tcttatgatc accatgtatt ttgtaaataa taaaatagta   3720
tctgttaaat ttgtgcttct aaaaaaaaa                                        3749

<210> SEQ ID NO 3
<211> LENGTH: 19
<212> TYPE: RNA
<213> ORGANISM: artificial sequence
<220> FEATURE:
<223> OTHER INFORMATION: synthetic construct

<400> SEQUENCE: 3
gauggugaau uguggaaua                                                     19

<210> SEQ ID NO 4
<211> LENGTH: 19
<212> TYPE: RNA
<213> ORGANISM: artificial sequence
<220> FEATURE:
<223> OTHER INFORMATION: synthetic construct

<400> SEQUENCE: 4
gaaacgggca uuugaauau                                                     19

<210> SEQ ID NO 5
<211> LENGTH: 19
<212> TYPE: RNA
<213> ORGANISM: artificial sequence
<220> FEATURE:
<223> OTHER INFORMATION: synthetic construct

<400> SEQUENCE: 5
gcaaugagcc uuuggauau                                                     19
```

```
<210> SEQ ID NO 6
<211> LENGTH: 19
<212> TYPE: RNA
<213> ORGANISM: artificial sequence
<220> FEATURE:
<223> OTHER INFORMATION: synthetic construct

<400> SEQUENCE: 6
caauacagcu ucacugaua                                          19
```